United States Patent
Boll et al.

(10) Patent No.: US 10,737,109 B2
(45) Date of Patent: Aug. 11, 2020

(54) SYSTEMS AND METHODS OF UNATTENDED TREATMENT OF A SUBJECT'S HEAD OR NECK

(71) Applicant: Cynosure, LLC, Westford, MA (US)

(72) Inventors: James Boll, Auburndale, MA (US); Robert D. McCarthy, Maynard, MA (US); Rafael Armando Sierra, Westford, MA (US); Brian R. Sutherland, Tewksbury, MA (US); Allan Cameron, South Natick, MA (US); Adrian Mark West, Newton, MA (US); Elizabeth Kneen Winter, Somerville, MA (US); Kevin Young, Needham, MA (US)

(73) Assignee: CYNOSURE, LLC, Westford, MA (US)

(*) Notice: Subject to any disclaimer, the term of this patent is extended or adjusted under 35 U.S.C. 154(b) by 399 days.

(21) Appl. No.: 15/485,178

(22) Filed: Apr. 11, 2017

(65) Prior Publication Data
US 2017/0266461 A1    Sep. 21, 2017

Related U.S. Application Data

(63) Continuation-in-part of application No. 15/138,020, filed on Apr. 25, 2016, now Pat. No. 10,518,104.
(Continued)

(51) Int. Cl.
*A61N 5/06* (2006.01)
*A61N 5/067* (2006.01)
*A61N 5/00* (2006.01)

(52) U.S. Cl.
CPC ......... *A61N 5/0616* (2013.01); *A61N 5/0625* (2013.01); *A61N 2005/005* (2013.01);
(Continued)

(58) Field of Classification Search
CPC ............ A61N 5/0616; A61N 5/0625; A61N 2005/005; A61N 2005/007;
(Continued)

(56) References Cited

U.S. PATENT DOCUMENTS 2,353,643 A * 7/1944 Bulbulian ............... A61F 7/10
                                                    607/109
5,029,581 A    7/1991 Kaga et al.
(Continued)

FOREIGN PATENT DOCUMENTS

CN      204815398 U     7/2015
EP      2110159 A1     10/2009
(Continued)

OTHER PUBLICATIONS

Screen captures from YouTube video clip entitled "Nubway Model (NBW-1323", 11 pages, published on Aug 25, 2015. <https://www.youtube.com/watch?v=NcY4P7aWVbs>.
(Continued)

*Primary Examiner* — Erin M Piateski
(74) *Attorney, Agent, or Firm* — K&L Gates LLP

(57) ABSTRACT

In accordance with various aspects of the present teachings, systems and methods for applying treatment energy, e.g., electromagnetic radiation such as laser radiation in the visible and near infrared wavelengths, to body areas having bulges and fat deposits, loose skin, pain, acne and/or wounds. In some aspects, the systems and methods can enable relatively lengthy treatments to be performed by having the practitioner set-up and/or start the treatment, thereafter allowing the treatment to proceed safely and effectively without the continued presence of the practitioner.

10 Claims, 32 Drawing Sheets

Related U.S. Application Data

(60) Provisional application No. 62/321,141, filed on Apr. 11, 2016, provisional application No. 62/321,141, filed on Apr. 11, 2016, provisional application No. 62/210,967, filed on Aug. 27, 2015, provisional application No. 62/151,894, filed on Apr. 23, 2015.

(52) U.S. Cl.
CPC .. *A61N 2005/007* (2013.01); *A61N 2005/063* (2013.01); *A61N 2005/067* (2013.01); *A61N 2005/0632* (2013.01); *A61N 2005/0642* (2013.01); *A61N 2005/0643* (2013.01); *A61N 2005/0647* (2013.01); *A61N 2005/0659* (2013.01); *A61N 2005/0662* (2013.01)

(58) Field of Classification Search
CPC ...... A61N 2005/063; A61N 2005/0632; A61N 2005/0642; A61N 2005/0643; A61N 2005/0647; A61N 2005/0659; A61N 2005/0662; A61N 2005/067
USPC .......................................................... 607/91
See application file for complete search history.

(56) References Cited

U.S. PATENT DOCUMENTS

| | | | |
|---|---|---|---|
| 5,735,844 A | 4/1998 | Anderson et al. | |
| 6,080,146 A | 6/2000 | Altshuler et al. | |
| 6,126,294 A * | 10/2000 | Koyama | A61M 21/00 |
| | | | 362/105 |
| 6,277,085 B1 | 8/2001 | Flynn | |
| 6,327,886 B1 | 12/2001 | Eriksson | |
| 6,508,813 B1 | 1/2003 | Altshuler | |
| 6,517,532 B1 | 2/2003 | Altshuler et al. | |
| 6,653,618 B2 | 11/2003 | Zenzie | |
| 6,663,620 B2 | 12/2003 | Altshuler et al. | |
| 6,878,144 B2 | 4/2005 | Altshuler et al. | |
| 6,974,451 B2 | 12/2005 | Altshuler et al. | |
| 6,976,985 B2 | 12/2005 | Altshuler et al. | |
| 6,997,923 B2 | 2/2006 | Altshuler et al. | |
| 7,351,252 B2 | 4/2008 | Altshuler et al. | |
| 7,540,869 B2 | 6/2009 | Altshuler et al. | |
| 7,586,957 B2 | 9/2009 | Sierra et al. | |
| 7,763,016 B2 | 7/2010 | Altshuler et al. | |
| 7,856,985 B2 | 12/2010 | Mirkov et al. | |
| 7,929,579 B2 | 4/2011 | Hohm et al. | |
| 8,002,768 B1 | 8/2011 | Altshuler et al. | |
| 8,265,446 B2 | 9/2012 | Lonero et al. | |
| 8,317,779 B2 | 11/2012 | Mirkov et al. | |
| RE43,881 E | 12/2012 | Baranov et al. | |
| 8,322,348 B2 | 12/2012 | Mirkov et al. | |
| 8,328,794 B2 | 12/2012 | Altshuler et al. | |
| 8,328,796 B2 | 12/2012 | Altshuler et al. | |
| 8,915,948 B2 | 12/2014 | Altshuler et al. | |
| 9,028,536 B2 | 5/2015 | Sierra et al. | |
| 9,326,910 B2 | 5/2016 | Eckhouse et al. | |
| 9,358,152 B2 | 6/2016 | Baxter et al. | |
| 2005/0197681 A1 | 9/2005 | Barolet et al. | |
| 2005/0215987 A1 | 9/2005 | Slatkine | |
| 2005/0215988 A1 | 9/2005 | Altshuler et al. | |
| 2006/0004306 A1 | 1/2006 | Altshuler et al. | |
| 2006/0010583 A1* | 1/2006 | Dennis | A61B 18/203 |
| | | | 601/15 |
| 2007/0208326 A1 | 9/2007 | Connors et al. | |
| 2007/0270785 A1 | 11/2007 | Jones et al. | |
| 2008/0077199 A1* | 3/2008 | Shefi | A61N 5/0613 |
| | | | 607/88 |
| 2008/0086187 A1 | 4/2008 | Baxter et al. | |
| 2009/0054880 A1 | 2/2009 | Aharon | |
| 2010/0204762 A1 | 8/2010 | De Taboada et al. | |
| 2013/0178764 A1 | 7/2013 | Eckhouse et al. | |
| 2014/0194957 A1 | 7/2014 | Rubinfeld et al. | |
| 2014/0350643 A1 | 11/2014 | Pepitone et al. | |
| 2015/0045675 A1 | 2/2015 | Chernomorsky | |
| 2016/0158575 A1 | 6/2016 | Levatter | |
| 2016/0287333 A1 | 10/2016 | Morrison | |
| 2017/0266426 A1 | 9/2017 | Ha et al. | |

FOREIGN PATENT DOCUMENTS

| | | |
|---|---|---|
| KR | 100353164 | 11/1999 |
| KR | 20060031262 | 10/2004 |
| KR | 20160014740 | 1/2016 |
| KR | 101906514 | 5/2017 |
| WO | 2010100540 A1 | 9/2010 |
| WO | 2017180663 | 10/2017 |

OTHER PUBLICATIONS

Screen captures from YouTube video clip entitled "Cryolipolysis Fat Freezing Machine", 11 pages, published on Nov 6, 2015, Cryolipolysis Machine for sale. Retrieved from Internet: <https://www.youtube.com/watch?v+9d_QLIr9LHE>.

VelaShape II: Cellulite Treatment & Body Contouring, Candela, 2011 (8 Pages).

Invitation to Pay Additional Fees and, Where Applicable, Protest Fee, received in PCT/US20171027067 dated Jun. 28, 2017; 14 pages.

International Search Report and Written Opinion received in PCT/US2017/027067 dated Sep. 4, 2017; 21 pages.

* cited by examiner

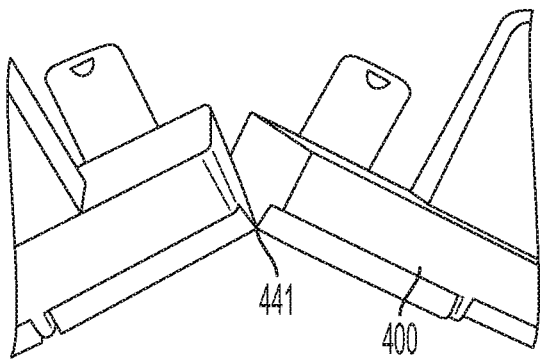
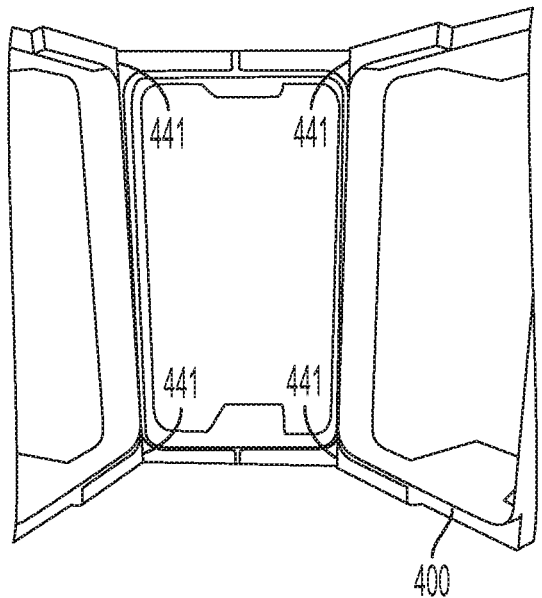
FIG. 9A  FIG. 9B
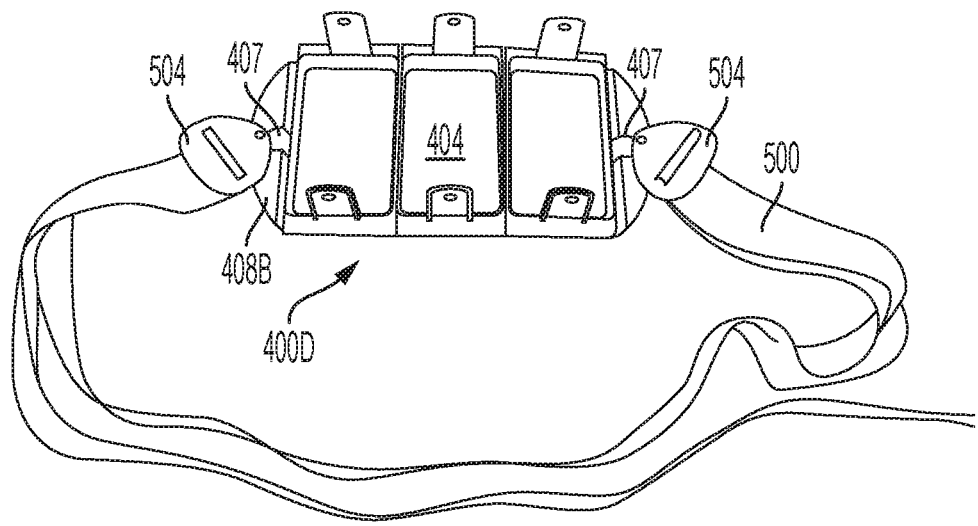
FIG. 10

SYSTEMS AND METHODS OF UNATTENDED TREATMENT OF A SUBJECT'S HEAD OR NECK

RELATED APPLICATIONS

This application claims the benefit of priority to U.S. Provisional App. No. 62/321,141, which was filed on Apr. 11, 2016 and which is incorporated herein by reference in its entirety. This application also claims the benefit of priority as a continuation-in-part of U.S. application Ser. No. 15/138,020, which was filed on Apr. 25, 2016, which claims the benefit of priority of U.S. Provisional App. Nos. 62/321,141 (which was filed on Apr. 11, 2016), 62/210,967 (which was filed on Aug. 27, 2015), and 62/151,894 (which was filed on Apr. 23, 2015), each of which is incorporated herein by reference in its entirety.

FIELD

The present disclosure relates generally to systems and methods for applying energy (e.g., electromagnetic radiation such as laser radiation in the visible and near infrared wavelengths) to treat, for example, body areas having bulges and fat deposits, loose skin, pain, acne and/or wounds. In various aspects, the present disclosure particularly relates to systems for effectively targeting certain regions of tissue, for example, adipose tissue in a subject's head or neck region including the submental area that can cause the appearance of a "double chin."

BACKGROUND

The benefits of being able to raise and/or lower the temperature in a selected region of tissue for various therapeutic and cosmetic purposes has been known for some time. For instance, heated pads or plates or various forms of electromagnetic radiation, including microwave radiation, electricity, infrared radiation and ultrasound have previously been used for heating subdermal muscles, ligaments, bones and the like to, for example, increase blood flow, to otherwise promote the healing of various injuries and other damage, and for various therapeutic purposes, such as frostbite or hyperthermia treatment, treatment of poor blood circulation, physical therapy, stimulation of collagen, cellulite treatment, adrenergic stimulation, wound healing, psoriasis treatment, body reshaping, non-invasive wrinkle removal, etc. Heating may be applied over a small localized area, over a larger area, for example to the hands or feet, or over larger regions of tissue, including the entire body. Subcutaneous fat in the submental region (e.g., under the chin), for example, can be aesthetically unappealing and can cause undesirable cosmetic effects even after substantial weight loss due to the sagging of the skin.

While optical and near infrared (NIR) radiation (collectively referred to hereinafter as "optical radiation") is generally both less expensive, and being non-mutagenic, safer than microwave radiation, the use of optical radiation has heretofore not been considered suitable for most applications involving heating of tissue at depth, the term "tissue at depth" as used herein meaning tissue at the border zone of the dermis and hypodermis, some of which tissue may be in the lower dermis, mostly at a depth deeper than 1 mm, and tissue below this border zone to a depth of up to about 50 mm. The reason why optical radiation has not been considered suitable is because such radiation is both highly scattered and highly absorbed in surface layers of tissue, precluding significant portions of such radiation from reaching the tissue regions at depth to cause heating thereof. In view of the energy losses due to scattering and absorption, substantial optical (including NIR) energy must be applied in order for enough such energy to reach a region of tissues at depth to have a desired effect. However, such high energy can cause damage to the surface layers of tissue, making it difficult to achieve desired photothermal treatments in tissue regions at depth. For these reasons, optical radiation has had limited value for therapeutic and cosmetic treatments on tissue at depth.

SUMMARY

In order to enable photothermal treatment of tissue regions at depth (e.g., hyperthermic treatment of fatty tissue), various aspects of the present teachings provide methods and systems for modulating the application of radiation (or modulating the intensity of the radiation applied to the tissue) over an extended treatment time. By way of non-liming example, the photothermal treatment of fatty tissue can raise the mean tissue temperature at a treatment site at depth above about 40° C., e.g., from about 40° C. to about 48° C., or from about 42° C. to about 46° C. by applying laser irradiation to the treatment site to maintain this supraphysiological temperature (greater than 37° C.) at the treatment site over a relatively extended period of time (e.g., a few minutes to hours depending on the particular temperature applied). In some aspects, for example, the treatment radiation can be applied over a relatively long duration (e.g., from about 3 to about 50 minutes, or from about 10 to about 45 minutes, or from about 15 to about 35 minutes, or about 25 minutes) to achieve the desired depth of treatment, thereby heating fatty tissue to trigger heat-induced injury that causes the adipocytes to undergo apoptosis or lipolysis. The residual cellular debris is gradually removed by the body through inflammation and the resultant immune system clearing process, which can take weeks to months depending on the extent of injury at the site. Since the regeneration process of adipose tissue is very slow (over years), the total volume of fat within the treatment area decreases due to loss of adipocytes that would otherwise act as storage units for fat.

Since the techniques described above involve applying treatment energy through the patient's skin surface, peak temperatures generally occur at or near the patient's skin surface and decrease, sometimes significantly, with depth. Notably, 46° C. or 48° C. is not the upper limit of treatment, as higher temperatures (47-50° C. or more e.g. 60° C., 70° C., 80° C., etc.) can also be effective to denature cells and ablate tissue, but these likewise raise the mean heat level in the non-target tissues and possibly cause collateral damage. Because it is desirable to confine the hyperthermic treatment to the target tissue while keeping temperatures of dermal tissue above the targeted tissue at depth below injury threshold (i.e., lower than about 46-47° C.), the electromagnetic treatment parameters (such as radiation pattern, fluence, exposure time, etc.) can be modulated over the extended treatment time, and in some aspects by taking into account the cooling rate on the skin surface, an optimized temperature profile/gradient in the target tissue can be achieved during the treatment.

One exemplary technique, called Selective Photothermolysis (SPTL), has been widely used for various photothermal therapies, such as hair removal and superficial vascular treatment. The objective of SPTL is to choose an energy source, e.g., laser light, having a specific wavelength that is selectively or preferentially absorbed by the targeted tissue (such as adipocytes and lipid bilayer structures), with less absorption and therefore less thermal effect on the surrounding tissues (such as epidermis). Optimal SPTL is achieved when the targeted tissue has a much higher energy absorption compared to other surrounding tissues. Frequently, this effect is controlled by selecting lasers having particular wavelengths for specific cosmetic purposes. But in certain procedures, selection of wavelength alone is not itself sufficient to create a large enough energy absorption differential between target and non-target tissues to achieve optimal therapeutic effects without some degree of damage to surrounding non-target tissues. Approaches that increase the energy absorption differential and control heating at the treatment site while lessening collateral damage of non-target tissues can in some aspects involve modulating the radiation exposure through pulsed applications of laser light. For example, in accordance with various aspects of the present teachings, the methods and systems can utilize a near infrared laser having a wavelength within the range of 1064 nm that is selected based on its tissue penetrance and the relatively low absorption of the EMR by the major chromophores in the skin (e.g., melanin and water). Exemplary power densities are from about 0.5 to about 10 W/cm$^2$, or from about 4 to about 6 W/cm$^2$, and a particularly useful range is about 0.9 to about 1.4 W/cm$^2$. Alternatively, suitable systems can utilize a wavelength within the range of about 800 nm to about 1300 nm, selected based on tissue penetrance, and power densities from about 0.5 to about 10 W/cm$^2$, or from about 4 to about 6 W/cm$^2$, and a particularly useful range is about 0.9 to about 1.4 W/cm$^2$. To maintain an appropriate hyperthermic temperature range in the target tissue (e.g., about 40-47° C. in the fat layer) while avoiding pain and other unwanted side effects related to overheating, the laser can be modulated such that it can be pulsed so as to generate an on/off pattern or by modulating the intensity of the laser (e.g., between a high intensity and low intensity), which causes the temperature to cycle within the appropriate hyperthermic temperature range, as disclosed for example in U.S. Pub No. 20080103565 entitled "Method and Apparatus for Treatment of Cutaneous and Subcutaneous Conditions" and U.S. Pub. No. 20070213792 entitled "Treatment of Tissue Volume with Radiant Energy," the teachings of which are incorporated by reference in their entireties. With the laser on (or at a desired relatively high intensity), the temperature can rise to the upper limits of the desired range. A periodic pause in radiation (or a lowering of the intensity) permits temperatures in the target site (and non-target site) to drop. Optionally, cooling (especially of the upper non-target tissue) can be further enhanced by using external devices (e.g., contact cooling), while laser radiation can resume (or its intensity is increased) before the target tissue temperature drops below the appropriate hyperthermic temperature range. In some embodiments, radiation is delivered through the contact cooled surface, which continuously cools. Alternatively, contact cooling is modulated via pulse on and off in concert with the delivery of radiation. The pulses can be repeated for the duration of the treatment (e.g., from about 3 minutes to about 2 hours, from about 5 minutes to about 45 minutes, from about 15 minutes to about 35 minutes, or about 25 minutes).

With such extended treatment times, it may also be desirable that at least some, if not all, of the treatment can be accomplished hands-free and/or at times by the practitioner. By way of example, a hands free system in accordance with various aspects of the present teachings could enable the practitioner to start treatment of a first patient with a first system, and allow the practitioner to attend to or treat a second subject during the first subject's relatively long treatment time. In various aspects, such a substantially unattended approach can reduce the costs associated with treatment by freeing up the practitioner's time and potentially enable a less skilled practitioner to be able to conduct a majority of the treatment. For example, a less skilled practitioner can check in with and talk to the patient, to get a sense of the patient's comfort and then call in a more skilled practitioner to adjust the treatment parameters if necessary. In accordance with some aspects of the present teachings, the systems and methods for relatively hands-free and/or substantially unattended treatment described herein can provide treatment that is reliable, safe, and/or relatively comfortable to the patient over the length of the treatment time. In addition, various aspects of the systems and methods disclosed enable customization so as to fit various body areas requiring treatment and/or the isolation of the target treatment area. For example, in various aspects, systems are provided for treating certain regions of adipose tissue on a patient's head or neck (e.g., a subject's submental area, jowls, cheeks), while helping to provide good optical coupling between the treatment radiation source and the subject's skin and patient comfort during the extended treatment time.

In accordance with various exemplary aspects of the present teachings, a system for substantially unattended treatment of body tissue (e.g., in the head or neck region) is provided, the system comprising a housing and at least one source of electromagnetic radiation for generating treatment energy contained within the housing. The system also comprises a plurality of applicators, with each of the applicators being adapted to be placed in proximity to a treatment region of tissue of a patient's body and comprising a window having a skin-contacting surface through which the treatment energy is transmitted from the applicator to the treatment region. A plurality of umbilical cords, each of which extends from the housing to a distal end coupled to one of the plurality of applicators, defines a conduit through which treatment energy generated by the at least one electromagnetic radiation source is delivered from the housing to the applicator (e.g., through at least one optical waveguide extending through the conduit). The system can also comprise a frame configured to be coupled to the patient's body in a fixed position relative to the treatment region and defining at least one aperture into which a surface of the treatment region can extend. The frame and at least one applicator can be coupled to one another in a variety of manners, but are generally removably coupled such that at least a portion of the skin-contacting surface of the window is disposed in contact with at least a portion of the surface of the treatment region extending into the aperture upon coupling the applicator with the frame. In some aspects, for example, the frame and the applicator can comprise complementary mating features for removably coupling the applicator to the frame. By way of example, the frame can comprise a snap-fit coupling mechanism for removably coupling the applicator to the frame. In various aspects, the system can additionally comprise an adjustable belt configured to be coupled to the frame for securing the frame to the patient's body.

In some aspects, the housing can comprise at least one arm extending from the housing for supporting the umbilical cords. For example, the arm can extend from the housing so as to be disposed above the patient's body when performing treatment so as to maintain secure contact between the skin-contacting surface of the applicator and the portion of the surface of the treatment region extending into the aperture of the frame. In various aspects, the housing can be maneuverable (e.g., it can include wheels to position the housing and the umbilical cords extending therefrom in a desired position) and/or the arm(s) can be adjustable so as to alter its orientation relative to the patient. In some exemplary aspects, the arm can additionally comprise at least one brake (e.g., a roller brake) in contact with the plurality of umbilical cords so as to maintain the umbilical cords at a desired position relative to the patient. By way of example, the at least one brake can limit movement of the umbilical cords when performing treatment so as to facilitate secure contact between the skin-contacting surface of the applicator and the portion of the surface of the treatment region extending into the aperture of the frame when coupled to the applicator. Additionally or alternatively, the brake can enable a desired amount of lead of the umbilical cord to be maintained between the brake and the applicator at the distal end of the umbilical cord. Moreover, each umbilical cord can be associated with its own brake such that the desired lead for each umbilical cord can be adjusted individually.

In various aspects, the frame can define a plurality of apertures, each of which can isolate a portion of a target treatment region. Additionally or alternatively, two or more frames can be used to isolate portions of the target treatment region. In various aspects, the frame can be configured to be simultaneously coupled with two or more of the plurality of applicators such that the skin-contacting surface of each of the applicators is disposed in contact with the portion of the surface of the treatment region extending into one of the apertures. In such aspects, for example, the frame can comprise a hinge disposed between adjacent apertures such that the orientation of the apertures can be adjusted relative to each other (e.g., upon tightening a belt coupled to the frame about a portion of the subject's body).

In various aspect, the system can further comprise a cooling mechanism configured to cool the skin-contacting surface of the applicators when performing treatment. By way of non-limiting example, a fluid pathway can extend through the conduit for circulating cooling fluid between the housing and the applicator via the umbilical cord.

Additionally, in some aspects, each of the applicators can comprise a contact sensor to determine whether the skin-contacting surface of the window is disposed in contact with the surface of the treatment region.

In various aspects of the present teachings, the system can comprise at least one mask configured to be coupled to the frame and configured to occlude the aperture of the frame so as to prevent a portion of the surface of the patient's body from extending into the aperture and into contact with the window of the applicator. It will be appreciated in light of the present teachings that the mask can also be coupled to a cooling mechanism for cooling the mask during treatment. In some aspects, the mask can define an unmasked portion having an area smaller than each of the window of the applicator and the aperture of the frame associated with the mask, with each of the applicators comprising a contact sensor to determine whether the skin-contacting surface of the window is disposed in contact with the surface of the treatment region extending through the unmasked portion. Additionally or alternatively, at least one of the size and shape of the unmasked portion can be adjustable, for example, so as to customize the tissue to which the treatment energy is applied. To increase patient comfort during the procedure, for example, in some aspects the frame can comprise a skin-contacting surface disposed about the at least one aperture, wherein the skin-contacting surface of the frame is contoured to fit the area of the patient undergoing treatment. By way of example, the skin-contacting surface can be curved or non-planar so as to accommodate the submental region of a patient.

In accordance with various exemplary aspects of the present teachings, a method for treating body tissue is provided, the method comprising coupling a frame to a patient's body in a fixed position relative to a treatment region of tissue, the frame defining at least one aperture into which a surface of the treatment region extends. At least one applicator can be coupled to the frame, each applicator comprising a window having a skin-contacting surface through which treatment energy is configured to be transmitted from the applicator to the treatment region, wherein at least a portion of the skin-contacting surface of the window is disposed in contact with at least a portion of the surface of the treatment region extending into said aperture upon coupling with the frame. Thereafter, treatment energy can be transmitted to the portion of the surface of the treatment region extending through the aperture of the frame and disposed in contact with the skin-contacting surface of the window, the treatment energy being generated by at least one source of electromagnetic radiation disposed in a housing and delivered to the applicator via an umbilical cord extending from the housing to a distal end of the umbilical cord that is coupled to the applicator. In some aspects, coupling at least one applicator to the frame can comprise coupling a plurality of applicators to the frame, wherein each of the applicators is associated with a different umbilical cord and a different aperture of the frame configured to isolate a different surface of the treatment region.

In various aspects, the housing can additionally comprise at least one arm extending from the housing for supporting the umbilical cords, the method further comprising disposing the arm above the patient's body when performing treatment. In some exemplary aspects, the arm can also comprise at least one brake in contact with each of the plurality of umbilical cords so as to maintain a desired amount of lead of each umbilical cord between the at least one brake and the applicator associated with each umbilical cord.

In some exemplary aspects, coupling the frame to the patient's body can comprise securing a belt coupled to the frame around at least a portion of the patient's body. By way of example, when the treatment region comprises one of submental, jowl, and neck tissue, the belt can be secured about the patient's head and/or neck. Alternatively, when the treatment region comprises abdominal tissue, the flanks, the under-bra area (in the back or in the front), the belt can be secured about the patient's torso. Finally, when the treatment region comprises tissue of the patient's arm or leg (e.g., where the thighs meet and/or the saddle bag area), for example, the belt can be secured around the patient's arm or leg, respectively. In various related aspects, the frame can comprise a hinge disposed between adjacent apertures, wherein coupling the frame to the patient's body further comprises adjusting the orientation of the apertures relative to each other (e.g., as the belt is tightened about the patient).

In various aspects, the method can also include coupling the frame to at least one mask configured to occlude a portion of the frame's aperture so as to prevent a portion of the surface of the patient's body from extending into the aperture and into contact with the window of the applicator. The unmasked portion of the mask can have an area smaller than each of the window of the applicator and the aperture of the frame associated with the mask, the method further comprising adjusting at least one of the size and shape of the unmasked portion (e.g., so as to customize the tissue to which the treatment energy is applied).

In accordance with various aspects of the present teachings, a harness is provided to facilitate treatment of portions of a patient's body, for example, by improving patient comfort as the treatment is being applied, to ensure effective contact with the treatment region for effective coupling of the treatment energy into the skin, and/or to improve patient safety. By way of example, in some exemplary aspects, a harness is provided to facilitate treatment of a region of a subject's head or neck (e.g., the submental region, jowls, cheeks), the harness comprising an encircling portion configured to be secured to at least a portion of the subject's head (e.g., the encircling portion surrounds all or a portion of the subject's head) and a brim extending anteriorly from the encircling portion and configured to be disposed anterior to the subject's forehead when the encircling portion is secured to the subject's head, the brim comprising a plurality of anterior coupling elements on each lateral side of the subject's head anterior to the subject's temple. The harness can also comprise at least one frame defining at least one aperture into which a surface of the subject's skin can extend when the frame is secured to the desired treatment region of the subject's head or neck (e.g., the submental region, jowls, cheeks), the at least one frame being configured to be coupled to a treatment applicator (e.g., as described otherwise herein) comprising an window through which treatment energy is transmitted from the treatment applicator to the treatment region. At least one anterior connector can be provided comprising a superior mating feature configured to releasably couple to each of the plurality of anterior coupling elements of the brim on at least one lateral side of the subject's head so as to secure the frame to the subject's treatment region. The window may be an optical window to transmit optical energy. The window can enable other non-optical forms of treatment energy (e.g., RF energy) to be transmitted to the treatment region. The treatment region can include the lower part of the subject's head, such as the submental region, jowls, and cheeks, for example. In various aspects, the encircling portion can be configured to be secured to a subject's head above the level of the subject's ears. Additionally, in some aspects, the encircling portion can comprise a padded region configured to be disposed against the subject's forehead. A length of the encircling portion (e.g., a circumference or a portion of a circumference) can be adjustable to secure the encircling portion about the patient's head. Additionally, in some aspects, a superior connector can extend between opposed lateral sides of the encircling portion such that the superior portion can provide further support, for example, by being disposed against the top of the subject's head. In related aspect, the length of the superior connector can also be adjustable.

The brim can be coupled to the at least one frame in a variety of manners in accordance with the present teachings. By way of example, the harness can comprise two anterior connectors and the frame can comprise a lateral coupling element on each lateral side of the frame, each of the two anterior connectors comprising a superior mating feature configured to releasably couple to each of the plurality of anterior coupling elements of the brim on one lateral side of the subject's head and an inferior mating feature configured to couple to the lateral coupling element on the corresponding lateral side of the frame. In some related aspects, a length of each of the two anterior connectors can be adjustable after the superior mating feature is coupled to a selected anterior coupling element of the brim and the inferior mating feature is coupled to the lateral coupling element on the corresponding lateral side of the frame. Additionally, in various aspects, the encircling portion can comprise a posterior coupling element on each lateral side of the subject's head above and/or posterior to the subject's ears when the encircling portion is secured to the subject's head and the frame can comprise at least two lateral coupling elements on each of opposite lateral sides of the frame. In such aspects, the harness can further comprise two posterior connectors each of which can comprise a superior mating feature and an inferior mating feature, with each of the superior mating features being configured to releasably couple to a posterior coupling element on one lateral side of the subject's head and each of the inferior mating features being configured to couple to the lateral coupling element on the corresponding lateral side of the frame. In some aspects, a single anterior connector can be provided, for example, the anterior connector comprising two superior mating features, each of which is configured to couple to one of the plurality of anterior coupling elements on opposite lateral sides of the brim. In such aspects, the anterior connector can pass under the chin from one lateral side to the other and can be coupled to the frame (e.g., passed through a coupling loop extending from the frame) so as to fix the position of the frame against the treatment region. Additionally in some aspects, for example, in which a plurality of frames are provided (e.g., for treatment of the jowls or cheeks), the plurality of frames can be connected to one another (e.g., via strap passing under the patient's chin or via a hinge that connects adjacent frames) and also with mating elements from one lateral side of each frame being coupled to the anterior coupling elements on that lateral side of the brim.

In some aspects, the encircling portion can also comprise a posterior coupling element on each lateral side of the subject's head, for example, above and/or posterior to the subject's ears when the encircling portion is secured to the subject's head. In related aspects, the harness can further comprise two posterior connectors and the frame can comprise a lateral coupling element on opposite lateral sides of the frame, wherein each of the two posterior connectors comprises a superior mating feature and an inferior mating feature, the superior mating feature being configured to releasably couple to the posterior coupling element on one lateral side of the subject's head and the inferior mating feature being configured to couple to the lateral coupling element on the corresponding lateral side of the frame. In related aspects, a length of each of the two posterior connectors can be adjusted prior to or after the superior mating features is coupled to the posterior coupling element of the encircling portion and the inferior mating feature is coupled to the lateral coupling element on the corresponding lateral side of the frame. In some aspects, the harness can comprise at least one posterior connector comprising at least one mating feature configured to couple to the posterior coupling elements on each lateral side of the subject's head.

In various aspects, a length of the at least one anterior connector can be adjusted prior to or after the superior mating feature is coupled to one of the plurality of anterior coupling elements of the brim. Additionally or alternatively, the anterior connector comprises at least one of an elastic, a strap (e.g., a fabric strap made out of materials such as nylon), and a rigid element. In some aspects, the length of the strap can be adjustable.

In some aspects, the frame and the applicator can also comprise complementary mating features for removably coupling the applicator to the frame. By way of example, the frame can comprise a snap-fit coupling mechanism for removably coupling the applicator to the frame. In various aspects, the at least one frame can define a plurality of apertures, the frame being configured to simultaneously couple to two or more applicators such that a skin-contacting surface of each of said applicators is disposed in contact with a portion of the treatment region (e.g., submental region of jowls). In some related aspects, the frame(s) can comprise a hinge and/or connector disposed between adjacent apertures such that the orientation of the apertures can be adjusted relative to each other. In such aspects, for example, the hinge or connector can be placed under the patient's chin, with mating elements from one lateral side of each frame being coupled to the anterior coupling elements on that lateral side of the brim. In some aspects, at least one mask can be coupled to the frame and can be configured to occlude a portion of the aperture of the frame so as to prevent a portion of the surface of the subject's body from extending into the aperture and into contact with the window of the applicator. For example, the mask can define an unmasked portion having an area smaller than each window of the applicator and the aperture of the frame associated with the mask. In some aspects, the size and shape of the unmasked portion can be adjustable, can come in a range of unmasked aperture sizes with smaller mask aperture sizes making a greater portion of the applicator "visible" to the patient's tissue and larger mask aperture sizes making a lesser portion of the applicator "visible to the patient's tissue", and can come in a variety of shapes to address different treatment areas and/or different treatment requirements. Additionally or alternatively, the frame can comprise a skin-contacting surface disposed about the at least one aperture, wherein the skin-contacting surface of the frame about each of the at least one aperture is non-planar.

In accordance with various aspects of the present teachings, a method of treating a region of a subject's head or neck is provided, the method comprising coupling a harness to a subject's head such that an encircling portion of the harness is secured around at least a portion of a subject's head and a brim extending anteriorly from the encircling portion is disposed anterior to the subject's forehead, the brim comprising a plurality of anterior coupling elements on each lateral side of the subject's head anterior to the subject's temple. A superior mating feature of an anterior connector can be coupled to one of the plurality coupling elements of the brim and at least one frame coupled to the anterior connector can be disposed in contact with the desired treatment region (e.g., the subject's submental region, jowls, cheeks) such that a surface of the subject's skin extends through at least one aperture of the frame. A treatment applicator can be coupled to the at least one frame and treatment energy (e.g., EMR or RF energy) can be applied to the treatment region through the window and an aperture in the frame. As discussed throughout this disclosure in accordance with exemplary of the present teachings, the location of the coupling of the anterior connector to the brim can be adjusted so to improve patient comfort as the treatment is being applied, to ensure effective contact with the treatment region for effective coupling of the treatment energy into the skin, and/or to improve patient safety. For example, in some aspects, the method can comprise decoupling the superior mating feature of the anterior connector from said one of the plurality coupling elements of the brim and coupling with another of said plurality of coupling elements of the brim, for example, to change the angle by which the anterior connector couples the frame to the harness. The selection of the location of the coupling element on the brim can be made to improve the subject's comfort during treatment, to avoid contact between the side of the frame and/or applicator and the subject's neck and the sense of choking that such contact can elicit, and/or to enable safety glasses to be worn comfortably, Additionally or alternatively, a length of the one or more anterior connectors can be adjusted.

In some aspects, methods in accordance with the present teachings can comprise coupling an anterior connector to an anterior coupling element on each lateral side of the subject's head. In various aspects, the encircling portion can comprise a posterior coupling element on each lateral side of the subject's head above and/or posterior to the subject's ears, the method further comprising coupling a superior mating feature of each of two posterior connectors to the posterior coupling elements on the corresponding lateral side of the subject's head. In some related aspects, the method can comprise adjusting a length of the two posterior connectors.

In some aspects, coupling the harness to the patient's head can comprise adjusting a length of the encircling portion. Additionally, in some aspects, the harness can comprise a superior connector extending between opposed lateral sides of the encircling portion, the method further comprising adjusting a length of the superior connector to be disposed against the top of the subject's head.

These and other features of the applicant's teachings are set forth herein.

BRIEF DESCRIPTION OF THE DRAWINGS

The skilled person in the art will understand that the drawings, described below, are for illustration purposes only. The drawings are not intended to limit the scope of the applicant's teachings in any way.

FIGS. 9A-B depict additional detail of an exemplary frame for use in accordance with various aspects of the present teachings, the frame having a hinge disposed between the apertures for adjusting the orientation of the apertures when the frame is secured to the patient.

FIG. 10 depicts another exemplary frame having three apertures coupled to a belt for securing the frame about a portion of the patient's body.

DETAILED DESCRIPTION

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments.

Similarly it will be apparent that the described embodiments may be susceptible to alteration or variation according to common general knowledge without departing from the scope of the disclosure. The following detailed description of embodiments is not to be regarded as limiting the scope of the applicant's teachings in any manner.

In accordance with various aspects of the present teachings, systems and methods for providing photothermal treatment of tissue at depth are provided herein. In light of the extended treatment times typically utilized to perform such treatments, various aspects of the present teachings provide systems and methods for a reliable, safe, and/or relatively comfortable photothermal treatment to the patient in a manner that is relatively hands-free and/or with relatively little oversight, thereby potentially reducing the costs associated with continued oversight by the practitioner. In addition, various aspects of the systems and methods disclosed enable customization so as to fit various body areas requiring treatment and/or the isolation of the target treatment area.

Figure 1:
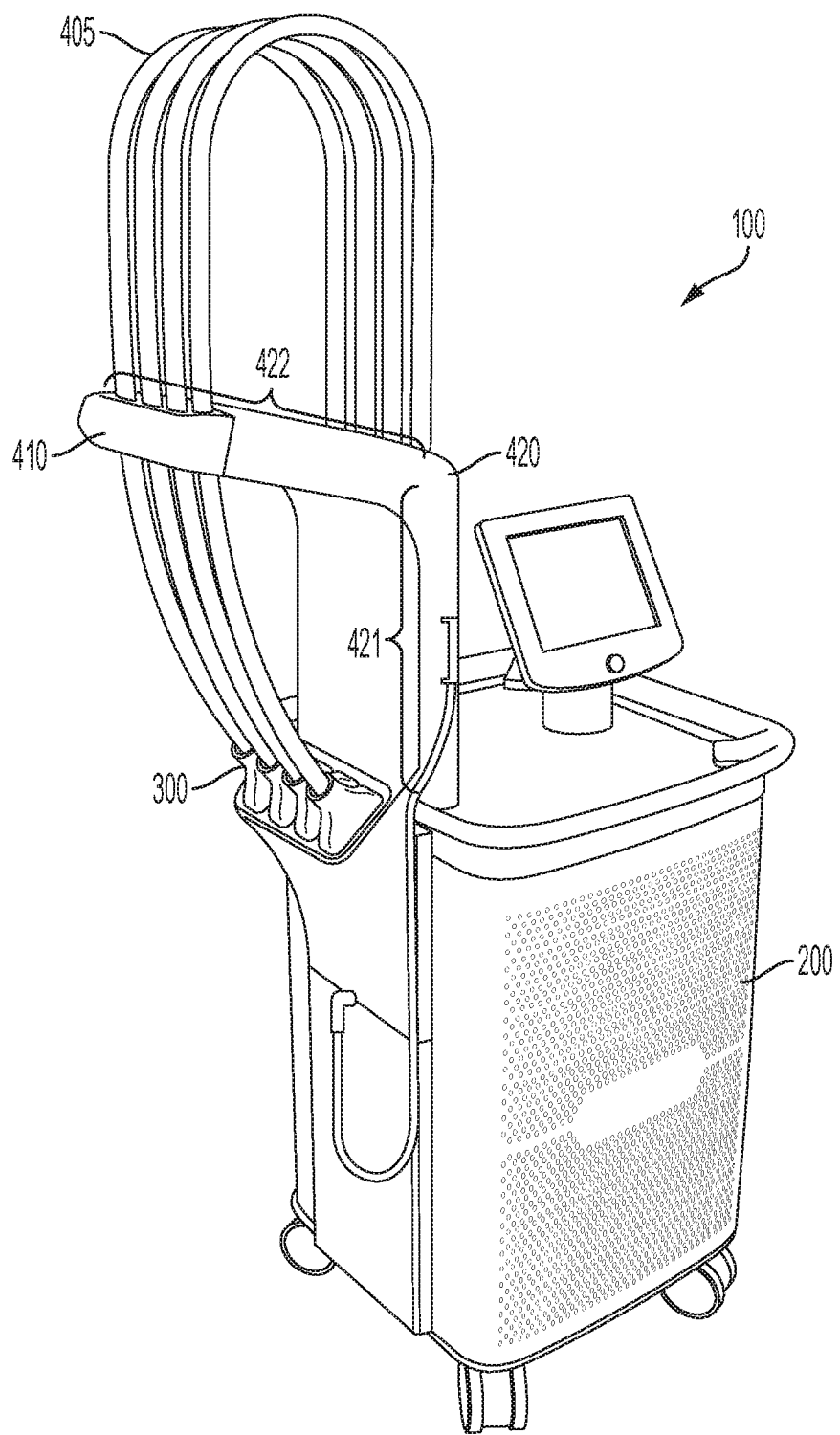
FIG. 1 shows an exemplary system for providing photothermal treatment of a target region of a patient's body in accordance with various aspects of the present teachings. As shown, the system includes a housing, a plurality of umbilical cords extending therefrom that are supported by an arm, and an applicator disposed at the distal end of each umbilical cord.
Figure 2:
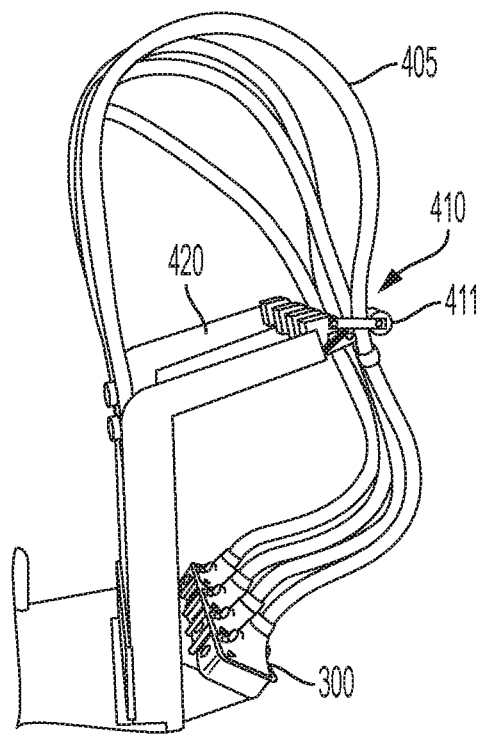
FIG. 2 shows a view of the system of FIG. 1 depicting the arm in additional detail. As shown, the arm includes a brake mechanism associated with each umbilical cord to assist in controlling the positioning and/or securement of the applicator. The housing additionally include a dock for storing the applicators when not in use.
Figure 3:
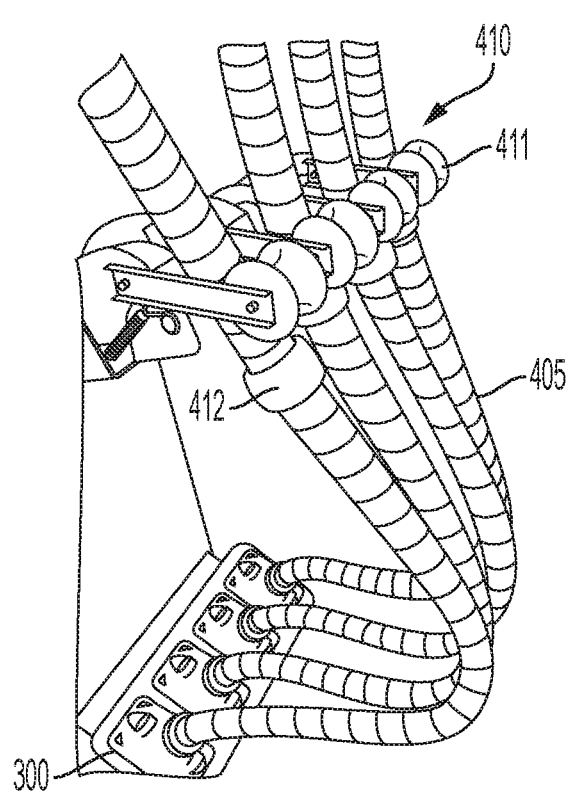
FIG. 3 depicts another view of the system of FIG. 1 showing the exemplary brake mechanism in additional detail.
Figure 4:
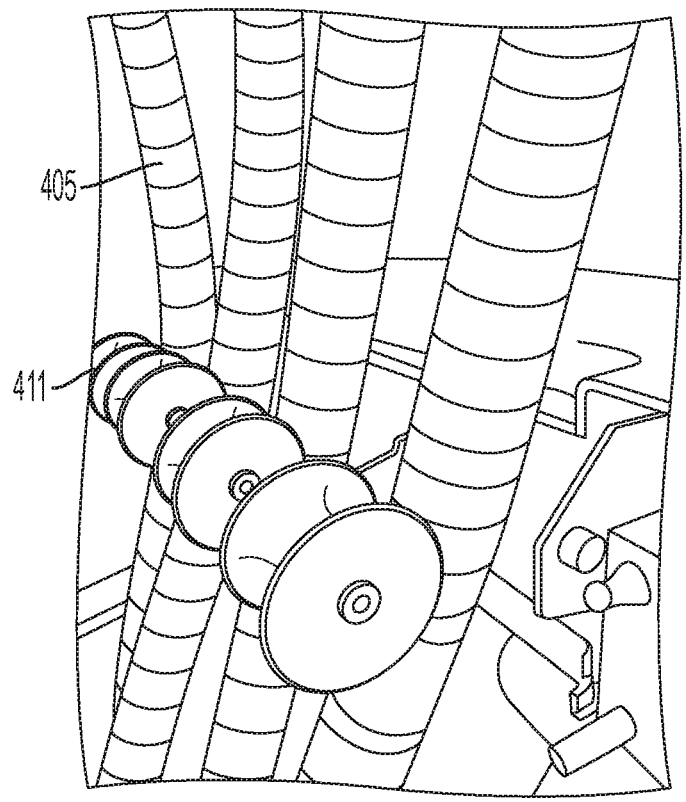
FIG. 4 depicts a close up of the exemplary brake mechanism.

Referring now to FIG. 1, an exemplary system 100 in accordance with various aspects of the present teachings is depicted. As shown, system 100 provides for the non-invasive (or less-invasive) photothermal treatment for fat reduction. Though the treatment is typically described with respect to the treatment of undesired body fat by the application of electromagnetic radiation to the fatty tissue through the external surface of the skin, it will nonetheless be appreciated by a person skilled that the systems and methods described herein can be utilized to provide any number of photothermal treatments known in the art and modified in accordance with the present teachings including the treatment of loose skin, pain, acne and/or wounds, all by way of non-limiting example. Exemplary approaches to photothermal treatment of tissue at depth and modified for use in accordance with methods and systems of the present teachings are disclosed, for example, in U.S. Pub. No. 20070213792 entitled "Treatment of Tissue Volume with Radiant Energy,"; U.S. Pub No. 20080103565 entitled "Method and Apparatus for Treatment of Cutaneous and Subcutaneous Conditions"; U.S. Patent Pub. No. 20140025033 entitled "Non-Invasive Fat Reduction by Hyperthermic Treatment"; U.S. Pat. No. 7,276,058 entitled "Method and Apparatus of Treatment of Cutaneous and Subcutaneous Conditions" issued on Oct. 2, 2007; U.S. Pat. No. 7,351,252 entitled "Method and Apparatus for Photothermal Treatment of Tissue at Depth" issued on Apr. 1, 2008; and U.S. Pat. No. 8,915,948 entitled "Method and Apparatus for Photothermal Treatment of Tissue at Depth" issued on Dec. 23, 2014, the teachings of which are incorporated by reference in their entireties.

As shown in FIG. 1, the exemplary system 100 for the non-invasive treatment of undesired body fat generally includes a housing 200 that can contain one or more sources of electromagnetic radiation (not shown), a plurality of umbilical cords 405 extending therefrom, and one or more applicators 300 coupled to the distal end of the umbilical cords 405 for applying the treatment radiation to the patient's skin when disposed in contact with the surface of the treatment region. Though the depicted exemplary system includes four applicators, any of a number of applicators 300 can be included in the system, for example, one applicator, two applicators, four applicators, or more. When not in use, the plurality of applicators 300 can be stored in a dock on the housing 200. Suitable energy sources can be, for example, temperature control (e.g., cooling and/or heating), light based energy sources, electromagnetic radiation, radiofrequency (RF) energy, and ultrasound energy, as known in the art and modified in accordance with the present teachings. As discussed in detail below, the treatment energy generated by the EMR source(s) can be delivered to the applicator, for example, via an optical waveguide (e.g., optical fiber) coupled to the EMR source(s) and extending through the umbilical cord 405.

As shown in FIGS. 1-4, the system 100 additionally comprises an arm 420 extending from the housing 200 that can support at least a portion of the umbilical cords 405, for example, above the subject to be treated and/or at a desired distance from the patient and/or other portions of the system including, for example, the housing 200 containing the energy source. The arm 420 can extend upward and outward from the housing in a variety of manners so as to support the umbilical cords 405 about or relative to the patient. As shown for example, the arm 420 includes a substantially vertical portion 421 extending from an upper surface of the housing 200 and a substantially horizontal portion 422 that extends from the top of the substantially vertical portion 421. The lengths of the vertical portion 421 and horizontal portion 422 can be fixed or can be adjustable in order to obtain proper positioning of the umbilical cords relative to the patient. By way of example, the arm 420 can include an adjustment mechanism (e.g., a telescoping portion hinge, pivot, or gimbaled mount) to adjust the length or angular orientation of one or more portions of the arm 420. In some aspects, the substantially vertical portion 421 of the arm 420 can have a height, for example, that is a function of the desired length (e.g., lead) of the umbilical 405 including, for example, a height in a range from about 8 inches to about 48 inches, from about 10 inches to about 36 inches, or about 12 inches. Likewise, the substantially horizontal portion 422 of the arm 420 can extend about 3 inches to about 36 inches, from about 9 inches to about 24 inches, or about 12 inches from the substantially vertical portion 421 such that the brake mechanism 410 (discussed in detail below) maintains the umbilical cords 405 at a distance of about 12 to 20 inches from the substantially vertical portion 421 of the arm 420 and/or from the housing 200.

As noted above and best shown in FIGS. 3 and 4, the arm 420 can also include a brake mechanism 410 for allowing the desired amount of lead from each of the plurality of umbilical cords 405 to be drawn toward the subject being treated and/or to help ensure that the umbilical cords 405 (and optionally additional umbilical lead) are at the desired position selected by the user. Though the exemplary system 100 is shown to include opposing roller brakes 441 disposed at the distal most end of the arms 420 as discussed in detail below, it will be appreciated that opposing roller brakes 411 is merely one approach to holding the plurality of umbilical cords 405 with some lead at a height above where the subject will be treated. Rather, it will be appreciated in light of the present teachings that any of a number of brake mechanisms can be employed for hold the umbilical cord 405 (and optionally, additional umbilical lead) at a desired position (e.g., height and/or distance) from the patient.

As noted above, the brake mechanism 410 comprises opposing roller brakes 411 between which the umbilical cords 405 extend and which apply a frictional or compression force to the cord 405 when disposed therebetween. In this manner, the roller brakes 411 can enable additional lead of the umbilical cord 405 to be pulled (e.g., with some resistance) toward the subject such that the skin-contacting surface of the applicator 300 attached to the umbilical cord 405 can sit with good contact on the skin surface of the patient. As otherwise discussed herein, the resistance and tension of the brake mechanism 410 enables the practitioner to tailor the amount of lead in each umbilical cord 405 for each respective applicator 300 in view of how to effectively place each applicator 300 into a frame 400 so that the contact surface of the applicator 300 is able to contact the subject's skin surface through the aperture 404 of the frame to ensure desired contact with the skin contact surface of the applicator 300 and the skin surface of the patient.

In various aspects, a self-retraction and positioning feature can also be built into the umbilical cord 405. By way of example, a spring can be disposed within a portion of the umbilical cord 405 (commonly referred to as a whip), that enables automatic retraction of the umbilical cord 405. After a user has completed use of the applicator 300 and unfastens the applicator 300 from the frame 400, for example, the user may simply push the umbilical cord 405 upward toward the brake mechanism 410 with a single hand. As a result the umbilical cord 405 can return to its initial position (e.g., as defined by stop 412 having a larger diameter than the umbilical cord 405) by a single handed movement of the user, with the stop 412 being positioned to allow the applicator 300 to be seated in its dock.

Figure 5:
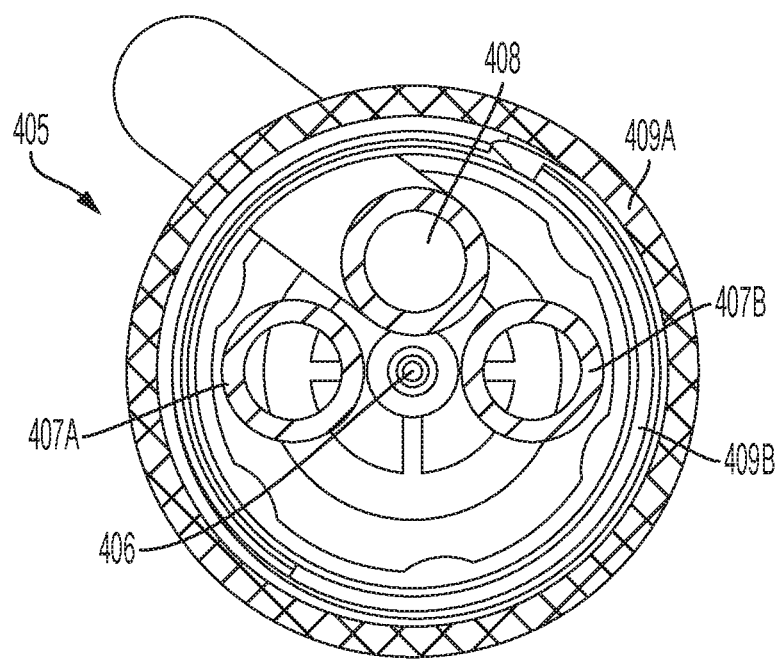
FIG. 5 schematically depicts a cross-section of an exemplary umbilical cord for use in the system of FIG. 1.

It will be appreciated that umbilical cords 405 for use in accordance with the present teachings can have a variety of configurations but generally define a conduit therethrough and are sufficiently flexible such that they can be maneuvered into a desired position. By way of example, as shown in FIG. 5, the exemplary umbilical cord 405 comprises a corrugated, flexible outer surface 409A (e.g., made of plastic) as well as a corrugated, inner shell 409B that is also flexible but can be made of a material (e.g., metal, stainless steel) that provides increased protection to the fibers and/or conduit extending through the conduit defined by the umbilical cord 405. For example, FIG. 5 depicts that an optical waveguide (e.g., optical 406) extends through the conduit for delivering EMR from the EMR sources to the applicators. Additionally, as discussed in detail below, one or more fluid pathways 407A,B can extend through the conduit, for example, for delivering cooling fluid to and returning cooling fluid from the applicator 300. Additionally, one or more signal cables 408 can be provided to enable electric communication between the housing 200 and the applicator 300 (e.g., including for transmitting signals generated by contact sensors of the applicators).

Figure 6:
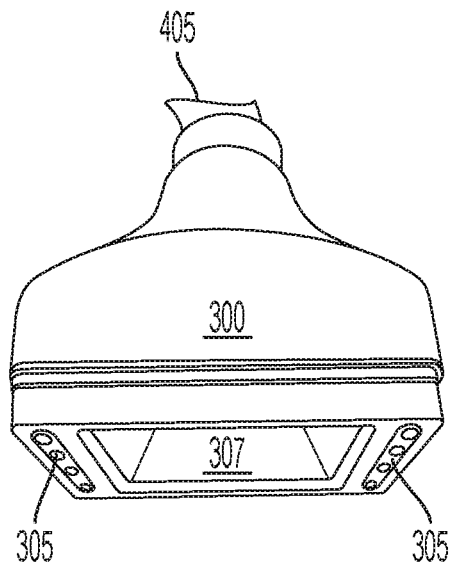
FIG. 6 depicts additional detail of the applicator of FIG. 1.

Referring now to FIG. 6, the exemplary applicator 300 of FIG. 1 is depicted in additional detail. As shown in FIG. 6, the applicator 300 (or treatment head) is coupled to the umbilical cord 405 (e.g., for delivery of the treatment energy) and includes a window having a skin-contacting surface 307 through which the treatment energy is transmitted from the applicator 300 to the treatment region (e.g., an optical window). The window can have a variety of configurations but generally comprises a material selected to provide good energy coupling with the skin when in contact therewith. By way of non-limiting example, an optical window can comprise glass or sapphire so as to provide good optical coupling with the skin when in contact therewith. It will also be appreciated that the contact surface 307 of the applicator 300 can have a variety of sizes and shapes (e.g., depending on the surface to be treated) including rectangular, square, triangular, circular, oval, ellipse, trapezoid, rhombus, pentagon, hexagon, octagon, or parallelogram, all by way of non-limiting example. As shown in FIG. 5, for example, the contact surface is rectangular, and can have a short side that ranges from about 1 cm to about 10 cm and a long side that range from about 2 cm to about 15 cm. In one exemplary embodiment, the short side measures 3 cm and the long side measures 5 cm. In another exemplary embodiment, the short side measures 4 cm and the long side measured 6 cm. In various aspects, the contact surface 307 can cover an area that ranges from about 2 $cm^2$ to about 150 $cm^2$, or about 15 $cm^2$, or about 24 $cm^2$.

With continued reference to FIG. 6, the applicator 300 also includes a plurality of contact sensors 305 (e.g., eight contact sensors) that ensure contact with the skin surface during treatment. In one embodiment, when there is incomplete contact or an absence of contact with one of the contact sensors 305 with the skin surface, the system takes action to avoid injury. For example, when incomplete contact or an absence of contact is detected, a controller in the system 100 will turn off the energy delivered to the applicator 300, thereby inhibiting radiation transmission through the skin contact surface 307 of the applicator 300. In another embodiment, when incomplete or an absence of contact is detected, by one or more of the contact sensors 305, the system 100 will lower the amount of energy (e.g., the intensity) delivered to the applicator 300 from the radiation source. Any of a number of suitable contact sensors 305 may be employed, for example, an electrical contact sensor (e.g., an electrical resistance sensor, an electrical impedance sensor, a capacitance sensor), a pressure contact sensor (e.g., a mechanical sensor). In various aspects, the use of contact sensors can be valuable in that it preserves eye safety. Suitable approaches to ensuring contact between the treatment head and the patient's skin and modified for use in accordance with methods and systems of the present teachings are disclosed, for example, in U.S. Pub. No. 20060149343 entitled "Cooling System For a Photocosmetic Device" and U.S. Pat. No. 6,653,618 entitled "Contact Detecting Method and Apparatus for an Optical Radiation Handpiece" issued Nov. 25, 2003, the teachings of which are incorporated by reference in their entireties.

As noted above, it may also be desirable to cool the skin-contacting surface 307 of the applicator 300 so as to cool the layers of the skin above the target region at depth. In some aspects, for example, as discussed above with reference to FIG. 5, one or more fluid pathways 407A, B can extend through the conduit, for example, for delivering cooling fluid to the applicator 300 for maintaining the skin-contacting surface and/or the skin surface at a desired temperature (e.g., to confine the hyperthermic treatment to the target tissue while keeping temperatures of dermal tissue above the targeted tissue at depth below injury threshold). Additionally, where the applicator surface is cooled, the use of contact sensors prevents unwanted heating (e.g., in the epidermal and/or dermal layer) due to lack of contact and/or incomplete contact between the skin surface and the cooled applicator surface. Suitable approaches to cooling the skin during photothermal treatment and modified for use in accordance with methods and systems of the present teachings are disclosed, for example, in U.S. Pat. No. 6,517,532 entitled "Light Energy Delivery Head" issued on Feb. 11, 2003; U.S. Pat. No. 6,663,620 entitled "Light Energy Deliver Head" issued on Dec. 16, 2003; U.S. Pat. No. 6,653,618 entitled "Contact Detecting Method and Apparatus for an Optical Radiation Handpiece" issued Nov. 25, 2003; U.S. Pat. No. 6,974,451 entitled "Light Energy Delivery Head" issued on Dec. 13, 2005; U.S. Pat. No. 6,976,985 entitled "Light Energy Delivery Head" issued on Dec. 30, 2005; U.S. Pat. No. 7,351,252 entitled "Method and Apparatus for Photothermal Treatment of Tissue at Depth" issued on Apr. 1, 2008; U.S. Pat. No. 7,763,016 entitled "Light Energy Delivery Head" issued on Jul. 27, 2010; U.S. Pat. No. 8,002,768 entitled "Light Energy Delivery Head" issued on Aug. 23, 2011; U.S. Pat. No. 8,915,948 entitled "Method and Apparatus for Photothermal Treatment of Tissue at Depth" issued on Dec. 23, 2014; U.S. Pub No. 20080103565 entitled "Method and Apparatus for Treatment of Cutaneous and Subcutaneous Conditions"; U.S. Pub. No. 20070213792 entitled "Treatment of Tissue Volume with Radiant Energy"; and U.S. Pub. No. 20140025033 entitled "Non-Invasive Fat Reduction by Hyperthermic Treatment," the teachings of which are incorporated by reference in their entireties.

As noted above, a self-retracting mechanism can be included with the umbilical cords that can assist in automatic retraction of the umbilical cord 405 and applicator 300 after a user has completed use of the applicator 300. In various related aspects, the applicator can weigh about 0.75 lbs, or from about 0.1 lb to about 10 lbs, or from about 0.25 lbs to about 5 lbs, or from about 0.5 lbs to about 1.5 lbs, by way of non-limiting example. Each applicator together with the umbilical cord can weigh about 3.5 lbs, or from about 0.75 lbs to about 15 lbs, or from about 1.5 lbs to about 7 lbs, or from about 2.5 lbs to about 5 lbs, by way of non-limiting example.

Figure 7A:
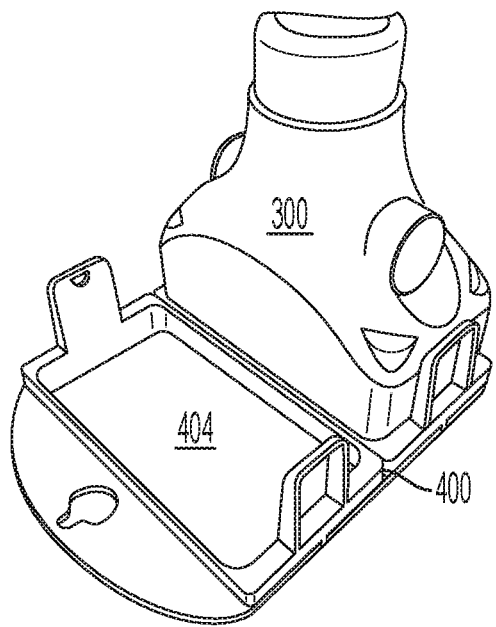
FIG. 7A-C depict the applicator of FIG. 6 coupled to an exemplary frame having at least two apertures that can be secured to the patient in accordance with various aspects of the present teachings.
Figure 7B:
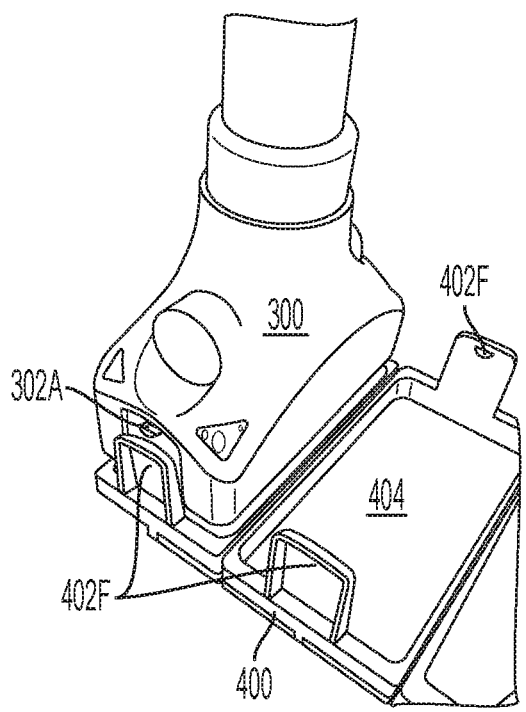
Figure 7C:
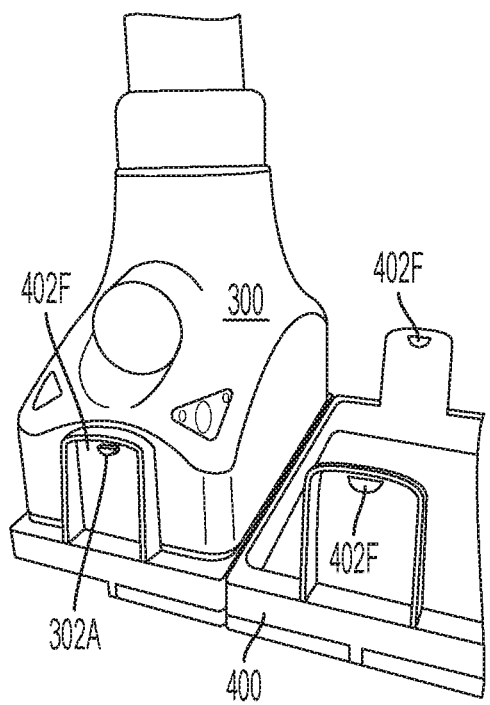

With reference now to FIGS. 7A-C, the applicator 300 is depicted as being removably attached to a frame, which as otherwise discussed herein can be secured to the patient to isolate a treatment region and/or help ensure contact between the skin-contacting surface 307 of the applicator 300 and a portion of the surface of the patient's skin tissue. As shown in FIG. 7A, the applicator 300 is mechanically attached to a frame 400 having an applicator surface and a skin contact surface, and defining two apertures 404 therebetween. FIG. 7A depicts how the applicator 300 is attached at the applicator surface to one of the two apertures 404 of frame 400, with the skin-contacting surface 307 of the applicator 300 (as shown in FIG. 6A) contacting the subject's skin through the aperture 404 of the frame 400. It will be appreciated that the applicator 300 and the frame 400 can be removably coupled using any coupling mechanism known in the art and modified in accordance with the present teachings. By way of example, FIGS. 7B and 7C depict an applicator 300 attaching to a frame 400 through the interaction between a male connector 302A on the applicator 300 that snap fits with a complementary female connector 402F on the applicator attachment side of the frame 400. Other exemplary fastening systems for removably coupling the applicator to the frame include tension fit, clamp, clip, hook and eye, clothespin, buckle, bungee, or zip tie, all by way of non-limiting example.

Figure 8:
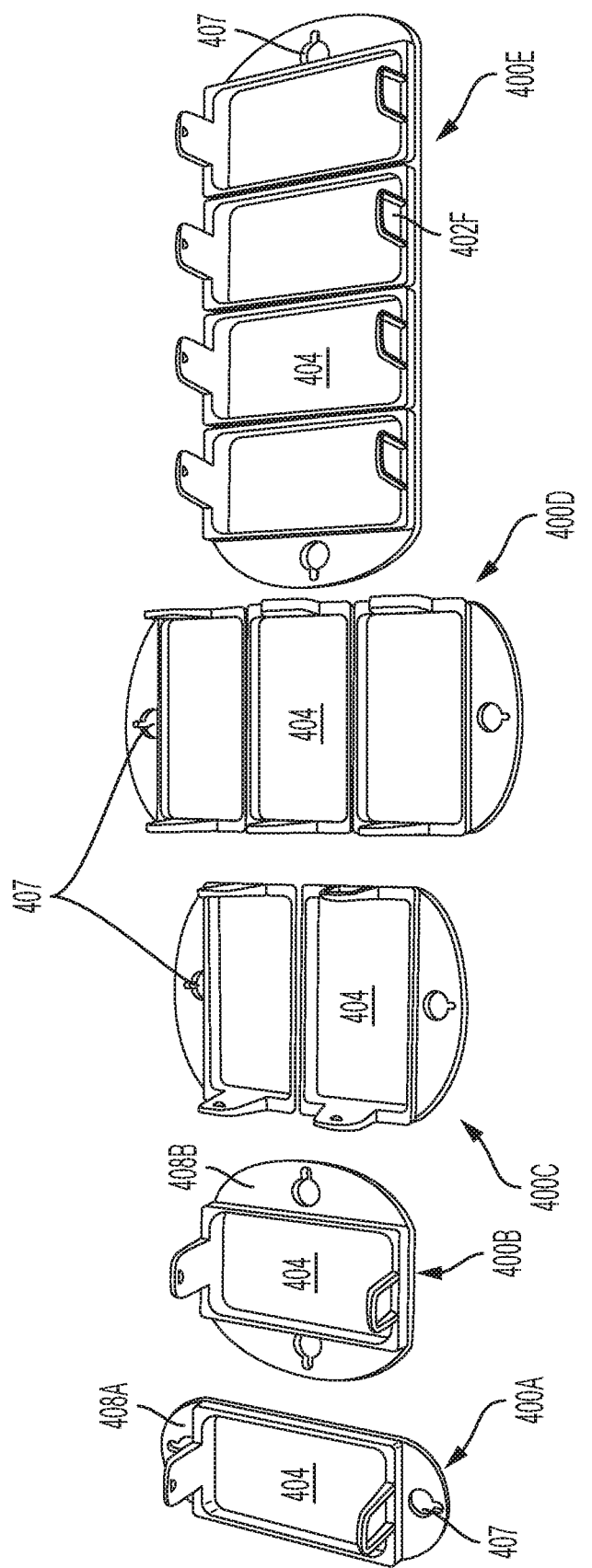
FIG. 8 depicts a variety of exemplary frame configurations that can be employed in the system of FIG. 1.

Additional details of exemplary frames in accordance with various aspects of the present teachings will now be discussed in more detail. With reference now to FIG. 8, a number of exemplary frames 400 that may be employed with the system of FIG. 1 are depicted. As shown in FIG. 8, frames 400A and 400B each have a single aperture 404, frame 400C has two apertures 404, frame 400D has three apertures 404, and frame 400E has four apertures 404, with each of the apertures 404 of the frames 400A-E being associated with a coupling mechanism (e.g., female connectors) on the applicator side of the frame for removably coupling with an applicator 300 (e.g., via snap fit connection). Additionally, as shown each of the frames 400A-E comprises tabs 408A/B that can be utilized to couple to a belt (e.g., through one or more belt loops 407 extending through the tabs 408A/B). It will be appreciated in light of the present teachings that the number of apertures 404, the shape of the apertures (e.g., rectangle, square, circle, hexagon, triangle, etc.), the layout of the apertures (linear pattern of apertures, brick pattern of apertures, vertically stacked column of apertures, or horizontally stacked row of apertures), and the size of the apertures can be customized for the desired treatment area. By way of example, where the region for treatment is contoured (e.g., around the waist of the subject) a frame having multiple hinged apertures may be used to enable treatment of the contour of the body area. In one embodiment, each aperture/applicator treats an area of from about 5 cm$^2$ to about 200 cm$^2$, or from about 10 cm$^2$ to about 150 cm$^2$, or from about 25 cm$^2$ to about 100 cm$^2$.

With reference now to FIGS. 9A-B, an exemplary frame 400 is shown in additional detail in which a hinge 441 is disposed between portions of frame 400 so as to adjust the angular orientation of the adjacent apertures and/or change their proximity to one another. FIG. 9B shows the skin contact side of the frame 400 and the regions where the apertures of the frame 400F are attached to one another via the plurality of hinges 441. For example, one or more hinges can attach adjacent frame portions to one another such that a first aperture of frame 400 is adjacent a second aperture of frame 400. In one embodiment, the hinges 441 are disposed on the skin contact side of the frame 400. The hinges 441 enable the frame 400 to follow the contour of the subject's body, e.g., by articulating the curvature of the area to be treated. In one embodiment, the hinge 441 can be sized to minimize separation between adjacent apertures so that when treatment occurs using a frame having multiple apertures, the treatment is relatively consistent in the overall treatment area despite the distance between adjacent apertures.

Figure 11:
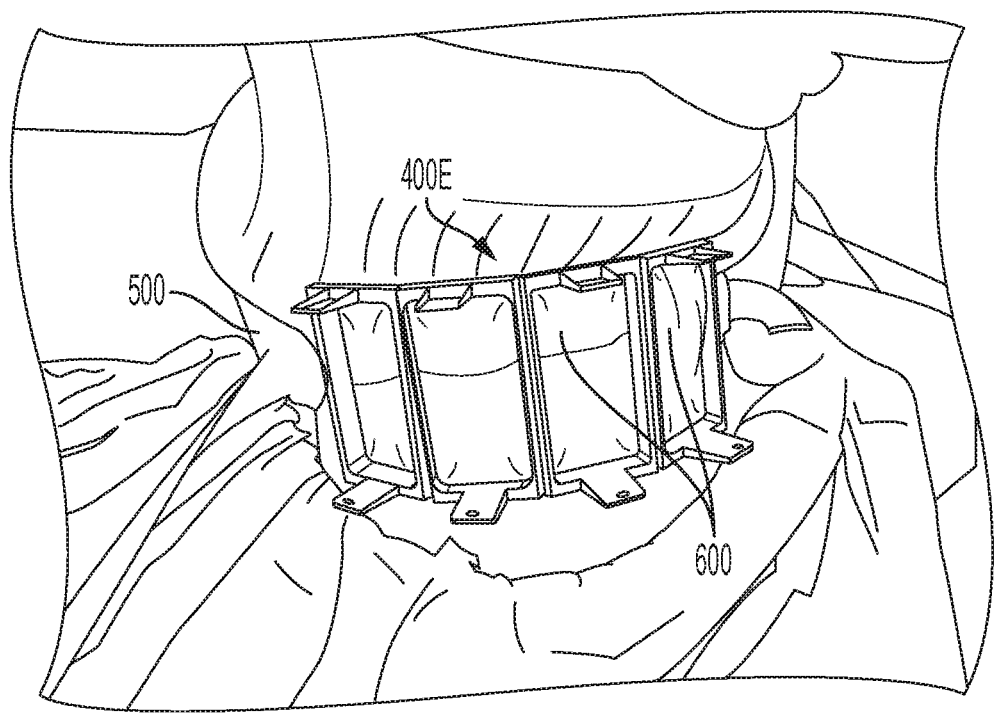
FIG. 11 depicts another exemplary frame having four apertures secured to a patient's body via a belt disposed about the patient's torso, thereby isolating the region(s) for treatment with the applicator(s).

As noted above, the frame can be secured to the patient, for example, prior to removably coupling the applicator to the frame. With reference now to FIG. 10, for example, the system 100 can include a belt 500 having an attachment mechanism (e.g., buckles 504) that attach to the frame 400D via belt loops 407 extending through the tabs 408B disposed on the frame 400D. FIG. 11, for example, depicts the belt 500 tightening a hinged frame 400E having four apertures around the contour of a subject's body, thereby isolating within the four apertures of the frame a skin surface of the treatment region(s) 600 that extend (e.g., bulge) into each aperture of the frame 400D.

Figure 12:
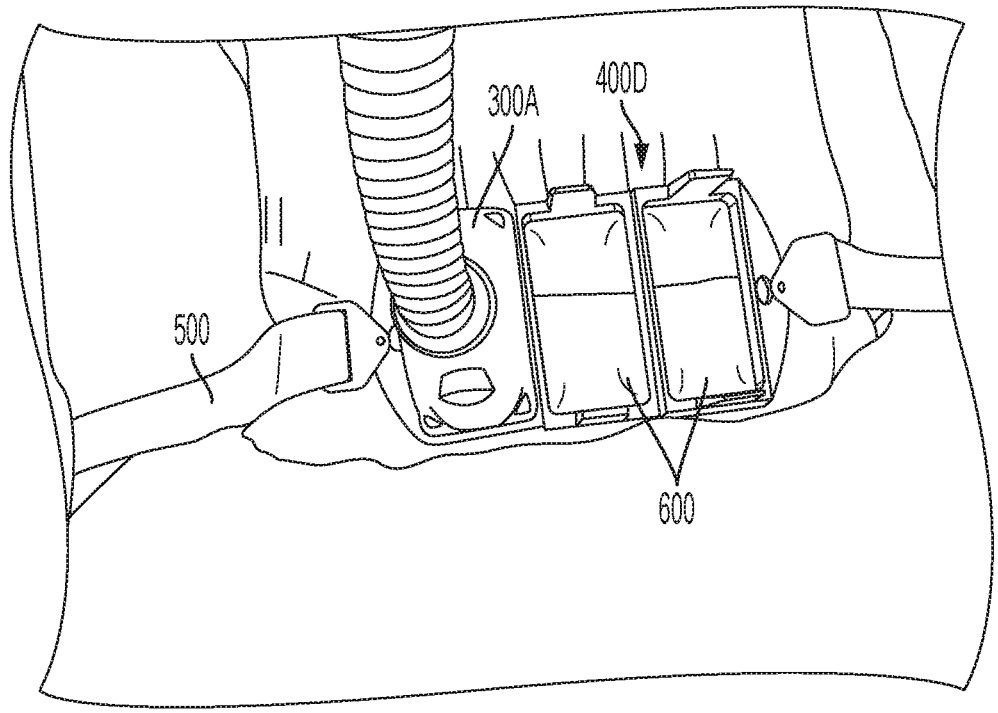
FIG. 12 depicts the exemplary frame of FIG. 10, secured to a patient's body via a belt disposed about the patient's torso, with one applicator being coupled to the frame so as to treat the treatment region within one of the three apertures.

FIG. 12 also shows a belt 500 tightening a hinged frame 400D having three apertures around the circumference of a subject's body thereby isolating the region(s) for treatment 600 with the applicator(s). As shown, the skin contact surface of the coupled applicator 300A is placed in contact with an isolated treatment region 600 having a bulge that is present in the aperture of the frame 400D. Referring still to FIG. 12, with the frame secured to the patient thusly, one or more applicators (e.g., up to four in the case of FIG. 11) can then be coupled to the frame 400D so that the skin-contacting surface 307 of each applicator 300 contacts the skin bulges 600 through each aperture 404 in the frame 400D. For example, the applicators 300 can be fastened to the frame 400D by snapping the male connectors on each applicator 300 with the complementary female connectors on the frame 400D associated with each aperture 404. The bulge of tissue through the aperture and the snap fit connection between the applicator and the frame 400D ensure contact of the skin-contacting surface of the applicator with the surface of the skin tissue 600 that has bulged through the aperture. Optionally, lotion can be disposed on the surface of the isolated region of skin tissue in the aperture 600 prior to coupling the applicator (e.g., via snap fit placement) to the frame and even prior to positioning the frame on the body area to be treated. Suitable lotions can include, for example, baby oil or Palomar® lux lotion. Optionally, contact sensors disposed on the skin contact side of the applicator(s) avoid treatment of the skin tissue when good contact is not in place. In this way, with a cooled applicator skin contact surface, proper cooling of the skin tissue by the applicator is provided and excessive heat treatment (e.g., burns) are avoided.

Figure 13A:
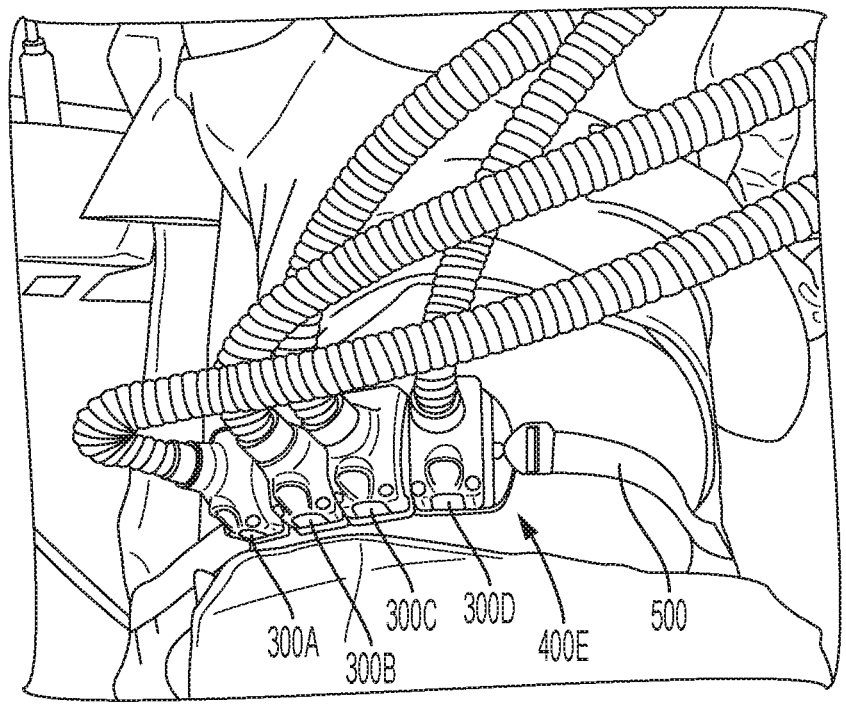
FIG. 13A depicts the exemplary frame of FIG. 11, secured to a patient's body via a belt disposed about the patient's torso, with four applicators being coupled to the frame so as to treat the treatment region within each of the frame's four apertures.

With reference now to FIG. 13A, treatment of a subject with the system shown in FIG. 1 is depicted in which four applicators 300A, 300B, 300C, and 300D are coupled to frame 400E. As shown, the frame 400E is tightened onto the subject via a belt 500 looped around the contours of subject's body so as to treat the regions of a body area isolated by the skin bulges present in the four apertures 404 of the frame 400E. In accordance with various aspects of the present teachings, the umbilical cords are looped through the arm and the brake mechanism that introduce the applicator to the frame with a tension level that ensures good contact between the skin contacting surface of the applicator and the subject's skin tissue. Each applicator is held by its respective umbilical and the umbilical is held from the arm of the system at a distance away from the energy source and at a height to help ensure good contact between the skin contacting surface of the applicator and the subject's skin tissue. Moreover, as discussed above, the applicator is attached to the frame by a removable coupling mechanism such as a snap fit engagement. The tissue isolated within and bulging in the apertures of the frame helps ensure that there is good contact between the skin contact surface of the applicator and the subject's skin tissue. Finally, optional lotion and optional contact sensors on the skin contact surface of the applicator enable the system to be used to treat tissue only when contact (e.g., good contact and/or full contact) is present between the applicator surface and the skin surface.

Figure 13B:
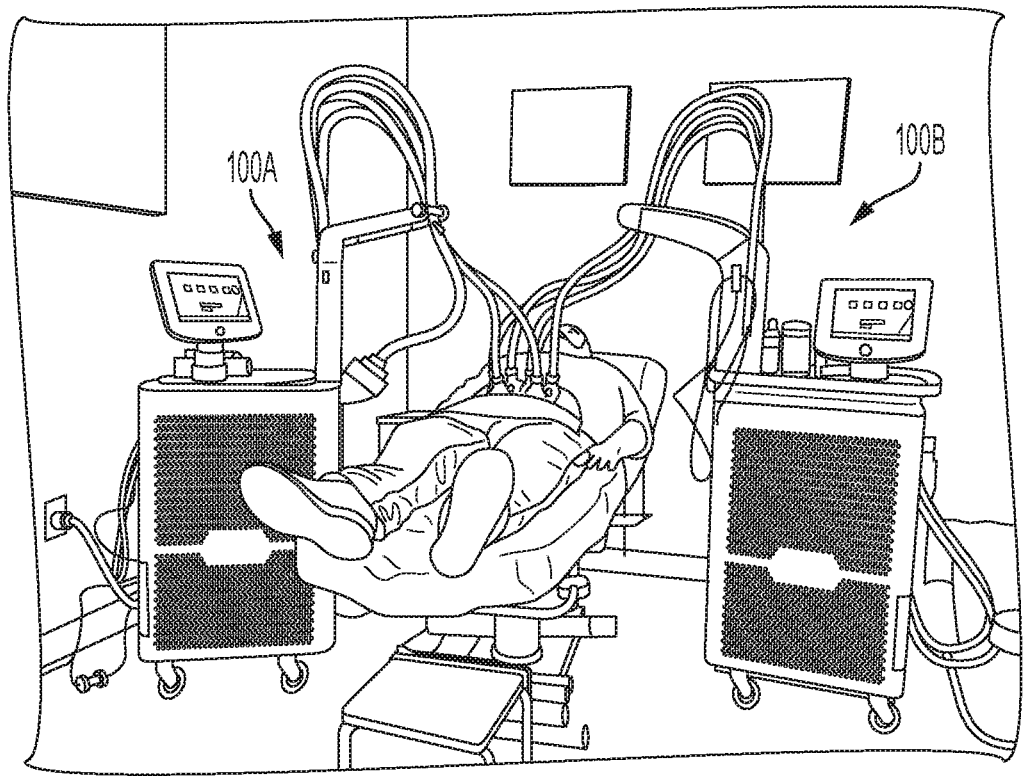
FIG. 13B depicts two exemplary systems shown in FIG. 1, with four applicators from one of the systems and two applicators from the other system being utilized to treat a body area isolated by six apertures of multiple frames that are tightened onto the subject via a belt looped around the subject's body.

As discussed otherwise herein, in this manner the subject can be "set up" for treatment by the practitioner and then require minimal to no additional direct contact with or attention from the practitioner until the treatment time is completed (e.g., for from about 5 minutes to about 2 hours) such that a safe, reliable, comfortable, non-invasive treatment of fat tissue can be achieved while requiring minimal practitioner time considering the length of time required to complete the treatment. FIG. 13B demonstrates how the subject can be positioned relative to the system 100 in accordance with various aspects of the present teachings. As shown, the subject can be disposed (e.g., lie) under the arm to enable the applicator attached to the umbilical to be aided by gravity from each umbilical that is held within the arm by opposing roller brakes. Referring still to FIG. 13B, the subject is treated with two separate systems 100A, 100B using four applicators from one system 100B and two applicators from the other system 100A to treat an abdominal body area isolated by six apertures of multiple frames. In one embodiment, for example, two or more separate frames can be attached to one another via a link (e.g., a "c" shaped loop, substantially "o" shaped loop that has an opening in it that enables frames to be linked together, or one or more snap fit connectors for connecting two or more frames to one another). The frames can be tightened onto the subject via a belt looped around the subject's body. Here regions of a body area isolated by the six separate skin bulges present in six apertures of at least two linked frames are tightened onto the subject via a belt looped around the contours of subject's body.

Additionally, the subject can be in the standing position when the area for treatment is isolated by the belt/frame combination and thereafter sit down or lie down for treatment with the system. By isolating the body area to be treated when the subject is in the position where the appearance of the body area is of most concern, the subject can be certain that his needs are being addressed and further the level of expertise to enable the treatment area to be isolated is lessened versus other treatment modalities. By isolating the treatment area in the frames while the subject is standing and prior to treatment, the subject can comfortably sit, recline, and or lay down during his treatment while knowing that the areas of concern are being addressed by the treatment.

It will be appreciated in light of the present teachings, that the systems and methods described herein can be customized or configured to treat specific treatment regions. For example, in addition to the abdominal treatments depicted in FIGS. 13A-B, a subject may have concern about other areas on the torso like the flanks, tissue below the bra area (on the front or back), also, areas of arms or legs, or about the appearance of fat and fullness in the face, chin, and neck area, by way of non-limiting examples. With specific reference to the submental area, the jowls, and the neck, these visible areas may be of concern to many people as they age and/or go through body weight changes. Small amounts of fat in the face, neck, and chin can make an otherwise fit person appear to carry more weight than the person actually carries.

Figure 14:
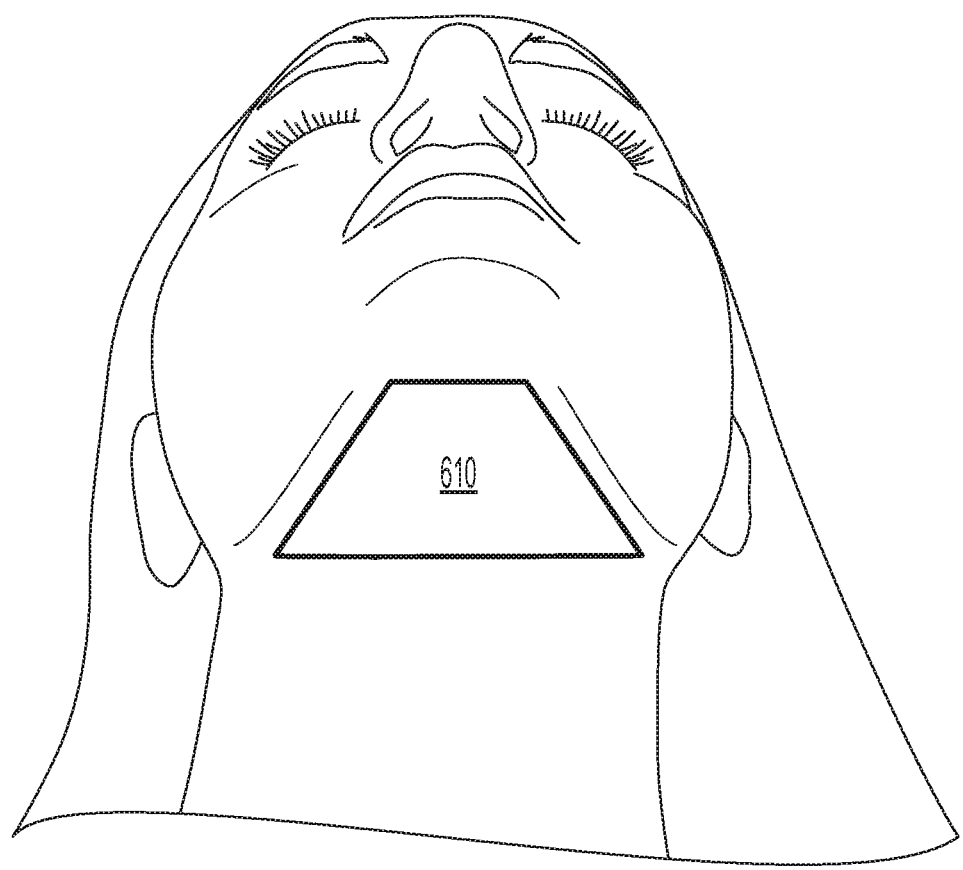
FIG. 14 depicts the submental treatment region.

FIG. 14 depicts the submental treatment region 610 of the face/neck area. The submental treatment region 610 is the region of the lower portion of the face/neck area that is located between the mandible down to the hyoid bone. Fat tissue can localize in the submental region leading to an appearance of submental fullness that a subject finds undesirable. Current treatment options range from liposuction, which is highly invasive, to a non-invasive approach that includes pressing a cooled applicator against the submental region. Other treatment options are desired.

In accordance with various aspects of the present teachings, one or more of the applicators 300 of the system 100 shown in FIG. 1 may be used to treat the undesired fat and fullness in the face, neck, and chin area. In one embodiment, for example, a standard frame 400 of the system 100 can be modified to adjust the irradiation footprint/size of the contact surface of the applicator so as to treat a relatively smaller submental or jowl region with a standard applicator contact surface. In one exemplary embodiment, each standard frame of the system can measure about 4.8 cm by about 9 cm (or about 43.2 $cm^2$) and each contact surface of the applicator can measure about 4 cm by about 6 cm (or about 24 $cm^2$). For example, in some embodiments disclosed herein, a mask portion can be coupled or attached to the frame so as to mask all or a portion of the irradiation footprint of the applicator's skin-contacting surface such that the irradiation surface of the contact surface is reduced (i.e., masked). For example, the mask portion can mask from about 0% to about 80% of the contact surface of the applicator, from about 15% to about 75% of the contact surface of the applicator, from about 25% to about 50% of the contact surface of the applicator, or from about 35% to about 45% of the contact surface of the applicator. In one exemplary embodiment, where the footprint of the applicator contact surface measures 24 $cm^2$, the effective treatment footprint of the contact surface can be reduced to a range from about 23.76 $cm^2$ to about 4.8 $cm^2$ once masked. The mask portion blocks at least a portion of the transmission from the contact surface of the applicator from reaching the subject's tissue. Each mask portion may have a fixed size and shape and multiple masks may be employed depending on the subject's treatment area, for example.

Alternatively, in some aspects, the mask portion can have an adjustable size and/or shape. The mask portion can have any of a number of shapes that may be selected depending on the area to be treated. The mask portion can have a shape that is selected from square, triangular, circular, oval, ellipse, trapezoid, rhombus, pentagon, hexagon, octagon, or parallelogram, for example.

In one exemplary embodiment, the mask portion is the shape of a rectangle that compliments the rectangular shape of the applicator contact surface, but the length of one or both sides of the rectangle is adjustable such that the size of the mask can be increased and the irradiation surface of the applicator contact surface may be reduced. In another embodiment, the mask portion is similar to a photography shutter than can be mechanically altered to increase the area covered by the mask portion to expose less and less of the applicator contact surface such that the irradiation surface is reduced.

Any number of suitable materials may be used to make the mask portion, such as, for example: aluminum, gold plated aluminum, ceramic, silver plated aluminum. In various aspects, it may be desirable to avoid the mask portion from heating up during the treatment of the treatment region. In such aspects, the mask portion can be actively cooled to prevent heat build-up in the mask portion from impacting the subject. Exemplary means for active cooling include, for example, using a thermoelectric cooler, air convection (fan), phase change material (ice), and a separate coolant circuit. Alternatively, the mask portion can be passively cooled, for example, by fins that help move heat away from the region of the mask portion. In such aspects, the fins would have sufficient area and thermal contact to dissipate heat to the surrounding ambient air or the frame of the fixture through conduction or convection. Ideally, the mask and any additional heat it accumulates from the energy source (e.g., EMR, laser, RF) can be wicked away by being in intimate thermal contact with the existing window (e.g., a sapphire surface) of the applicator, which is being actively cooled.

The one or more applicators can be held adjacent to the subject's face, neck, chin, or head by any of a number of approaches including by: strap/belt, gravity, positioning the patient's body area in a relatively comfortable position relative to the applicator (e.g., applicator placed on a table top and chin placed on top of the applicator). Suitable strap/belt systems used in orthodontia (e.g., head gear) and orthopedics (e.g., neck brace(s)) and modified in accordance with the present teachings may be employed to maintain the applicator's contact surface in desired contact with the area to be treated, for example, for treatment of the face, neck, or chin.

Figure 15A:
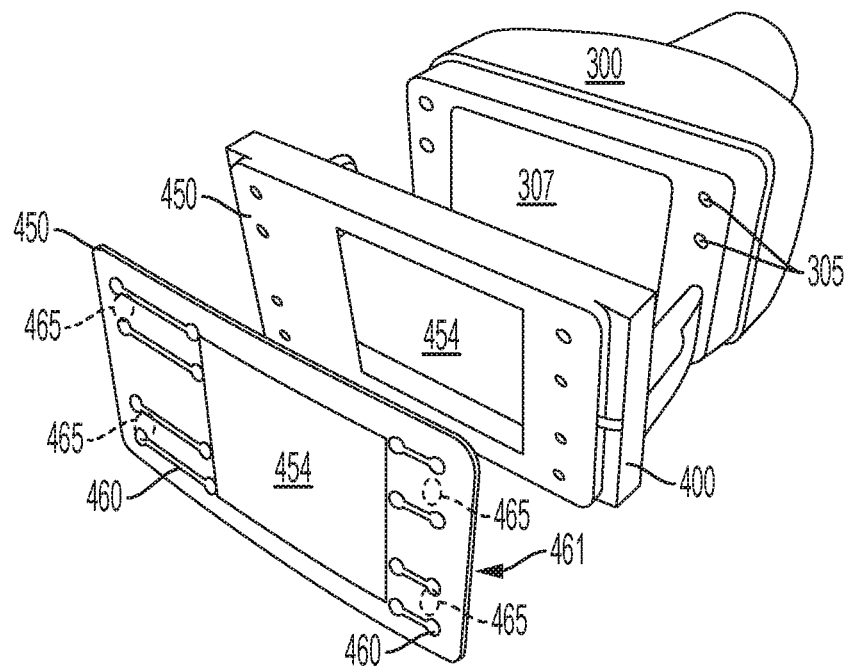
FIGS. 15A-B depict an exemplary applicator/frame/mask sub-assembly for use in the system of FIG. 1, in accordance with various aspects of the present teachings.

With reference now to FIG. 15A, an exemplary sub-assembly is shown with an applicator 300, a frame 400, and a mask portion 450 coupled to the frame 400 and occluding a portion of the frame's aperture 404. The unmasked portion 454 is in the shape a rectangle having a size reduced from the rectangle of the applicator's contact surface 307. Also shown is a contact sensor layer 461 that provides the same masking effect (modifies irradiation in the same size and shape) as the mask portion 450, with the contact sensor layer 461 of the mask enabling the contact sensors 305 of the applicator 300 to be effective in the presence of the mask 450. In this way, the contact detection capability as described above nonetheless remains available when the frame 400 is used in conjunction with the mask portion 450. The contact sensor layer 461 of the mask portion moves or offsets the effective contact sensors 460 to surround the now unmasked portion 454 so that active contact sensing and/or passive contact sensing can be utilized to ensure contact of the surface of the treatment region with the skin-contacting surface 307 exposed by the unmasked portion 454. Any of the uses of a masked portion disclosed herein may likewise employ a contact sensor layer 461 that provides an offset contact sensing capability, via offset contact sensors 460, that enables the contact sensors 305 present in the applicator to nonetheless be effective in the presence of the mask portion 450. The contact sensor layer 461 may optionally include one or more resistors 465 (shown in phantom) disposed between two adjacent effective contact sensors 460. FIG. 15A shows the presence of four resistors 465, though it is not necessary to have a resistor present between each pair of contact sensors. The one or more resistors 465 may be positioned on the side of the effective contact sensors 460 (the skin contacting side) or on the side of the contact sensor layer 461 that is adjacent the applicator surface. The resistor can be employed to provide a signal to the system such that the system will be treating a reduced area due to the presence of a mask 450. As a result of the resistor 465 signal, the treatment parameters may be adjusted in accordance with the reduction in irradiation surface area provided by the unmasked portion 454. Suitable system adjustments that can be made in response to the detection of the presence of a masked portion are, for example, increased cooling to cool the masked portion or reduction of cooling due to lesser surface area being treated. Other parameters that can be adjusted include, for example, the flux and/or the wavelength so as to treat the specific treatment area (e.g., submental area).

Figure 15B:
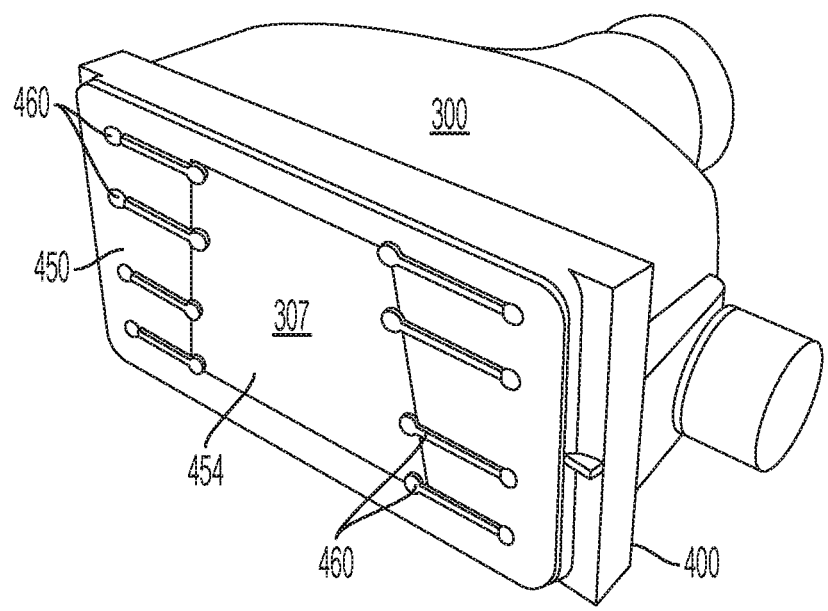

FIG. 15B shows a sub-assembly similar to FIG. 15A but differs in that the mask 450 defines an unmasked portion 454 having the shape of a trapezoid, where the unmasked portion 454 exposes from about 50% to about 80% of the irradiation surface of the applicator skin-contacting surface 307. As shown, the mask 450 includes four pairs (or eight total) of offset contact sensors 460 that effectively extend the applicator contact sensors present on the applicator surface similar to as is shown above in FIG. 15A and labeled 305.

Figure 32A:
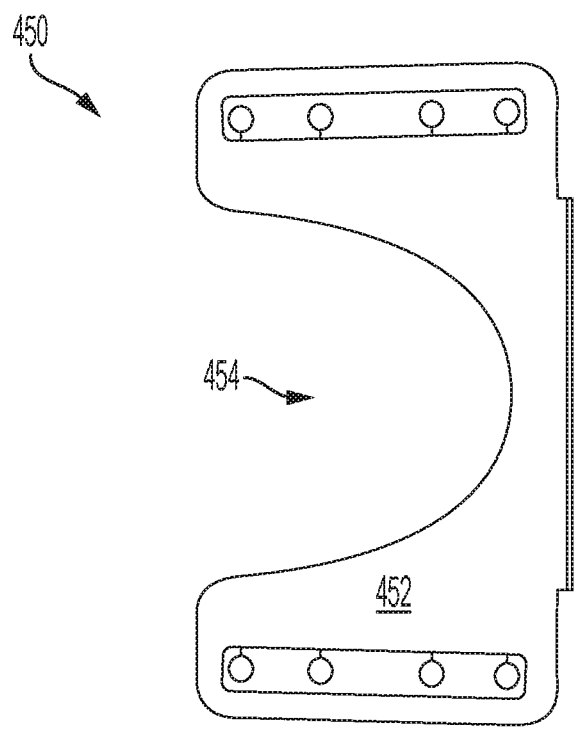
FIG. 32A depicts another exemplary mask for use in a applicator/frame/mask sub-assembly in accordance with various aspects of the present teachings.
Figure 32B:
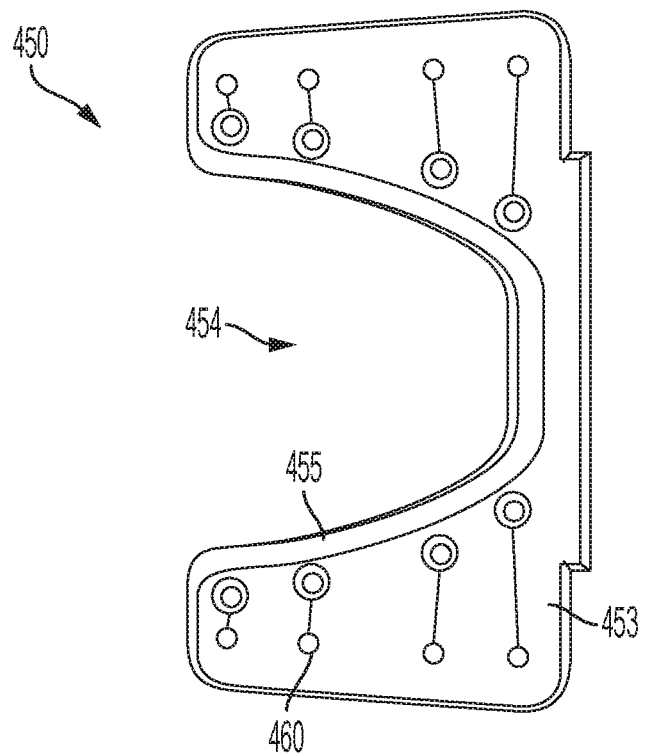
FIG. 32B depicts the patient-facing side of the exemplary mask of FIG. 32A.
Figure 33A:
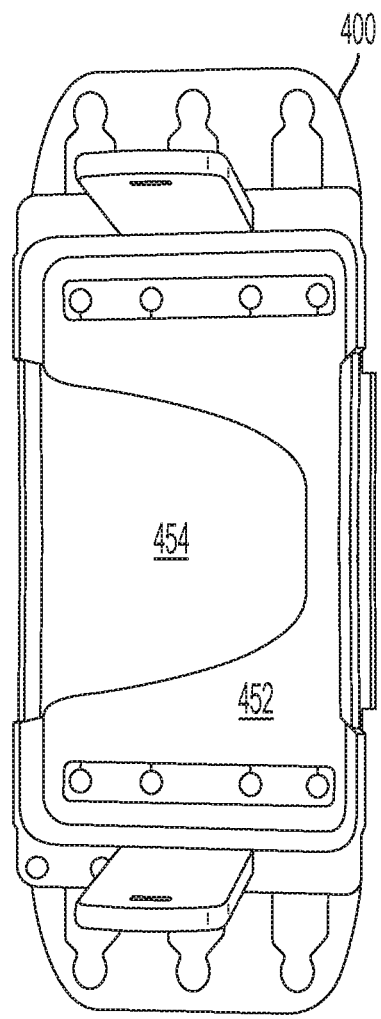
FIG. 33A depicts a portion of an exemplary applicator/frame/mask sub-assembly with the mask of FIG. 32A in accordance with various aspects of the present teachings.
Figure 33B:
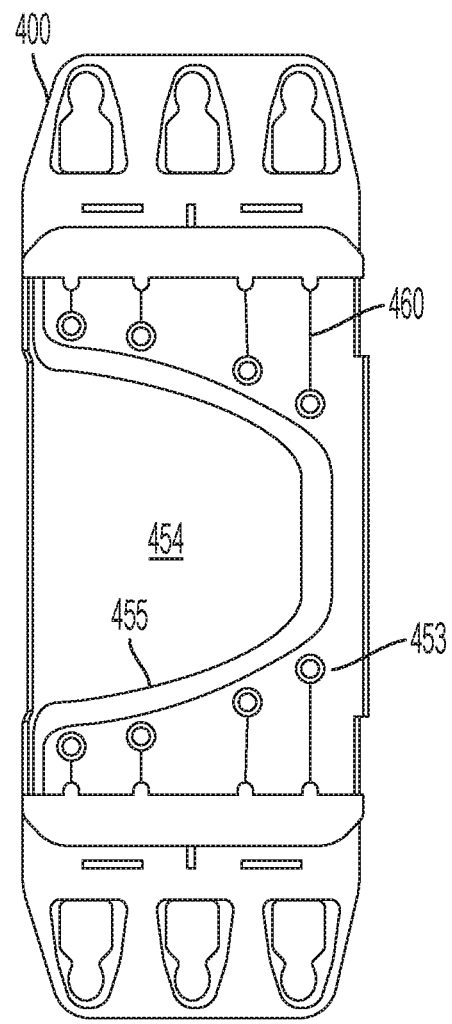
FIG. 33B depicts the patient-facing side of the exemplary applicator/frame/mask sub-assembly of FIG. 33A.

With reference now to FIGS. 32A-B and FIGS. 33A-B, another exemplary mask 450 in accordance with various aspects of the present teachings is depicted, with FIG. 32A representing the side of the mask 450 facing the applicator and FIG. 32B representing the side of the mask 450 configured to be in contact with the patient's skin. FIG. 33A depicts the mask 450 coupled to the frame 400 as seen from the applicator side, while FIG. 33B depicts the patient-facing side of the exemplary applicator/frame/mask sub-assembly. As shown in FIGS. 32A-B, the mask 450 generally comprises a substantially planar, conductive material 452 (e.g., gold, metal, gold coated metal) through which the treatment energy does not pass (or its transmission is attenuated) and which defines an unmasked portion 454 that is generally in the shape of a parabola that is smaller than the window of the applicator to which the mask 450 can be coupled. Though the generally parabolic shape of the unmasked portion 454 may be preferable for some treatments (e.g., treatment of the submental region), a person skilled in the art will appreciate masks 450 in accordance with the present teachings can define a variety of shapes and sizes of one or more unmasked portions 454 for controlling the application of energy to the treatment region. Though the mask 450 is shown and described above as generally having a planar patient-contacting surface, the mask can include other profiles (e.g., concavities). Nonetheless, in various aspects, a planar contact surface can be preferable to reduce/lessen air gaps between the mask and the treatment area, which can provide improved control of the application of the treatment energy. In various aspects, it will be further appreciated that an appropriate mask 450 can be selected to match the particular anatomy of a patient (e.g., size and shape of the unmasked portion), for example, and that the practitioner can selectively couple the mask to the frame as otherwise discussed herein. By way of non-limiting example, the mask 450 can be configured to be releasably retained within the frame 400 via snap-fit, compression fit, or tension fit such that the frame and mask 450 can be placed against the treatment region and the mask adjusted and/or replaced as necessary to provide for un-masking of the desired treatment region and/or masking of tissue that is not to be treated.

As noted above FIG. 32A represents the side of the mask 450 facing the applicator and FIG. 32B represents the side of the mask 450 configured to be in contact with the patient's skin. In accordance with various aspects of the present teachings, the mask 450 can include an indication of the proper orientation of the mask relative to the patient. By way of example, the mask 450 can be sided (e.g., via a fold) such that when the mask 450 is in placed in the frame and on the subject, the practitioner would know that the upper and lower face are properly oriented and/or the aperture is facing the proper direction. Though the mask 450 comprises a conductive material 452 (e.g., gold), in various aspects at least a portion of the patient-facing surface shown in FIG. 32B can be insulated, for example, with a polyamide coating 453 though it will be appreciated that a variety of insulating materials can be utilized. As shown in FIG. 32B, the contact sensors 460 can be embedded within the insulating coating and can communicate with contact sensing mechanism of the applicator as otherwise discussed herein. In addition, in some aspects as shown in FIG. 32B, a border 455 of the conductive mask 450 about the unmasked portion 454 may be left uncoated. It has been found that such an uncoated border having a width, e.g., between about 1 mm and about 10 mm wide, preferably from about 3 to about 6 mm wide, or from about 4 mm to about 5 mm wide) can provide for conductive cooling, while mitigating scattered edge effects of heating the treatment area through the aperture in the mask. For example, it was discovered that when the mask was entirely insulated on the patient facing side of the mask (e.g., there was no conductive border), scattered edge effects of the treatment energy was believed to pool in the tissue adjacent to these edges causing undesirable overheating. Though any number of suitable materials may be used to make the mask portion, such as aluminum, gold plated aluminum, ceramic, silver plated aluminum, all by way of non-limiting example, a gold conductive cooling border 455 may be preferred due to its biocompatibility, its conductivity, it ability to block the treatment energy, and its effectiveness in reducing the undesirable heating edge effects.

Figure 16A:
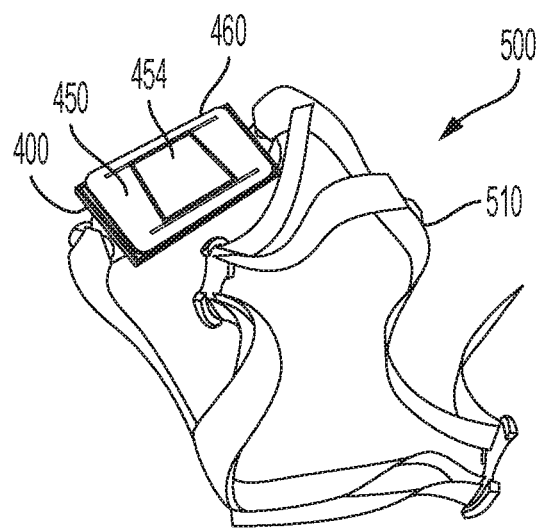
FIGS. 16A-D depict the exemplary applicator/frame/mask sub-assembly of FIGS. 15A-B further coupled to a belt for securing the sub-assembly to the patient's head for treatment of the submental region, in accordance with various aspects of the present teachings.
Figure 16B:
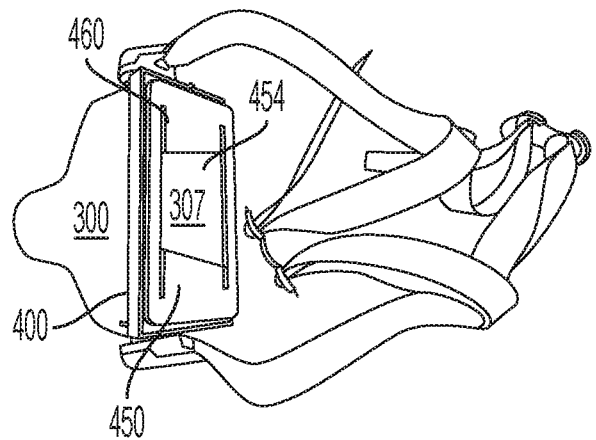
Figure 16C:
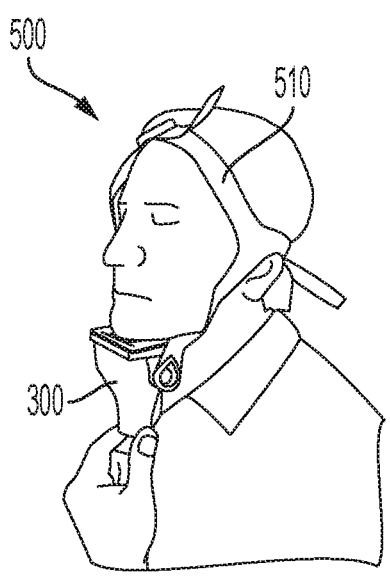
Figure 16D:
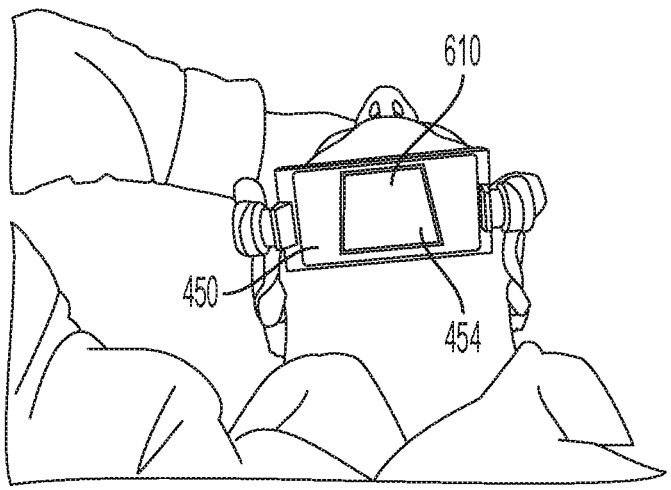

FIG. 16A shows a sub-assembly of frame 400, including a mask 450, having an unmasked portion 454 exposing a trapezoidal shape, with a plurality of offset contact sensors 460 together with a belt system 500, which is similar to a headgear used in orthodontia. FIG. 16B shows an assembly of the applicator 300 coupled with a frame (e.g., snap fit), including a mask 450 that masks all but a trapezoidal portion of the applicator contact surface 307, the unmasked portion 454 having a trapezoidal shape through which a portion of the applicator contact surface 307 is exposed. The assembly also includes one or more offset contact sensors 460, specifically, four offset contact sensors 460, all of which can be secured to the patient with a belt system. In various aspects, the unmasked portion 454 can expose from about 25% to about 80%, or about 50% of the irradiation surface of the applicator's skin-contacting surface 307. It will be appreciated that the amount of masking selected to cover the contact surface can depend, for example, on the shape and/or size of the subject's submental treatment area. FIGS. 16C-D depict the belt system 500 being used to place the masked frame 400 under the chin so as to isolate the submental tissue for treatment 610. As shown in FIG. 16C, the belt system 500 is tightened at the submental/chin region 610 from either end of the frame 400, the belt system 500 traveling up both sides of the jaw line, in front of both of the ears and branching off into a Y shape with one portion strapping around the front of the head 510 in the region of the forehead and the other portion strapping around the region of the back of the head and/or the neck. As best shown in FIG. 16D, the submental region 610 is exposed by the trapezoidal shape of the unmasked portion 454 and thereby treated by the applicator 300 when the skin-contacting surface 307 is in contact with the surface of the submental tissue extending into the trapezoidal shaped unmasked portion 454. In addition to utilizing the belt 500 to secure the frame/mask sub-assembly to the patient as shown in FIG. 16D, the subject of FIG. 16C is depicted as holding the applicator 300 in contact with the submental region 610. It will also be appreciated that in some embodiments, not shown, the subject can be lying down and gravity and/or propped pillows can help to maintain contact between the unmasked skin-contacting surfaces of the applicator and the skin surface. In still other embodiments, the subject can rest his chin against the applicator, which sits at a comfortable height on a table top (or in a construct similar to a slit lamp at an ophthalmologist office), the belt, optionally styled like a headgear used in orthodontia, helping to maintain proper placement of the applicator/frame assembly, with the pressure from the chin rests also helping to ensure good contact. As discussed otherwise herein, the applicator can be connected to the system via an umbilical (not shown).

Figure 17A:
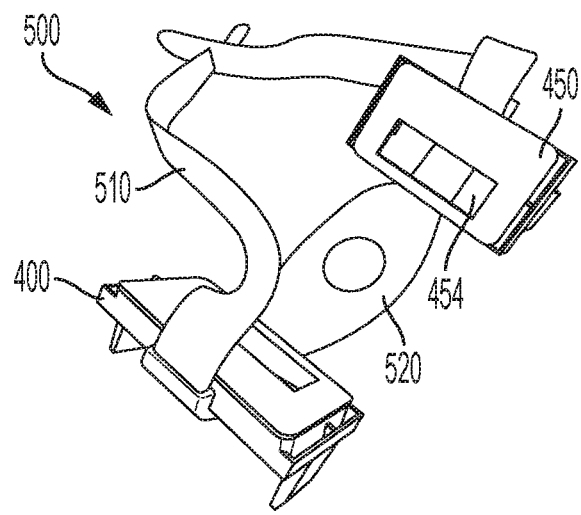
FIGS. 17A-C depict an exemplary sub-assembly having two applicators coupled to two masked frames, together with a belt system for attaching the two frames to one another and to secure the frames to the subject's body for treatment of the jowl's, in accordance with various aspects of the present teachings.
Figure 17B:
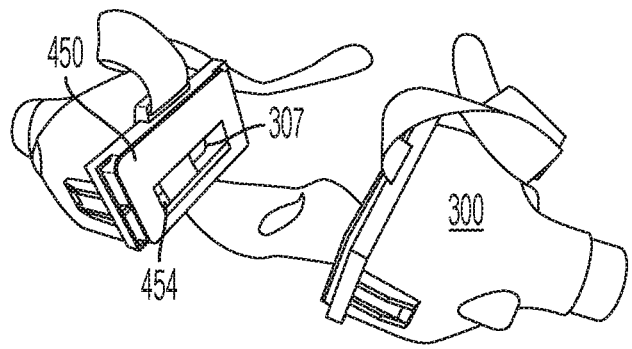
Figure 17C:
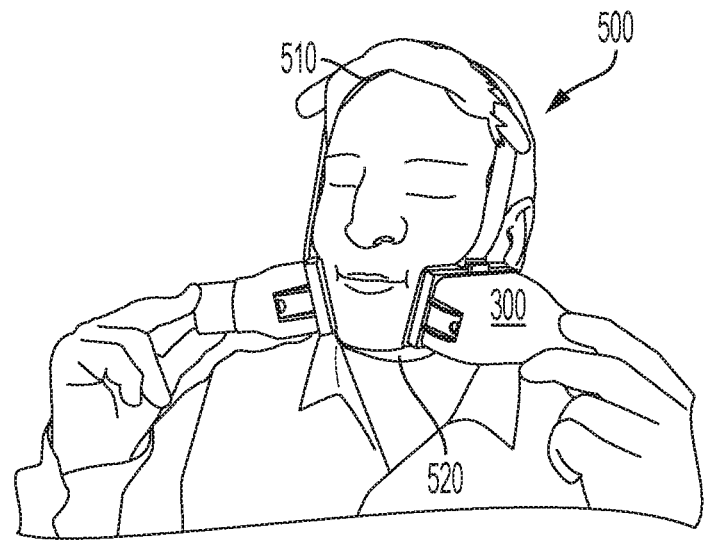

FIG. 17A shows a sub-assembly of two frames 400, each including a mask 450 defining an unmasked portion 454 having a rectangular shape, together with a belt system 500 having a chin strap 520 that attaches to the two frames 400. FIG. 17B depicts the sub-assembly of FIG. 17A with two applicators 300 connected to the frames 400, each frame 400 including an unmasked portion having a rectangular shape 454 surrounded by a masked portion and a belt system that attaches the two frames to one another and can be further joined together by two free ends to encircle and tighten around a subject's body portion. The unmasked rectangular shape 454 exposes a portion of the contact surface 307 of the applicator 300. FIG. 17C shows the sub-assembly shown in FIG. 17B with the two masked applicators each providing an unmasked rectangular portion disposed in contact with the two jowl areas of the face (left hand side and right hand side) above the jawline, with a chin strap 520 portion of the belt 500 between the two frames 400 being secured adjacent the chin, and the two free ends 510 encircling the head and connecting to one another just at the hairline above the forehead. The unmasked portion of each of the frames enables from about 20% to about 50% of the contact surface area of each of the applicators to be in contact with and treat a respective jowl portion. Here, in addition to the belt, the subject is holding the applicators in contact with the jowl area. In another embodiment, not shown, the subject can be lying down, with gravity and/or propped pillows helping to maintain contact between the unmasked contact surfaces of the applicators and the skin surface. As discussed otherwise herein, the applicator can be connected to the system via an umbilical (not shown).

Figure 18A:
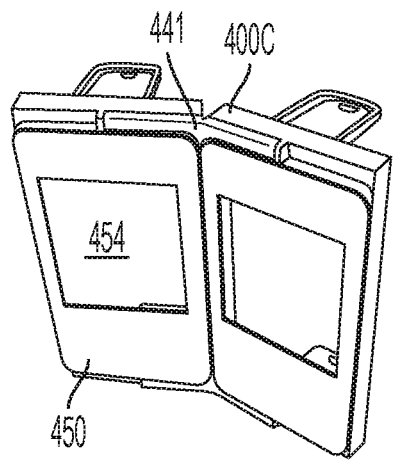
FIGS. 18A-E depict another exemplary sub-assembly having two applicators coupled to a masked frame, each of the applicators being associated with a separate aperture of the frame, and a belt system for securing the frame to the subject's body for treatment of the submental region, in accordance with various aspects of the present teachings.
Figure 18B:
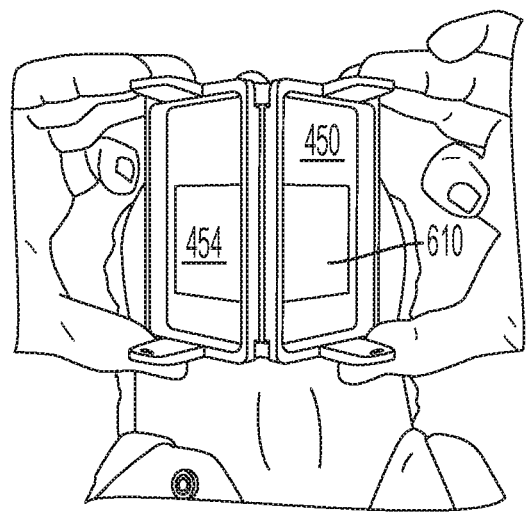
Figure 18C:
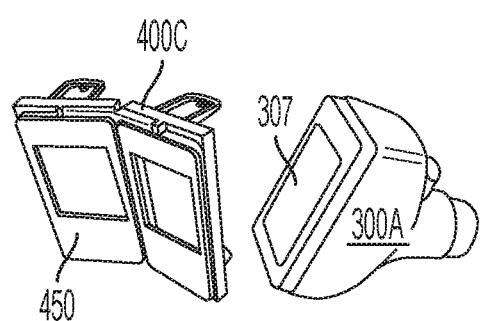
Figure 18D:
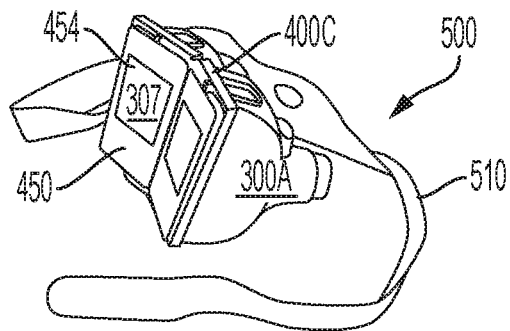
Figure 18E:
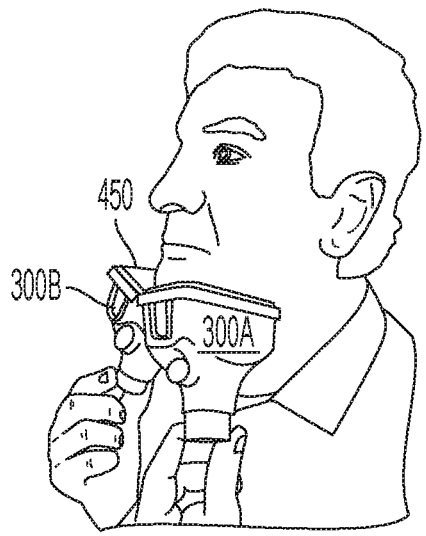

With reference now to FIGS. 18A-E, the sub-assembly includes two frames 400C (shown also in FIG. 8), with each frame 400C being coupled to a mask 450, where the unmasked portions 454 have a rectangular shape. The two frames 400C are connected to one another by a hinge 441. FIG. 18B shows the two masked hinged frames of FIG. 18A being held against the submental region 610, where the unmasked portions 454 reveal a left hand side and the right hand side of the submental region 610 with each side being isolated for tissue treatment by the unmasked portion 454 of the frame 400. The unmasked portion 454 enables irradiation from about 40% to about 75% of each of the applicator contact surfaces 307 to be delivered to the respective treatment areas (see FIG. 18C). FIG. 18C shows the two masked hinged frames of FIG. 18A together with an applicator 300A. FIG. 18D shows the two masked hinged frames of FIG. 18A snap fit attached to two applicators, revealing a substantially rectangular portion of the applicators' contact surfaces 307 through the unmasked portion 454 unobstructed by the mask 450. As discussed above, a belt 500 can also be attached to the frames 400C and can be used to secure the applicators 300 together with the frames about a portion of a subject's body (e.g., to surround the subject's head). FIG. 18E shows an assembly of two applicators 300A, 300B snap fit to the two masked hinged frames 400C of FIGS. 18A-D in contact with the submental region 610 of a subject. Here, the subject is holding the assemblies in contact with the submental region 610, though additionally or alternatively, the belt 500 shown in FIG. 18D may be used to secure the applicators to the submental region by encircling the belt around the head. In still another embodiment as otherwise discussed herein, the subject can rest his chin against the applicators, which can sit at a comfortable height on a table top, for example. As discussed above, the applicator can be connected to the system via an umbilical (not shown).

Figure 19A:
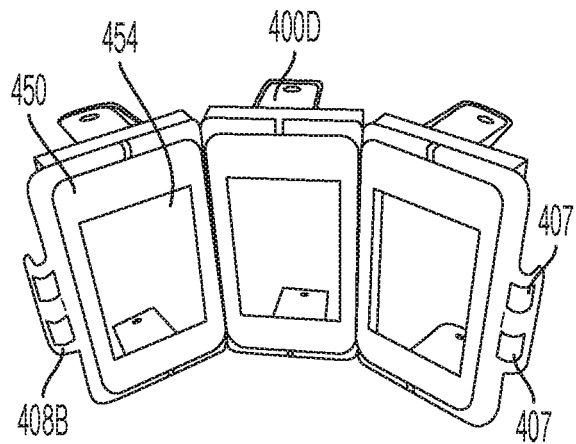
FIGS. 19A-D depict another exemplary sub-assembly having two applicators coupled to a masked, hinged frame, each of the applicators being associated with a separate aperture of the frame (with the middle aperture not being associated with an applicator), and a belt system for securing the frame to the subject's body for treatment of the neck region, in accordance with various aspects of the present teachings.
Figure 19B:
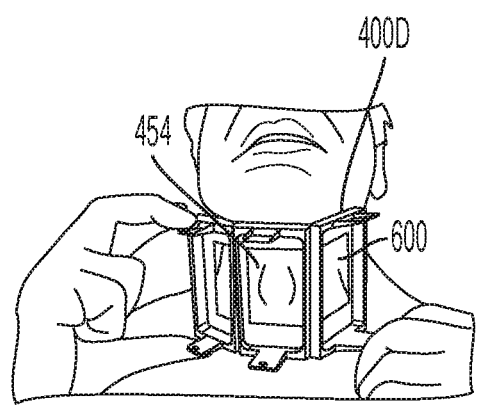
Figure 19C:
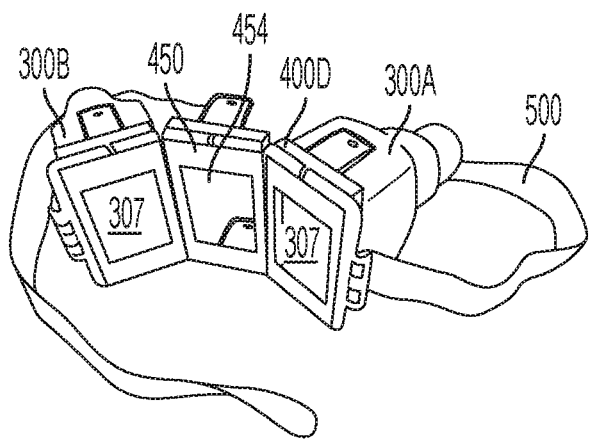

With reference now to FIGS. 19A-C, a hinged frame 400D defining three apertures 404 is coupled to a mask 450 defining three unmasked portions 454 having a rectangular shape. Tabs 408B include multiple belt loops 407 on either side of the frame 400D and enable the frame to be angled by using, for example, an upper belt loop on the left side and a lower belt loop on the right side. Though two belt loops 407 are shown on either side, it will be appreciated that a frame could employ any of a number of belt loops 407 so that the desired angling or positioning of the frame on the body can be achieved. For example, where six loops are present on a frame on the left side, the top loop can be used and on the right side the bottom loop can be used, this way desired positioning can be achieved for any of a number of body areas, not limited to the neck area, as shown here. In one embodiment, there is one belt loop on two sides of a frame. In another embodiment, more than one belt loop can be present on two sides of the frame.

Figure 19D:
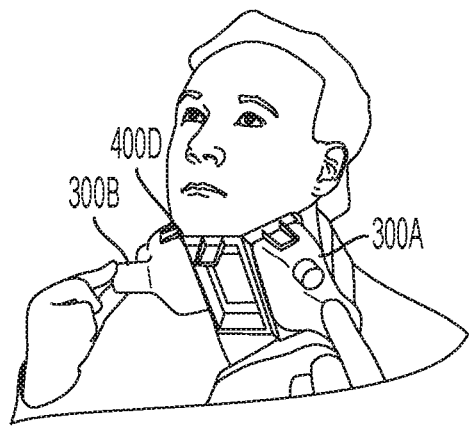

FIG. 19B shows the three masked hinged frames 400D of FIG. 19A held against the neck region, where the unmasked portion 454 reveal three portions of the neck region 600 that are isolated for tissue treatment. FIG. 19C shows the three masked, hinged frames of FIG. 19A snap fit attached to two applicators 300A, 300B revealing a substantially rectangular shaped contact surface 307 of each applicator through the unmasked portion 454 of two of the apertures of the frame 400D, with the center masked frame 400D not being attached to an applicator. As shown, a belt 500 is attached to the frame 400D to secure the applicators about a portion of a subject's body (e.g., about a subject's head). FIG. 19D shows an assembly of two applicators 300A and 300B snap fit to the frame 400D and associated with two of the three apertures as shown in FIGS. 19A-C, the attached applicators being in contact with the neck region, with the subject holding the two applicators 300A, 300B in contact with the neck region. In another embodiment, not shown, the belt 510 can be used to secure the applicators 300A, 300B and their masked frames 400D against the neck region by encircling the back of the neck. As discussed otherwise herein, the applicator can be connected to the system via an umbilical (not shown).

Figure 20A:
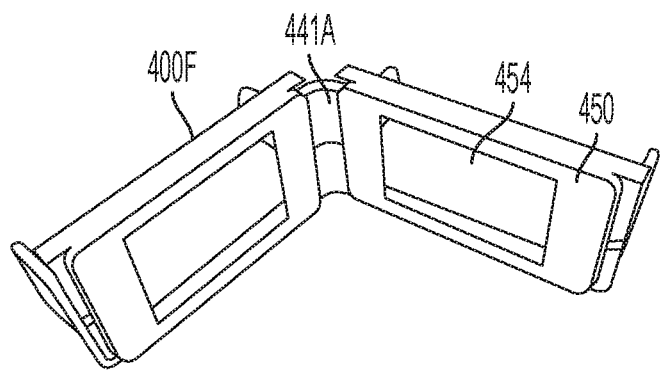
FIGS. 20A-C depict another exemplary sub-assembly for treating the neck region in accordance with various aspects of the present teachings, the sub-assembly having two applicators coupled to a masked, hinged frame, each of the applicators being associated with a separate aperture of the frame, and a belt system for securing the frame to the subject's body.
Figure 20B:
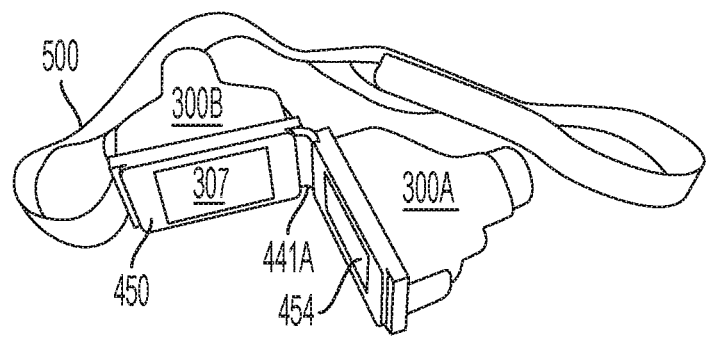
Figure 20C:
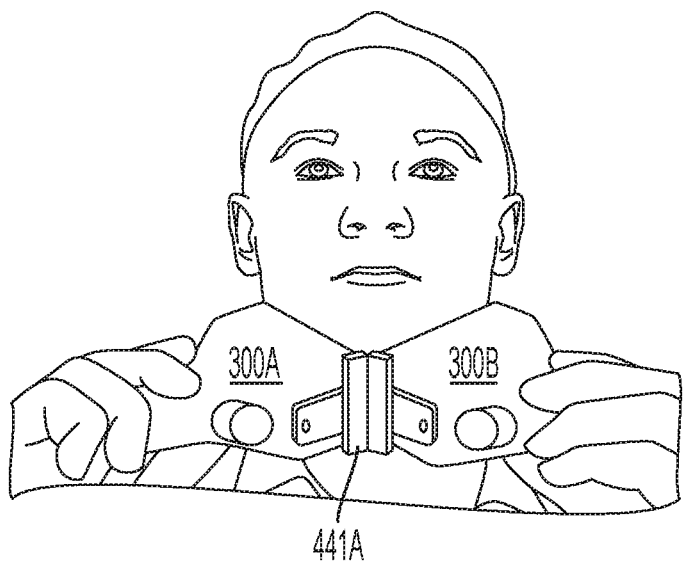

With reference now to FIGS. 20A-C, a masked frame 400F is depicted in which the unmasked portion 454 of the apertures of the frames 400F have a rectangular shape. The frames 400F are hinged 441A on their short side. FIG. 20B shows the masked, hinged frame 400F of FIG. 20A snap fit attached to the two applicators 300A, 300B, revealing a substantially rectangular portion of applicators' skin-contacting surface 307 through the unmasked portion 454. As shown, a belt 500 is also attached to the frame 400F and can be used to secure the applicators about a portion of a subject's body, e.g., about the face or neck. FIG. 20C shows the assembly of two applicators 300A, 300B, snap fit to rectangular the frame 400D that is hinged 441A on the short side, the unmasked portion 454 of the contact surface (shown in FIG. 20B) in contact with the neck region of a subject, with the subject holding the assemblies in contact with the neck region under the jawline. In another embodiment, not shown, the belt 500 can be used to secure the applicators against the neck region by encircling the back of the neck. In still another embodiment, the subject can be lying down on his back and the force of gravity, optionally together with propped pillows, can also help maintain contact between the unmasked portions of the applicator contact surface and the treatment area. As discussed otherwise herein, the applicator can be connected to the system via an umbilical (not shown).

Figure 21A:
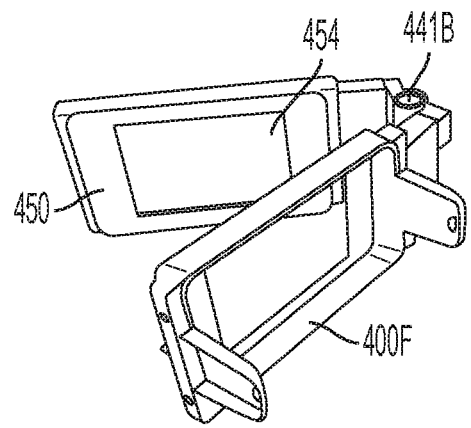
FIGS. 21A-C depict another exemplary sub-assembly for treating the neck region in accordance with various aspects of the present teachings, the sub-assembly having two applicators coupled to a masked, hinged frame, each of the applicators being associated with a separate aperture of the frame, and a belt system for securing the frame to the subject's body.
Figure 21B:
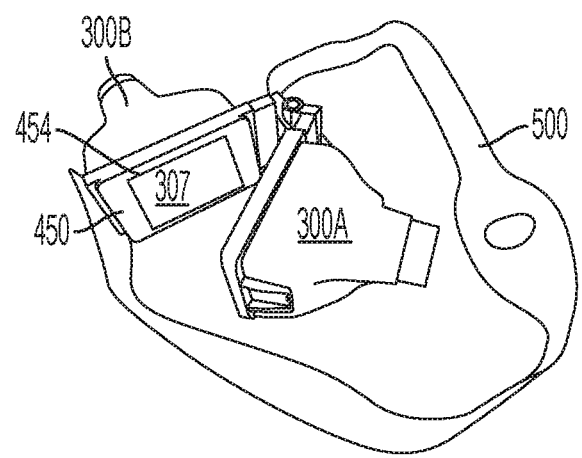
Figure 21C:
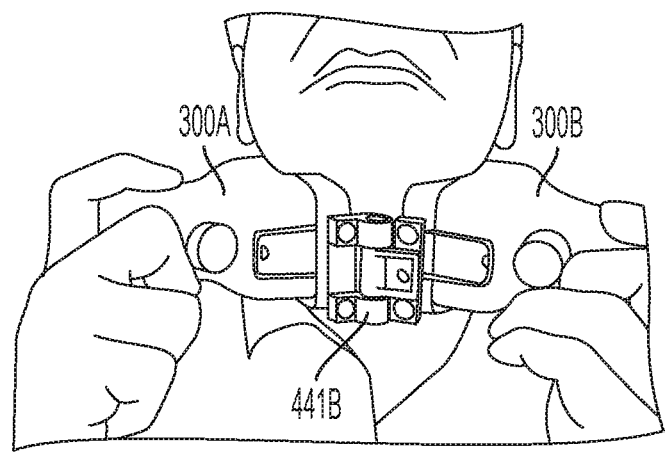

FIGS. 21A-C shows two masked frames 400F, where the unmasked portion 454 of the frame apertures 404 have a rectangular shape. The frames 400F are hinged 441B on their short side. The hinges 441B depicted in FIGS. 21A-C offer a greater range of motion and adjustability relative to the hinges 441A shown in FIGS. 20A-C, which can enable treatment of different areas and/or subjects having more fullness in the neck region. FIG. 21B shows the two masked, hinged frame 400F of FIG. 21A snap fit attached to the two applicators 300A, 300B revealing a substantially rectangular shaped surface of each applicator's skin contact surface 307 through the unmasked portion 454 of the mask 450. The unmasked portion 454 reveals from about 60% to about 80% of the available contact surface 307 of the applicator 300A, 300B. A belt 500 is attached to the frames 400F and can be used to secure the applicators together with the masked frames about a portion of a subject's body. FIG. 21C shows an assembly of two applicators 300A,B snap fit to the frame 400F of FIGS. 21A and 21B, with the skin-contacting surface 307 of the applicator being in contact with the isolated a portion of the isolated treatment region extending through the apertures 404 of the frame, with the subject holding the assemblies in contact with the neck region under the jawline. In another embodiment, not shown, the belt 500 can be used to secure the applicators against the neck region by encircling the back of the neck. In still another embodiment, the subject can be lying down on his back and the force of gravity, optionally together with propped pillows, can also help maintain contact between the unmasked portions of the applicator contact surface and the treatment area. As discussed otherwise herein, the applicator can be connected to the system via an umbilical (not shown).

Figure 22A:
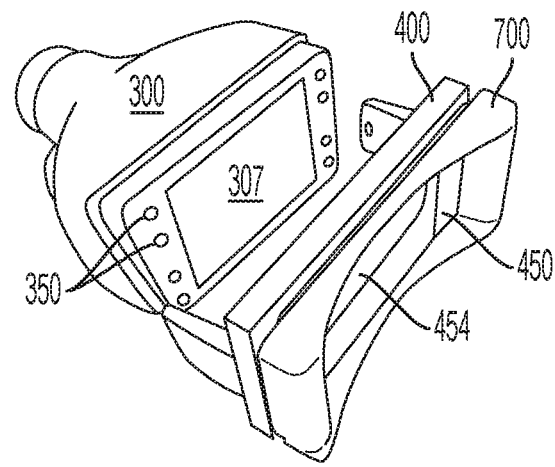
FIG. 22A-C depict another exemplary applicator/frame/mask sub-assembly for use in the system of FIG. 1 in which the skin-contacting surface of the frame is contoured (non-planar) to improve patient comfort during treatment of the submental region in accordance with various aspects of the present teachings.
Figure 22B:
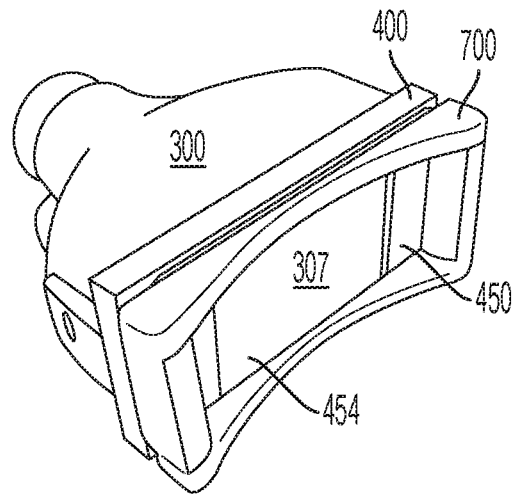
Figure 22C:
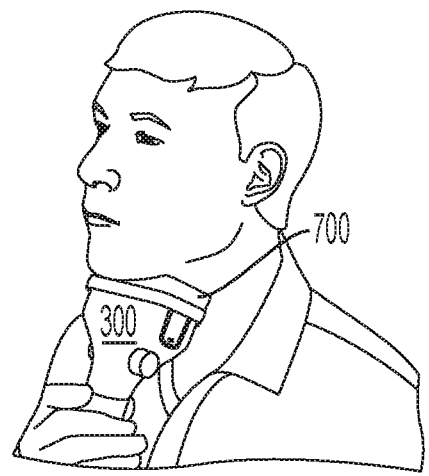

With reference now to FIGS. 22A-C, an applicator 300, a frame 400 including a mask 450 defining an unmasked portion 454, and a non-planar, contoured skin-contacting portion 700 is depicted. FIG. 22B shows the assembly of the applicator 300 attached to the frame 400, the mask 450 (defining the unmasked portion 454) and the contoured portion 700. FIG. 22C shows the sub-assembly of the applicator 300 removably attached to the masked frame 400, with the contoured portion 700 being held adjacent the submental treatment by the subject's hand. It will be appreciated that just as the contoured portion 700 can be shaped so as to form fit the submental convex region, other shapes are possible to match the contour of the treatment region. In some aspects, the contoured portion can limit the amount of contact enabled between the submental region and the applicator contact surface. In this way, a mask can, in some embodiments, be avoided. Rather, the access provided by the contoured portion can limit the effective irradiation surface of the contact surface 307 of the applicator 300.

In another embodiment, not shown, the subject can be lying down with gravity and/or propped pillows helping to maintain contact between the unmasked contact surfaces of the applicator and the skin surface. In still another embodiment, the subject can rest his chin against the applicator, which can sit at a comfortable height on a table top, for example, with the pressure from the chin resting against the applicator helping to ensure good contact for treatment. Optionally, a belt (not shown) from either side of the frame can encircle the subject's head to help maintain proper placement of the applicator/frame assembly, with the pressure from the chin rest also helping ensure good contact. In some embodiments, a contact sensor that may be offset from the applicator contact sensor can be coupled to the frame and/or the contoured portion 700 of the frame. As discussed otherwise herein, the applicator can be connected to the system via an umbilical (not shown).

Figure 23:
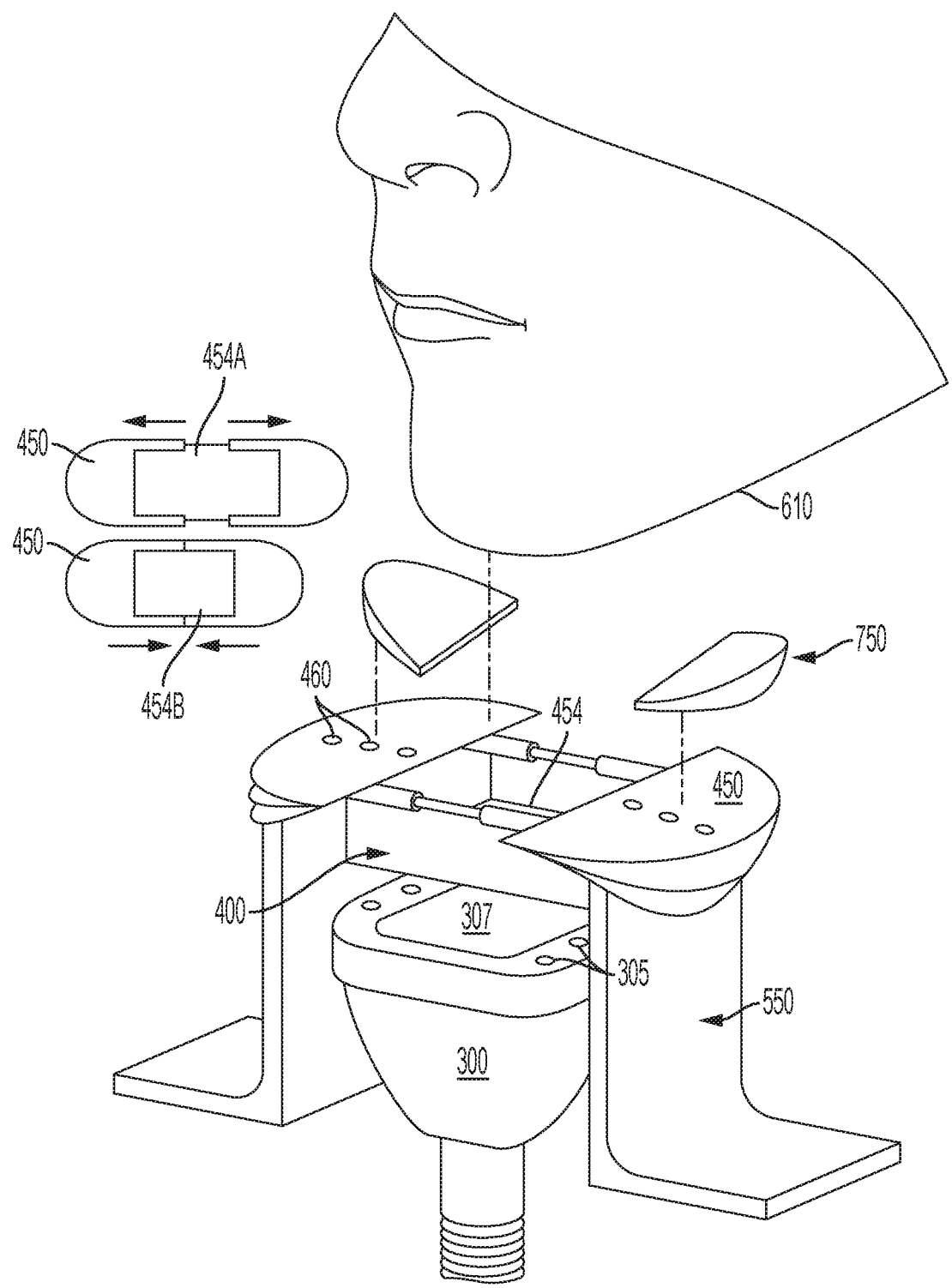
FIG. 23 schematically depicts another exemplary applicator/frame/mask sub-assembly in accordance with various aspects of the present teachings for treatment of the submental region.

With reference now to FIG. 23, an exemplary table top stand 550 is depicted having an adjustable mask 450 positioned thereon. The table-top stand 550 (e.g., similar to a slitlamp used in ophthalmology) can be positioned at a height comfortable to the subject. As shown, an applicator 300 can be positioned under a frame 400 on top of which sits the masked portion 450. As otherwise discussed herein, the applicator 300 can connect to the table top 550 stand via a coupling with frame 400 (e.g., a snap fit). As shown in inset, the size of the mask 450 can be adjustable to provide a relatively larger unmasked portion 454A or a relatively smaller unmasked portion 454B, thereby exposing more or less of the applicator contact surface 307 as desired. The adjustment of the masked portion relative to the unmasked portion can be adjusted depending, for example, on the size of the submental region of the subject to be treated.

As shown in FIG. 23, the subject can rest his submental area 610 on the adjusted mask portion 450 for treatment of the portion that remains unmasked 454. Optionally, chin rests 750 can be placed between the mask 450 and the subject's chin to ensure good positioning of the submental area on the skin-contacting surface 307. Optionally, the adjustable mask and/or the chin rests can include contact sensors (e.g., such as offset contact sensors 460 described above) that extend the effectiveness of the contact sensors 305 to ensure contact of the treatment region of with the contact surface 307 exposed by the unmasked portion 454. In some embodiments, the mask and/or the chin rests can provide a heat sink to ensure that the masked area is comfortable to the subject.

The systems of treatment of the face, neck, chin, and jaw disclosed herein may use the exemplary system 100 disclosed in association with FIG. 1. In some embodiments, one or more umbilical cords 405 may be temporarily freed or removed from the arm 420 and the brake mechanism 410 to enable a greater range of motion of the applicator(s) 300 and the umbilical cord(s) 400 for treatment in accordance with any of the applications disclosed in association with FIGS. 14-23.

Figure 24A:
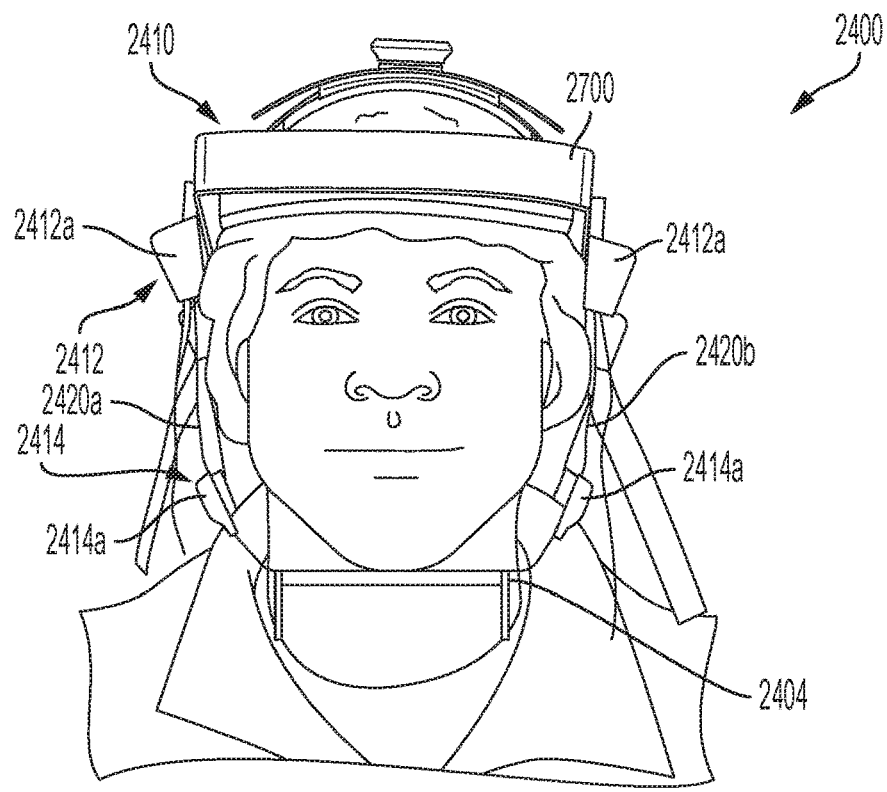
FIG. 24A shows a front view of an exemplary harness secured to a patient's head in accordance with various aspects of the present teachings.
Figure 24B:
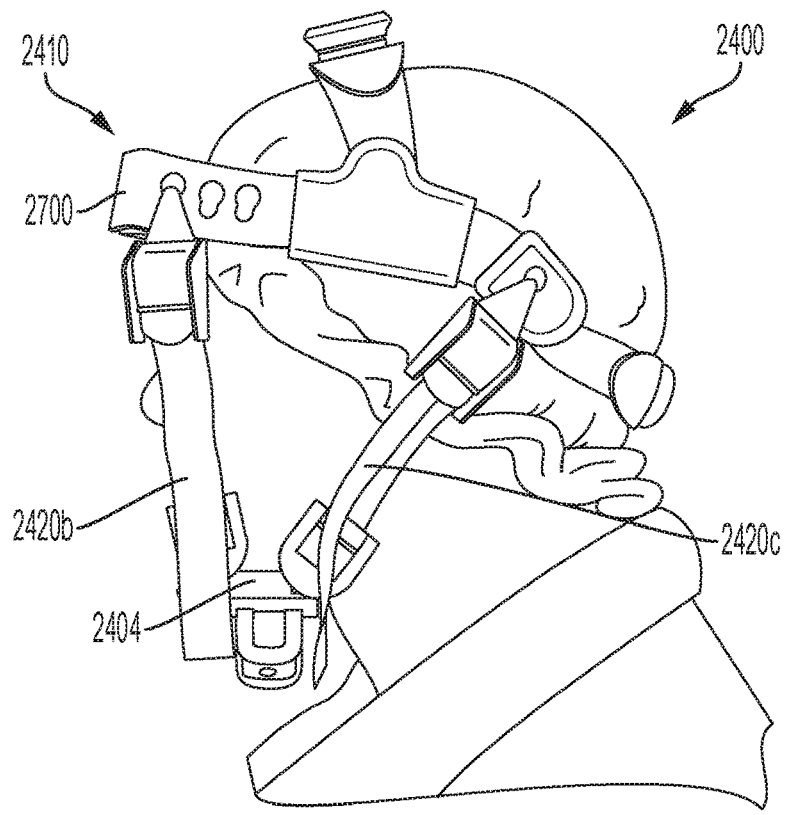
FIG. 24B shows a side view of the exemplary harness of FIG. 24A.
Figure 24C:
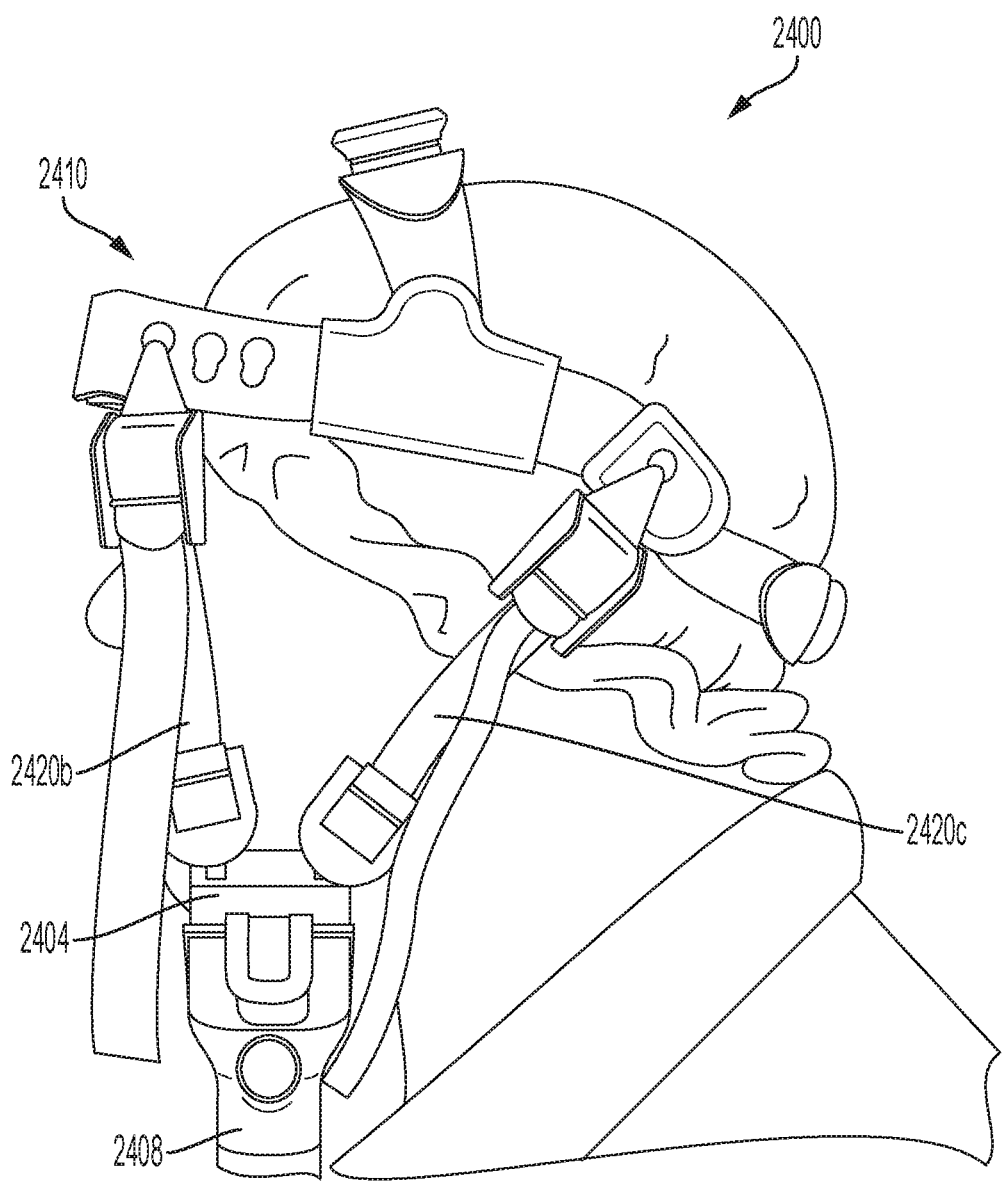
FIG. 24C shows a side view of the exemplary harness of FIG. 24A that is coupled to an exemplary applicator in accordance with various aspects of the present teachings.
Figure 24D:
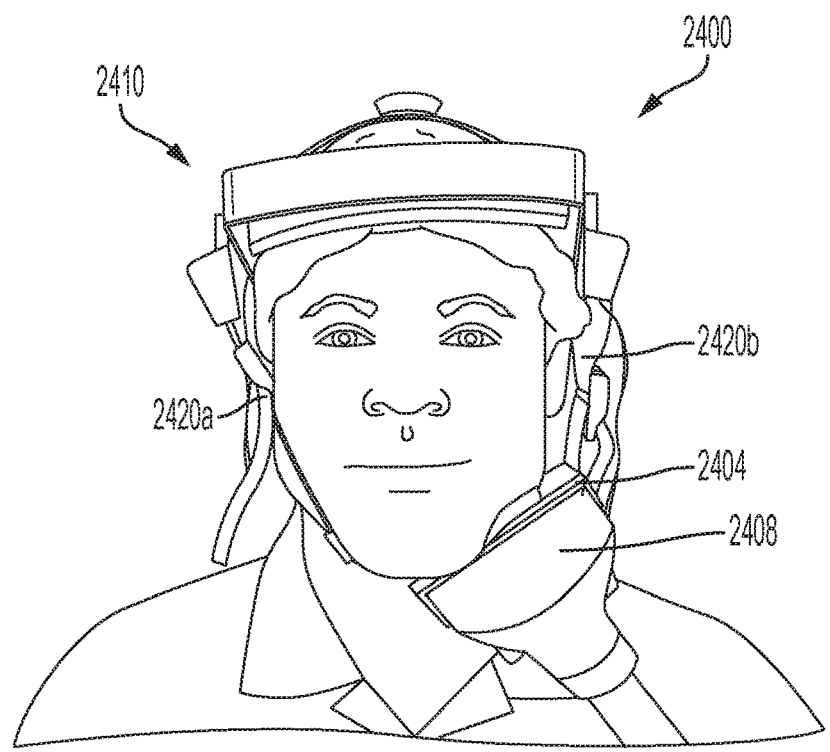
FIG. 24D shows a front view of the exemplary harness of FIG. 24A secured to a patient's head for treatment of a jowl in accordance with various aspects of the present teachings.
Figure 24E:
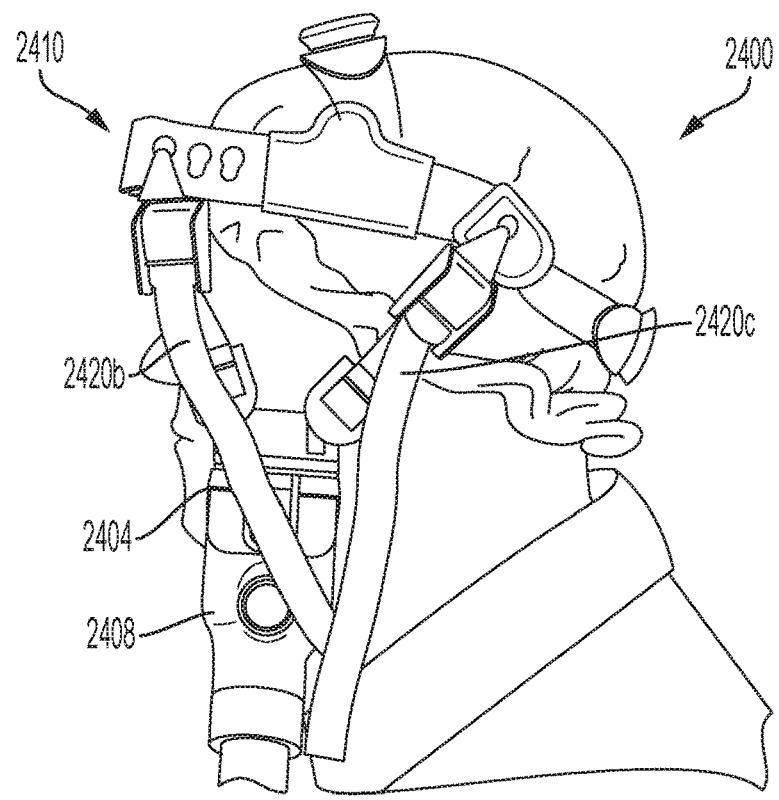
FIG. 24E shows a side view of FIG. 24D.
Figure 25:
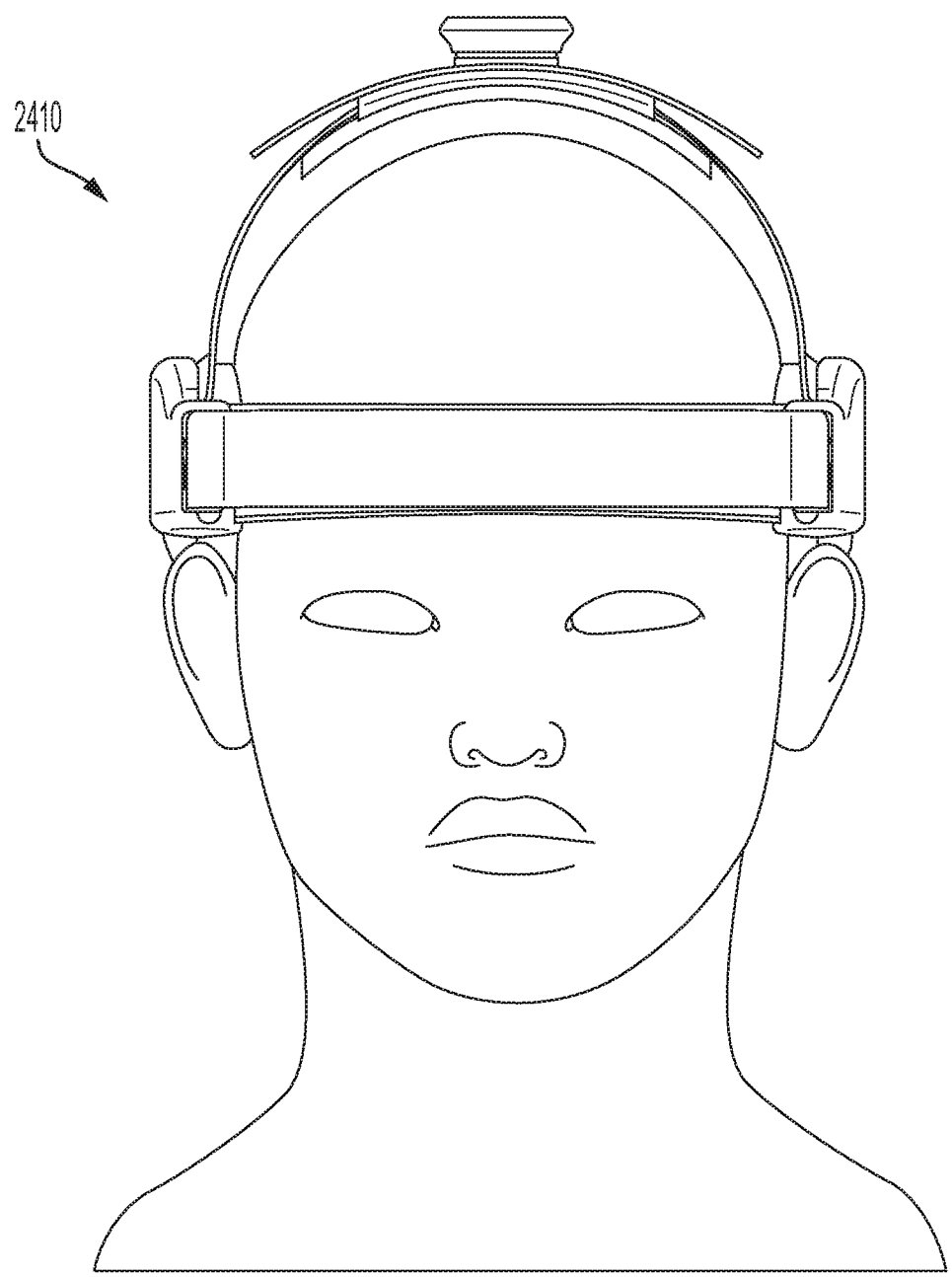
FIG. 25 shows a front view of a schematic representation of an exemplary harness placed on a human model's head in accordance with various aspects of the present teachings.

As noted above, in accordance with various aspects of the present teachings, a harness can be provided to facilitate treatment of particular portions of a patient's body including of the head or neck region, for example, by improving patient comfort as the treatment is being applied, to ensure effective contact with the treatment region for effective coupling of the treatment energy into the skin, and/or to improve patient safety. With reference now to FIGS. 24-31, another exemplary harness for use in the treatment of a subject's head or neck region (e.g., the submental region, the cheeks, the portion of the cheek at or below the cheek bones, and the jowls) will now be described. As shown in FIG. 24A-C, an exemplary harness 2400 in accordance with various aspects of the present teachings can be removably secured on a patient's head. As discussed otherwise herein, the harness 2400 can be configured to be coupled to a treatment applicator (e.g., applicator 2408 depicted in FIG. 24C) so as to maintain the treatment applicator 2408 in a fixed position relative to the treatment region during the course of the treatment. As shown in FIGS. 24A-C and as will be discussed in more detail below, the exemplary harness 2400 generally comprises headgear 2410 that is configured to be secured to the patient's head that can be coupled to a frame 2404 via one or more connectors 2420 such that the frame 2404 can be maintained against the submental region. As will be appreciated by a person skilled in the art in light of the present teachings, the exemplary harness 2400 enables treatments to be performed by having the practitioner set-up the headgear 2410, frame 2404, and applicator 2408, and start the treatment, thereafter allowing the treatment to proceed without the continued presence of the practitioner and having the patient standing, sitting, or lying. With reference now to FIG. 24D-E, it can be seen that the exemplary harness 2400 can be reconfigured to treat additional regions of the subject's head. As shown in FIG. 24D-E, the exemplary harness 2400 is removably secured on a patient's head and can maintain the treatment applicator 2408 in a fixed position relative to the patient's jowl treatment region during the course of the treatment. As discussed otherwise herein, the coupling of the connectors 2420 with the headgear 2410 and/or their length can be adjusted to accommodate particular treatment regions.

Figure 26:
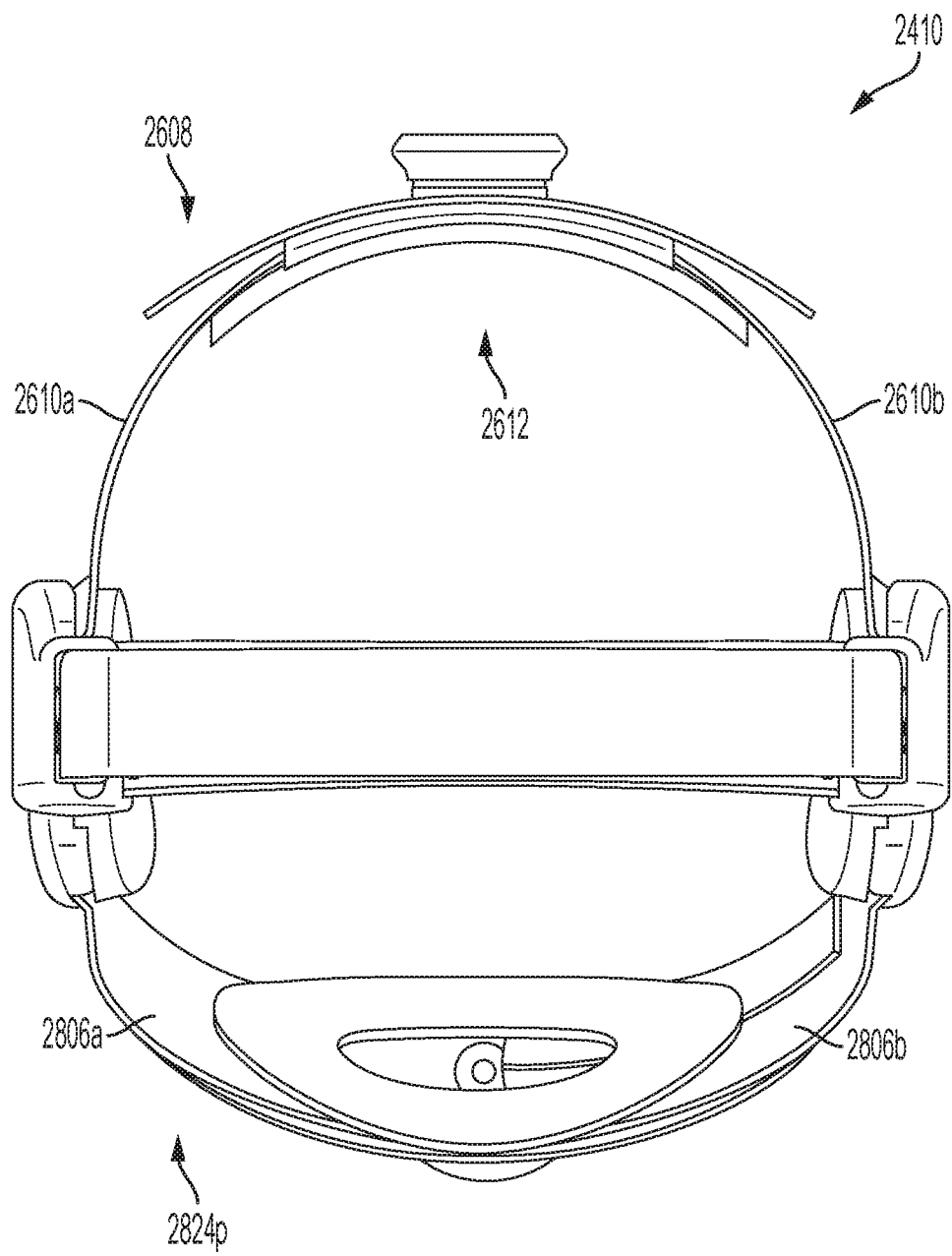
FIG. 26 shows a front view of the exemplary harness of FIG. 25.
Figure 30:
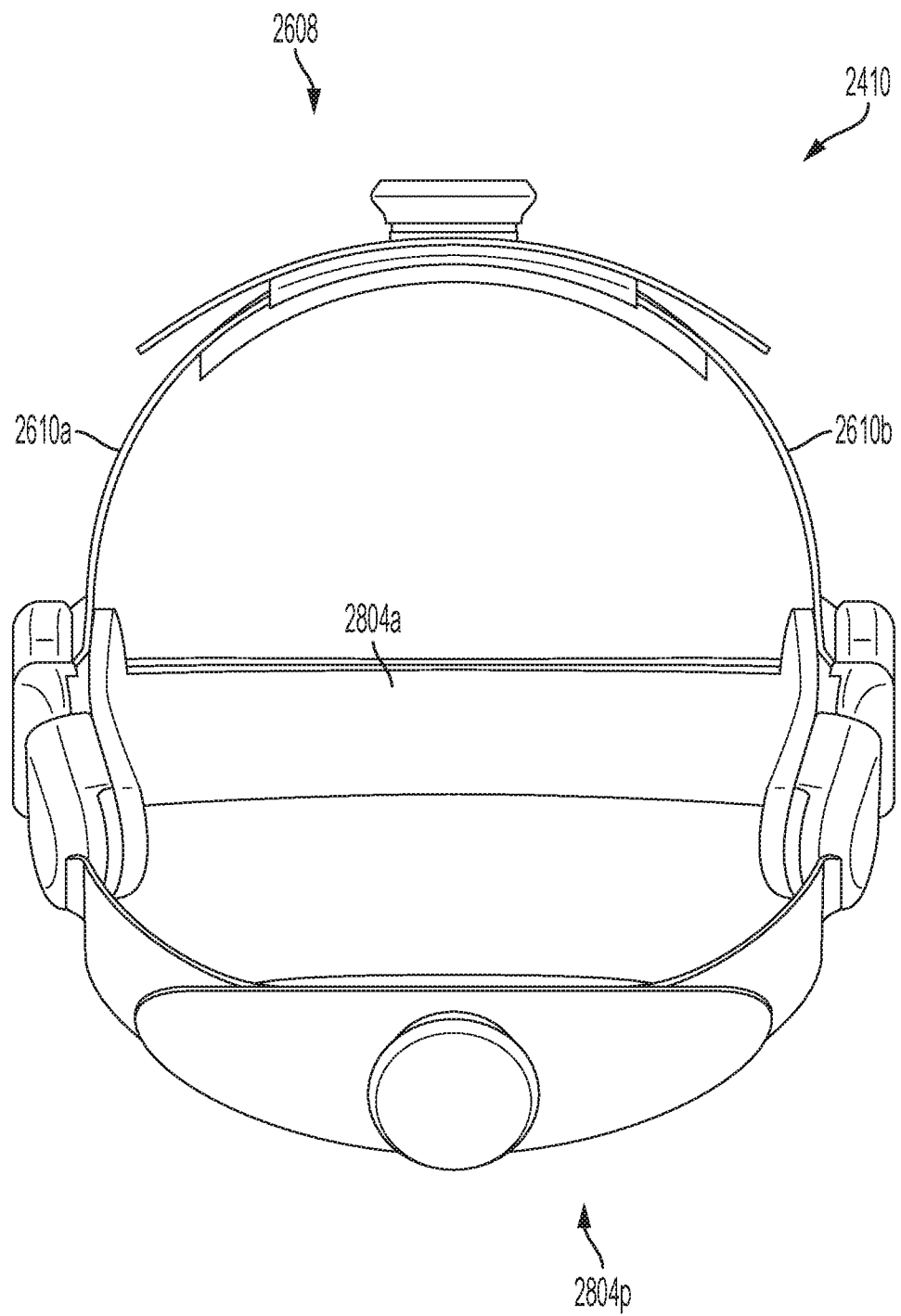
FIG. 30 shows a rear view of the exemplary harness of FIG. 25.
Figure 31A:
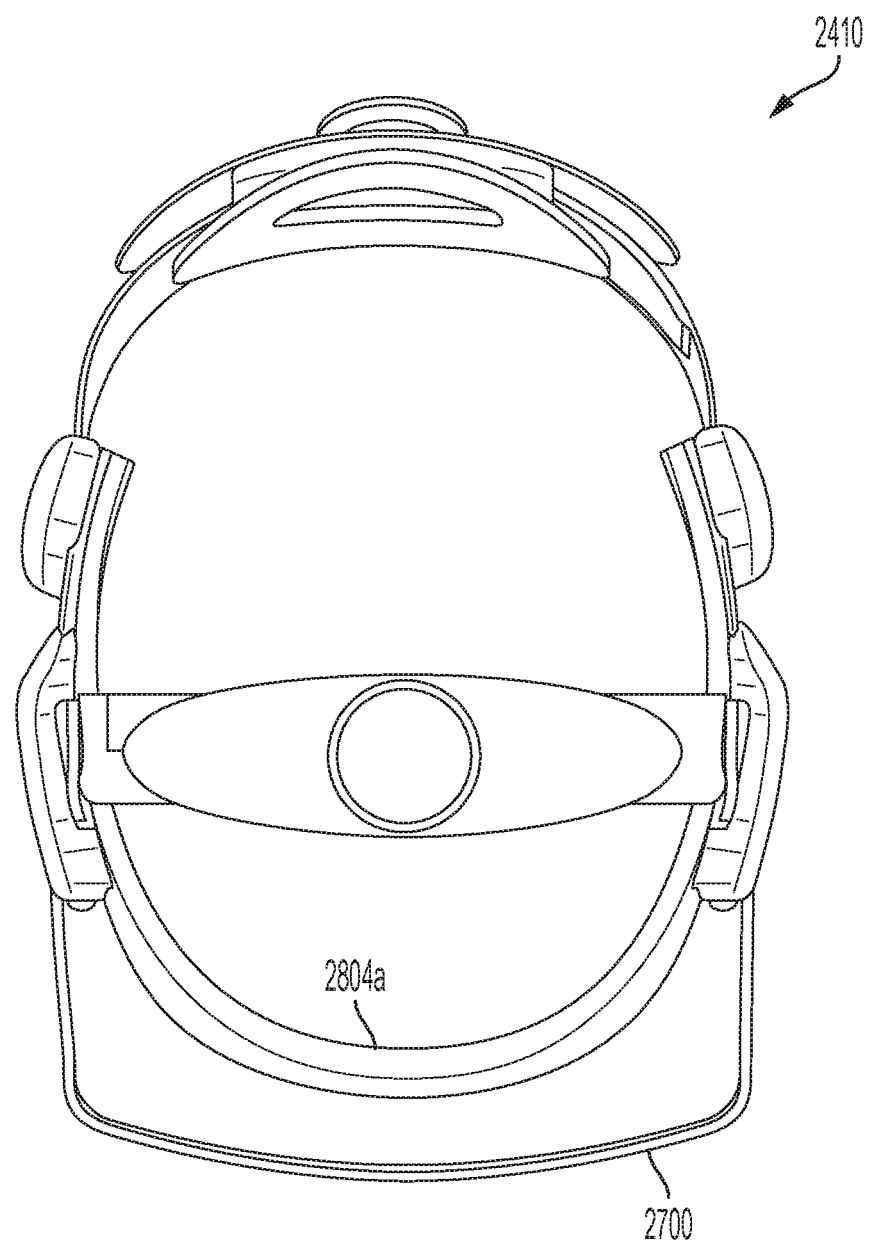
FIG. 31A shows a top view of the exemplary harness of FIG. 25.
Figure 31B:
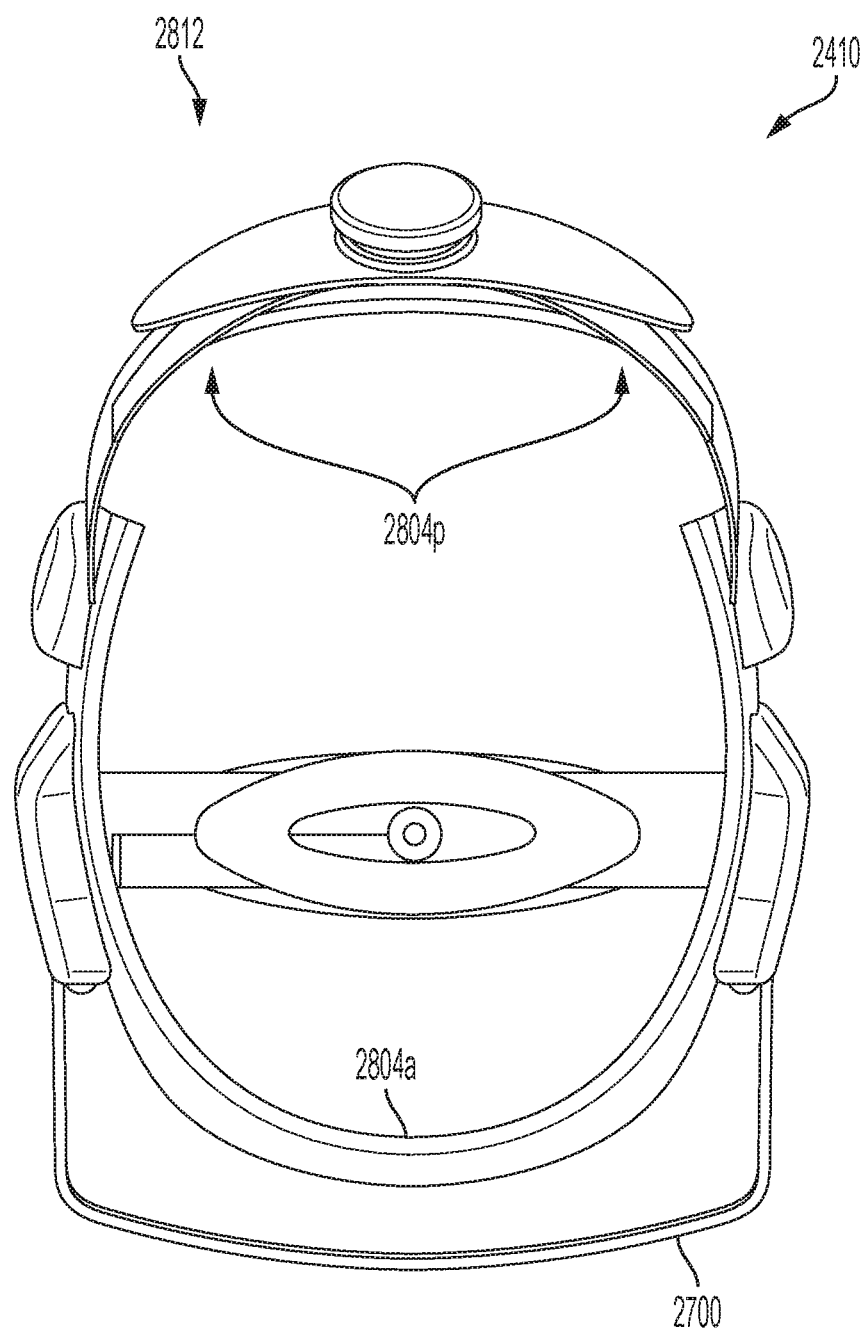
FIG. 31B shows a bottom view of the exemplary harness of FIG. 25.

Additional details of the exemplary harness 2400 in accordance with various aspects of the present teachings will now be discussed in more details with reference to FIGS. 25-31. As shown in these figures, the headgear 2410 of the harness 2400 generally comprises an encircling portion 2804 that is configured to encircle (e.g., go around) the patient's head, for example, above the level of the patient's ears. The encircling portion 2804 may contact all or a portion of the subject's head's circumference. As shown in FIGS. 28A-B, the anterior section 2804a of the encircling portion can be disposed against the patient's forehead, and can, for example, comprise a padded material so as to increase the patient's comfort when the harness is secured to the patient's head. The padded material 2805 used in the anterior section 2804a is shown in detail in FIG. 29. The encircling portion 2804 can also comprise a rear section 2804p (made of the same or different material as the anterior section 2804a) that is configured to be secured against the posterior side of the patient's head, for example, in the region of the occipital lobe. In various aspects, the rear section 2804p can be rotated (e.g., via rotatable hub 2807) and/or a length (e.g., a circumference) of the encircling portion 2804 can be adjusted via an adjustment mechanism to help ensure that the harness 2400 is securely coupled to the patient's head. As best shown in FIGS. 26 and 30, for example, the rear section 2804p of the encircling portion 2804 can comprise two rearwardly extending straps 2806a and 2806b that are coupled to one another in the region of the patient's occipital lobe, the coupling of which can be adjusted (e.g., by snap fit, sliding, compression fit, etc.) so as to alter the length of the rear section 2804p. As shown in FIG. 31B, for example, a knob of an adjustment mechanism 2812 can thus be rotated to increase or decrease the overlap of the straps 2806a,b so as to adjust the size of the rear section 2804p to conform to the back of the patient's head. As shown, the straps 2806a,b can be coupled to the anterior section 2804a at a rotatable hub such that the angle of the rear section 2804p can be changed relative to the anterior section 2804a.

Additionally, referring now to FIG. 28A, in some aspects, the headgear 2410 can include a superior connector 2608 extending between lateral sides of the encircling portion 2804 (e.g., in the subject's temple region) that can be disposed against the top of the patient's head to provide additional support to the harness 2400. In various aspects, the superior connector 2608 can be rotated and/or a length of the superior connector 2608 can be adjusted via an adjustment mechanism 2612 to help ensure that the harness 2400 is secured to the patient's head. As shown in FIG. 26, for example, the superior connector 2608 can comprise two upwardly extending straps 2610a and 2610b that overlap each other within an adjustment mechanism 2612. In such aspects, a knob of the adjustment mechanism 2612 can thus be rotated to increase or decrease the overlap of the straps 2610a,b so as to adjust the size of the superior connector 2608 to lie against the top of the patient's head. As shown, the straps 2610a,b can also be rotatably coupled to the headgear 2410 at a rotatable hub such that the angle of the superior connector 2608 can be changed relative to the anterior section 2804a.

Figure 27:
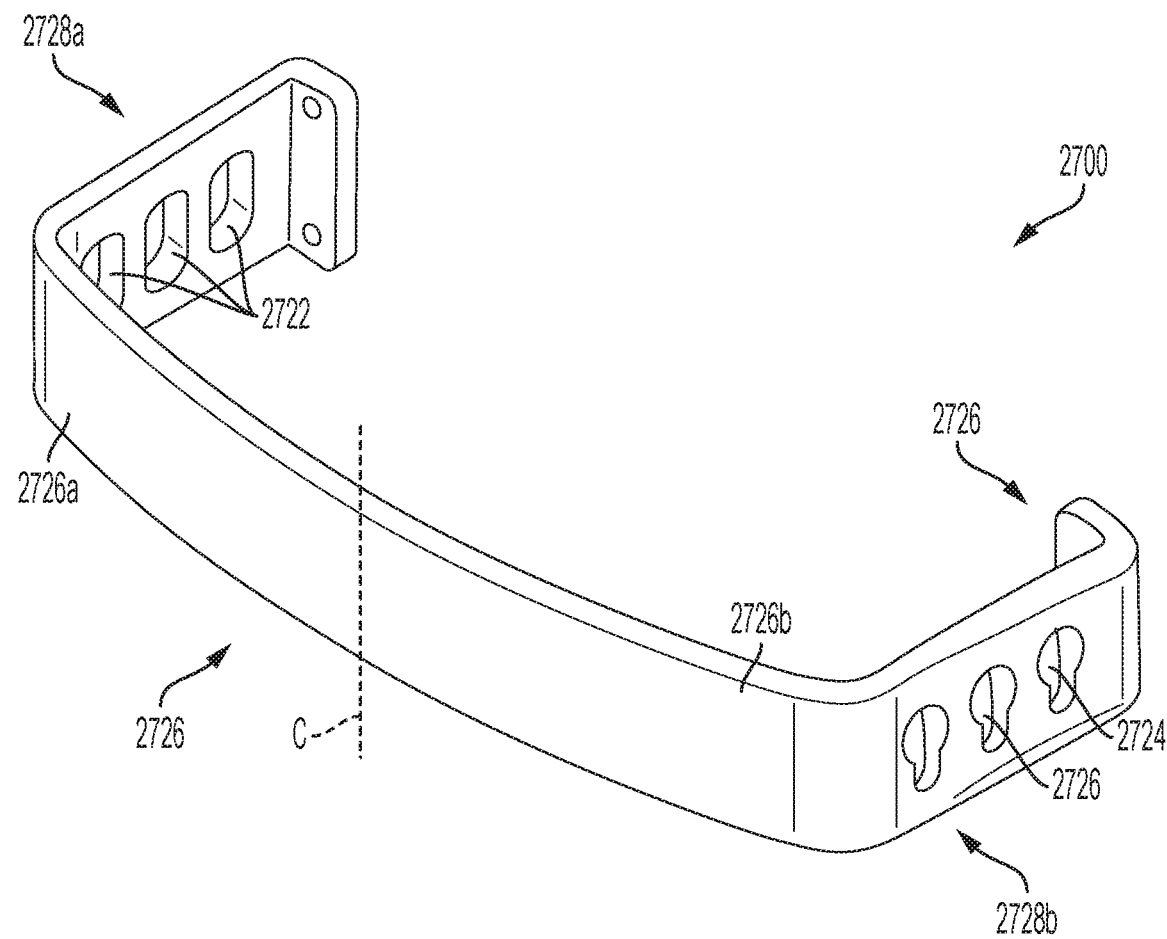
FIG. 27 shows a perspective view of a brim of the exemplary harness of FIG. 25 in additional detail.
Figure 28A:
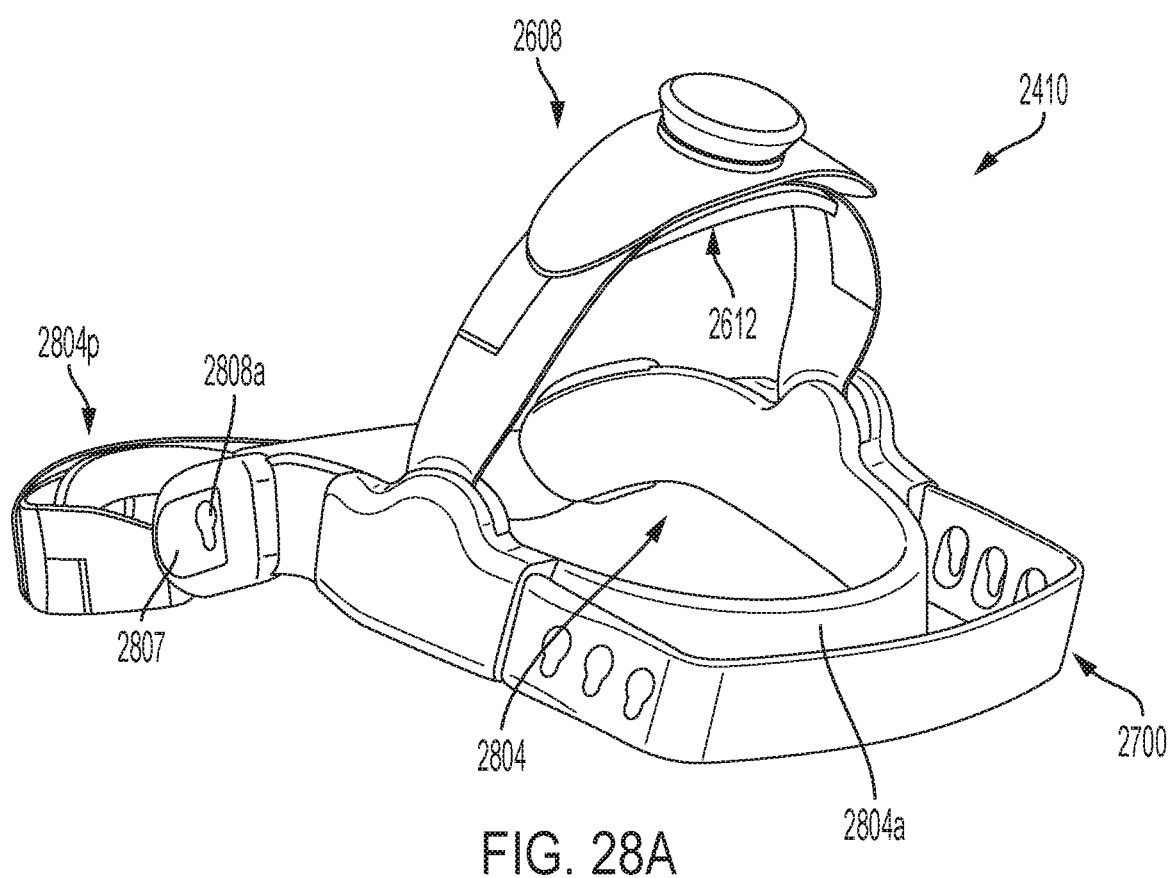
FIG. 28A shows a right side perspective view of the exemplary harness of FIG. 25.
Figure 28B:
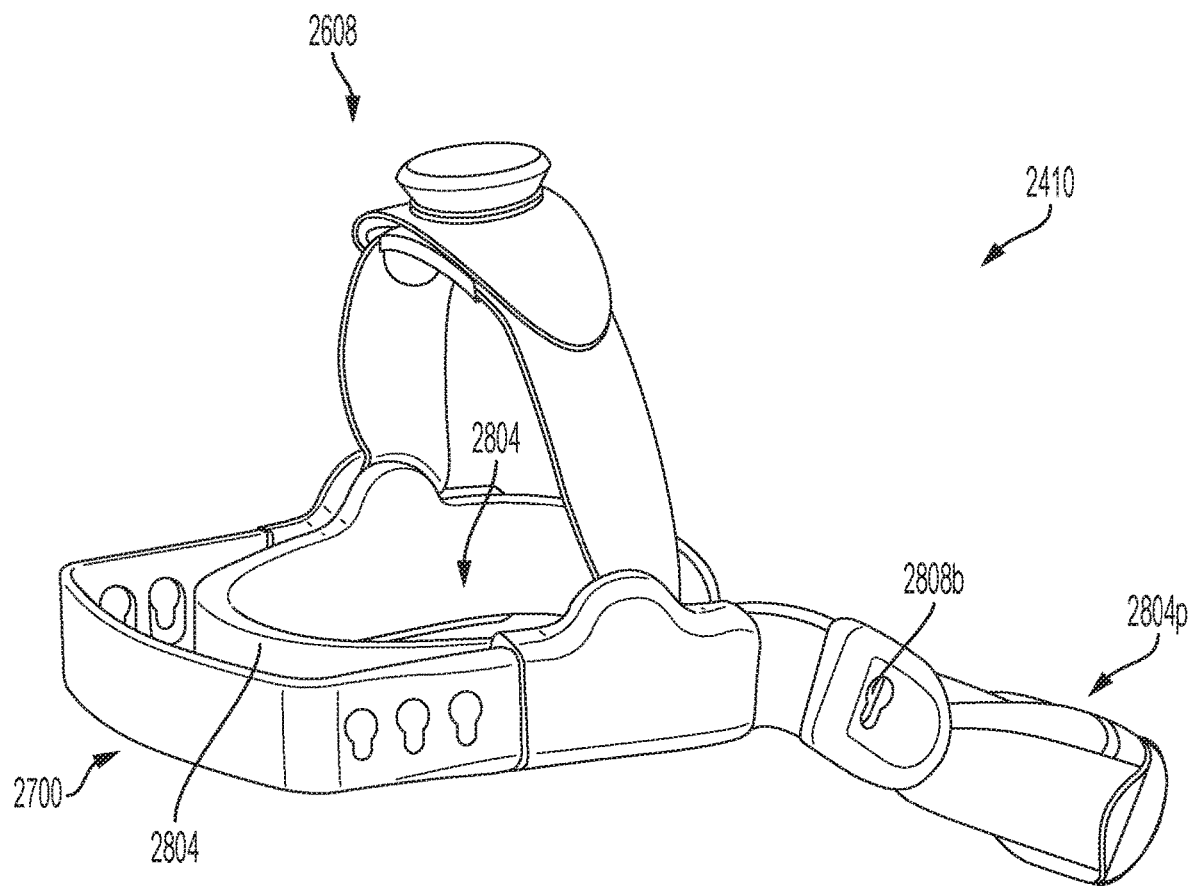
FIG. 28B shows a left side perspective view of the exemplary harness of FIG. 25.
Figure 29:
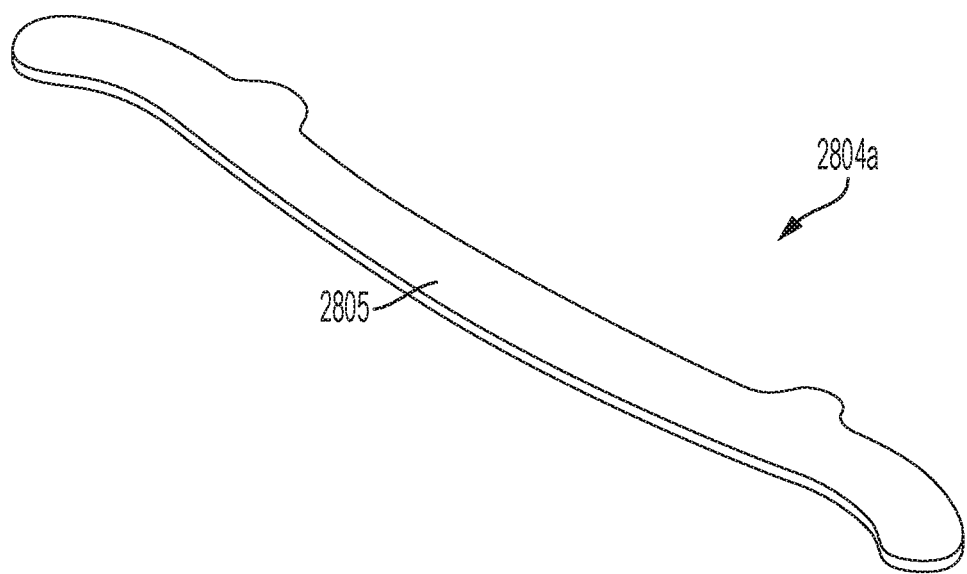
FIG. 29 shows a perspective view of a portions of a padded encircling portion of the exemplary harness of FIG. 25.

With particular reference now to FIGS. 27 and 28A-B, the headgear 2410 additionally includes a brim 2700 that extends anteriorly from lateral sides of the encircling portion 2804 (e.g., in the region of the patient's temple) and generally across the subject's forehead. As shown in the figures, the exemplary brim 2700 comprises a frontal longitudinal bar 2726 that is generally disposed horizontally across the patient's forehead and that extends between a first lateral end 2726a and a second lateral end 2726b on opposed sides of the centerline of the subject's face. From each of the opposed lateral ends 2726a,b, lateral longitudinal bars 2728a,b extend posteriorly and terminate in a posterior end that is configured to be coupled to the encircling portion 2804, for example, in a generally rigid connection so as to support and/or compress the frame 2404 against the patient's treatment area (e.g., the submental region) upon coupling via connectors 2420a,b (as shown in FIGS. 24A,B). It will be appreciated that the frontal longitudinal bar 2726 and the lateral longitudinal bars 2728a,b can be a single unitary piece (e.g., generally rigid plastic) or can comprise multiple pieces coupled to one another (e.g., directly or indirectly) so as to form the brim 2700. The one or more segments of the brim 2700 can be straight, curved, or a combination of both, and can be made of a variety of materials such as a metal, plastic, resin, polymer, composite, or any combination thereof, all by way of non-limiting example.

With continued reference to FIGS. 24A-C and 27, the brim 2700 additionally comprises a plurality of anterior coupling elements 2722 (i.e., two or more) on each lateral side of the centerline (C), each of which is configured to removably couple the brim 2700 to the frame 2404 via one or more anterior connectors 2420a having a corresponding mating element that can couple to each of the anterior coupling elements 2722. As shown, three anterior coupling elements 2722 are disposed on each of the lateral longitudinal bars 2728a,b, though it will be appreciated that more and fewer anterior coupling elements 2722 can be provided and that they can be disposed at a variety of locations along the brim 2700 such that in some embodiments the anterior coupling elements 2722 on each lateral side are spaced anteriorly relative to one another. In this manner, the one or more anterior connectors 2420a,b can be removably coupled, de-coupled, and re-positioned (e.g., coupled to a different anterior coupling element 2722) such that the angle of the anterior connectors 2420a,b between the frame 2404 and the brim 2700 can be selected to optimize the positioning of the frame 2404 on the treatment region (e.g., the submental region) according to the patient's anatomy and/or to aid patient comfort. In addition to the exemplary description above with respect to the treatment of the patient's submental region, referring now to FIGS. 24D-E, the plurality of anterior coupling elements 2722 can in some aspects allow for the treatment of a variety of treatment regions of the subject's head (e.g., jowls, cheeks) by enabling the proper positioning and orientation of one or more frames 2404 relative to the desired treatment region and/or by adjusting the angle and/or length of the connectors 2420 coupling with the brim 2700. As shown in FIGS. 24D-24E, the frame can be offset relative to the centerline to treat one lower cheek/jowl area on one lateral side of the subject, here, the selection of desired anterior coupling elements 2722 and the length and/or angle of the connectors 2420 is adjusted to enable the lower cheek/jowl area to be in contact with the frame 2404. In addition, the practitioner may select a mask having an aperture suited to the treatment area. A secondary treatment may optionally be performed to address the lower cheek/jowl area of the subject to assure a symmetrical treatment result. By way of example, in some aspects a plurality of frames can be provided (e.g., for simultaneous treatment of both jowls or both cheeks on both sides of the subject's head), and the frames can be connected (e.g., via strap passing under the patient's chin) with mating elements from one lateral side of each frame being coupled to the anterior coupling elements on that lateral side of the brim via an anterior connector. Here two applicators will be utilized each with one of the two frames, one on each jowl or cheek.

As will be appreciated by a person skilled in the art in view of the present teachings, referring to FIGS. 24A-C, the anterior coupling elements 2722 and the anterior connector(s) 2420a,b can be configured to removably couple to one another (e.g., so as to allow for adjustment as otherwise described herein) in a variety of manners. As shown, for example, in FIGS. 27 and 28A-B, the exemplary anterior coupling elements 2722 can comprise a plurality of identical key holes having a wide superior portion 2724 and a narrower inferior portion 2726 such that a corresponding male mating element on the superior end of the anterior connector(s) 2420a,b can be inserted into the wide superior portion 2724 and can be retained (as with a button) within the narrower inferior portion 2726 of the coupling element 2722 (e.g., by tightening the connector or by tension generated by a flexible connector). It will be appreciated that the corresponding coupling elements 2722 of the brim 2700 and the mating elements of the connectors 2420a,b can be coupled via one or more of snap-fit, compression fit, tension fit, male-female attachment, clamp, clip, hook and eye, clothespin, buckle, bungee, or zip tie etc., all by way of non-limiting example.

As discussed above, and referring to FIGS. 24A-C, the harness 2400 can additionally include one or more anterior connectors 2420a,b that are configured to extend between the brim 2700 and the frame 2404 for comfortably retaining the frame at a desired location within the treatment region (e.g., the submental region). The anterior connectors 2420a,b can have a variety of configurations through are shown in the exemplary depicted harness 2400 as being a strap that can extend from a superior end 2412 having a mating element 2412a configured to couple to one of the corresponding anterior coupling elements 2722 to an inferior end 2414 having a mating element 2414a configured to couple to a corresponding coupling element formed on the frame 2404 (as discussed otherwise herein). As discussed above, the superior and inferior mating elements 2412a and 2414a of the connectors 2420a,b can have a variety of configurations for removably coupling to the corresponding anterior coupling elements 2722 formed on the brim 2700 and/or frame 2404 (e.g., one or more of snap-fit, compression fit, tension fit, male-female attachment, clamp, clip, hook and eye, clothespin, buckle, bungee, or zip tie etc.).

Alternatively, in some aspects, it will be appreciated that a single anterior connector 2420 having an anterior coupling element (e.g., 2412a) on each end thereof can, for example, extend through a loop on the frame 2404, with each of the mating elements 2414a being removably coupled to anterior coupling elements 2722 on opposed lateral sides of the brim 2700. Additionally, in some aspects, a length of the one or more anterior connector(s) 2420 can be adjustable (e.g., via an adjustable buckle) so as to increase or decrease a tension on the connector(s) to help maintain contact and/or patient comfort. In some aspects, for example, the length of the anterior connector(s) 2420 can be adjusted after its mating elements are coupled to the brim 2700 and/or frame 2404.

With particular reference now to FIGS. 28A-B, the encircling portion 2804 can additionally comprise at least one posterior coupling elements 2808a,b on each lateral side of the centerline, each of which is configured to removably couple the harness 2400 at a relatively-posterior location to the frame 2404 via one or more posterior connectors 2420c,d (only one of the posterior coupling elements 2808 is shown). Though only one posterior coupling element 2808a,b is shown as being disposed on each lateral side of the subject's head (e.g., behind the ear), it will be appreciated that more and fewer posterior coupling elements 2808a,b can be provided and that they can be disposed at a variety of posteriorly-spaced locations along the encircling portion 2804 (e.g., directly above the patient's ear, behind the patient's ear) to allow for adjustment of the angle of the posterior connectors 2420c,d. It will also be appreciated that the posterior coupling elements 2808a,b can couple the frame 2404 to the harness 2400 at a different angle from the anterior connectors 2420a,b to optimize contact with the treatment region (e.g., the submental region) and/or to aid patient comfort, for example, depending on the patient's anatomy. Like the anterior connectors 2420a,b, a length of the posterior connectors 2420a,b can also be adjusted (i.e., increased or decreased) to help maintain contact and/or comfort. In one exemplary embodiment, the posterior coupling elements 2808 and the anterior coupling elements 2722 are the same and as such the posterior connectors 2420c,d can be interchangeable with anterior connectors 2420a,b.

Positioning of the anterior coupling elements 2722 on the brim 2700 anterior to the subject's forehead enables the connectors 2420a, b to support the frame in such a way that good contact of the frame, mask, and/or applicator is present between the head and neck treatment region while maintaining a comfortable position of the frame, mask, and/or applicator relative to the subject's neck. The position of the posterior coupling elements and their connectors 2420c,d likewise enables a comfortable position to be maintained. Further, positioning the plurality of coupling elements 2722 on the brim 2700 anterior to the subject's forehead increases the number of head shapes and types that can be treated using the system described herein. Further still, this configuration enables a subject to comfortably wear glasses (including safety glasses that are necessary for at least some treatment energy modalities) without the risk that the glasses will be pushed off by the harness during the treatment. The subject enjoys the ability to move his head during the treatment and comfortably sit, stand, or lie down. The subject can read, work on the computer and/or comfortably hold a conversation while wearing the harness during his treatment. The subject is not enclosed by the harness, so he is unlikely to feel claustrophobic or trapped and his harness can be adjusted to ensure that his neck is not contacted by a portion of the side of the frame and/or applicator, in this way a feeling of choking and/or windpipe contact is avoided.

The systems and methods disclosed herein is discussed in relation to treatment of body areas having undesired fat and bulges. The disclosed system and method of treatment of external treatment of the body of a subject may applied to other treatment modalities that are external to the body (e.g., non-invasive) such as, for example, pain treatment, acne treatment, wound treatment, skin rejuvenation, and/or skin tightening.

In one aspect, this disclosure relates to a system for substantially unattended treatment including a frame encircling at least portion of a circumference of a body region. The frame has at least one aperture sized to isolate at least one portion of a body region and the frame has a first fastening member. The system also includes an applicator having a skin contacting surface. The applicator has a second fastening member that detachably fastens with the first fastening member when the applicator is inserted into the frame. In one embodiment, the first fastening member and the second fastening member include a male member and a female member that snap fit. In one embodiment, at least two frames of a plurality of frames are attached to one another by a hinge.

The system can include a belt and the frame is removably attached to the belt. All or a portion of the belt may be flexible. All or a portion of the belt can encircle the portion of the circumference of the body region.

In one embodiment, the applicator emits hyperthermic energy through the skin contacting surface.

In one aspect, this disclosure relates to a system for substantially unattended treatment including a frame encircling at least portion of a circumference of a body region. The frame has at least one aperture sized to isolate at least one portion of a body region and the frame has a first fastening member. The system also includes an applicator having a skin contacting surface. The applicator has a second fastening member that detachably fastens with the first fastening member when the applicator is inserted into the frame. In one embodiment, the umbilical cord has a first end coupled to an energy source and a second end coupled to the applicator. In some embodiments, the system includes an arm having a braking mechanism. A portion of the umbilical cord between the two ends is threaded through the breaking mechanism and the breaking mechanism holds a portion of the umbilical cord selected by the user so that the position of umbilical cord that lies between the breaking mechanism and the applicator enables the desired contact between the applicator skin contact surface and the portion of the body.

In another aspect, the disclosure relates to methods of treatment of a body region using a frame having at least one aperture to isolate a body region and then bringing the contact surface of an applicator in contact with the body region by fastening the applicator to the frame and treating the body region for any of a number conditions such as unwanted fat bulges, acne, pain, wound healing, and loose skin via this non-invasive approach.

While the foregoing figures and examples refer to specific elements, this is intended to be by way of example and illustration only and not by way of limitation. It should be appreciated by the person skilled in the art that various changes can be made in form and details to the disclosed embodiments without departing from the scope of the teachings encompassed by the appended claims.

The invention claimed is:

1. A method of treating a region of a subject's head or neck, comprising:
    coupling a harness to a subject's head such that
    an encircling portion of the harness is secured around a subject's head and
    a brim is disposed anterior to the subject's forehead, the brim extending anteriorly from the encircling portion,
    the brim comprising a plurality of anterior coupling elements, wherein a first plurality of anterior coupling elements of the plurality of anterior coupling elements is disposed on a first side of the brim;
    coupling a mating feature of an anterior connector to one of the first plurality of anterior coupling elements;
    disposing a frame coupled to the anterior connector in contact with a desired treatment region of the subject's head or neck such that a surface of the subject's skin extends through at least one aperture of the frame;
    coupling a treatment applicator to the frame such that a window of the treatment applicator contacts skin of subject; and
    applying energy to the treatment region through the window of the treatment applicator and the at least one aperture in the frame.

2. The method of claim 1, wherein the plurality of anterior coupling elements are disposed on one or both lateral sides of the subject's head anterior to the subject's temple, and further comprising coupling an anterior connector to one of the anterior coupling-elements.

3. The method of claim 2, wherein the encircling portion comprises a posterior coupling element on each lateral side of the subject's head above and/or posterior to the subject's ears,
    wherein the method further comprises coupling a superior mating feature of each of two posterior connectors to the posterior coupling elements on the corresponding lateral side of the subject's head.

4. The method of claim 3, further comprising adjusting a length of the two posterior connectors.

5. The method of claim 1, further comprising de-coupling the superior mating feature of the anterior connector from said one of the plurality coupling elements of the brim and coupling with another of said plurality of coupling elements.

6. The method of claim 1, further comprising adjusting a length of the anterior connector to secure the frame against a submental region.

7. The method of claim 1, wherein coupling the harness to the patient's head comprises adjusting a length of the encircling portion.

8. The method of claim 7, wherein the harness comprises a superior connector extending between opposed lateral sides of the encircling portion, the method further comprising adjusting a length of the superior connector to be disposed against the top of the subject's head.

9. The method of claim 1, wherein the treatment region comprises one of submental, jowl, and cheek tissue.

10. The method of claim 1, wherein a second anterior coupling element of the plurality of anterior coupling elements is disposed on a second side of the brim.

* * * * *